(12) United States Patent
Abrams et al.

(10) Patent No.: US 8,546,434 B2
(45) Date of Patent: Oct. 1, 2013

(54) TRIAZOLE COMPOUNDS AS KSP INHIBITORS

(75) Inventors: Tinya Abrams, Richmond, CA (US); Paul Barsanti, Pleasant Hill, CA (US); Yu Ding, Union City, CA (US); David Duhl, Oakland, CA (US); Wooseok Han, San Ramon, CA (US); Cheng Hu, Menlo Park, CA (US); Yue Pan, Albany, CA (US)

(73) Assignee: Novartis AG, Basel (CH)

( * ) Notice: Subject to any disclaimer, the term of this patent is extended or adjusted under 35 U.S.C. 154(b) by 72 days.

(21) Appl. No.: 13/085,746

(22) Filed: Apr. 13, 2011

(65) Prior Publication Data

US 2011/0256128 A1 Oct. 20, 2011

Related U.S. Application Data

(60) Provisional application No. 61/324,651, filed on Apr. 15, 2010.

(51) Int. Cl.
| | |
|---|---|
| A61K 31/44 | (2006.01) |
| A61K 31/54 | (2006.01) |
| A61K 31/445 | (2006.01) |
| C07D 249/08 | (2006.01) |
| C07D 413/02 | (2006.01) |

(52) U.S. Cl.
USPC .................................... 514/383; 548/262.2

(58) Field of Classification Search
USPC .................................... 514/383; 548/262.2
See application file for complete search history.

(56) References Cited

U.S. PATENT DOCUMENTS

| | | | |
|---|---|---|---|
| 7,902,240 B2 * | 3/2011 | Xia et al. ...................... 514/383 |
| 8,129,358 B2 * | 3/2012 | Xia et al. ...................... 514/49 |
| 2006/0009472 A1 | 1/2006 | Wang et al. |

FOREIGN PATENT DOCUMENTS

| | | |
|---|---|---|
| WO | WO 2004/032840 | 4/2004 |
| WO | WO 2006/049835 A2 | 5/2006 |
| WO | WO 2007/021794 A1 | 2/2007 |
| WO | WO 2008/063912 * | 5/2008 |
| WO | WO 2008/063912 A1 * | 5/2008 |
| WO | WO 2008/063912 A1 | 5/2008 |
| WO | WO 2008/086122 A2 | 7/2008 |
| WO | WO 2011/128388 A2 | 10/2011 |

OTHER PUBLICATIONS

Patani et al., Chem Rev, 1996, vol. 96 (8), especially p. 3149.*

* cited by examiner

*Primary Examiner* — Susannah Chung

(74) *Attorney, Agent, or Firm* — Michael G. Smith

(57) ABSTRACT

The present invention provides triazole compounds of Formula I:

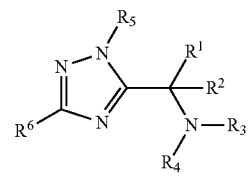

as further described herein. The invention also provides a pharmaceutical composition comprising a therapeutically effective amount of a compound of Formula I, and a method of treating a disorder mediated, at least in part, by KSP in a mammalian patient comprising administering to a mammalian patient in need of such treatment a therapeutically effective amount of a compound of Formula I.

22 Claims, No Drawings

TRIAZOLE COMPOUNDS AS KSP INHIBITORS

CROSS-REFERENCE TO RELATED APPLICATIONS

This application claims the benefit under 35 U.S.C. §119 (e) to U.S. provisional application Ser. No. 61/324,651, filed on 15 Apr. 2010, which is incorporated herein in its entirety by reference.

FIELD OF THE INVENTION

This invention generally relates to triazole compounds and pharmaceutically acceptable salts, esters, or prodrugs thereof. This invention is further directed to compositions of such compounds together with pharmaceutically acceptable carriers, to uses of such compounds, to their preparation, and to related intermediates.

BACKGROUND

Kinesins are motor proteins that use adenosine triphosphate to bind to microtubules and generate mechanical force. Kinesins are characterized by a motor domain having about 350 amino acid residues. The crystal structures of several kinesin motor domains have been resolved.

Currently, about one hundred kinesin-related proteins (KRP) have been identified. Kinesins are involved in a variety of cell biological processes including transport of organelles and vesicles, and maintenance of the endoplasmic reticulum. Several KRPs interact with the microtubules of the mitotic spindle or with the chromosomes directly and appear to play a pivotal role during the mitotic stages of the cell cycle. These mitotic KRPs are of particular interest for the development of cancer therapeutics.

Kinesin spindle protein (KSP) (also known as Eg5, HsEg5, KNSL1, or KIF11) is one of several kinesin-like motor proteins that are localized to the mitotic spindle and known to be required for formation and/or function of the bipolar mitotic spindle.

In 1995, the depletion of KSP using an antibody directed against the C-terminus of KSP was shown to arrest HeLa cells in mitosis with monoastral microtubule arrays (Blangy et al., Cell 83:1159-1169, 1995). Mutations in bimC and cut7 genes, which are considered to be homologues of KSP, cause failure in centrosome separation in *Aspergillus nidulans* (Enos, A. P., and N. R. Morris, Cell 60:1019-1027, 1990) and *Schizosaccharomyces pombe* (Hagan, I., and M. Yanagida, Nature 347:563-566, 1990). Treatment of cells with either ATRA (all trans-retinoic acid), which reduces KSP expression on the protein level, or depletion of KSP using antisense oligonucleotides revealed a significant growth inhibition in DAN-G pancreatic carcinoma cells indicating that KSP might be involved in the antiproliferative action of all trans-retinoic acid (Kaiser, A., et al., J. Biol. Chem. 274, 18925-18931, 1999). Interestingly, the *Xenopus laevis* Aurora-related protein kinase pEg2 was shown to associate and phosphorylate XlEg5 (Giet, R., et al., J. Biol. Chem. 274:15005-15013, 1999). Potential substrates of Aurora-related kinases are of particular interest for cancer drug development. For example, Aurora 1 and 2 kinases are overexpressed on the protein and RNA level and the genes are amplified in colon cancer patients.

The first cell permeable small molecule inhibitor for KSP, "monastrol," was shown to arrest cells with monopolar spindles without affecting microtubule polymerization as do conventional chemotherapeutics such as taxanes and vinca alkaloids (Mayer, T. U., et al., Science 286:971-974, 1999). Monastrol was identified as an inhibitor in phenotype-based screens and it was suggested that this compound may serve as a lead for the development of anticancer drugs. The inhibition was determined not to be competitive in respect to adenosine triphosphate and to be rapidly reversible (DeBonis, S., et al., Biochemistry, 42:338-349, 2003; Kapoor, T. M., et al., J. Cell Biol., 150:975-988, 2000).

In light of the importance of improved chemotherapeutics, there is a need for KSP inhibitors that are effective in vivo inhibitors of KSP and KSP-related proteins.

SUMMARY OF THE INVENTION

In one embodiment, this invention is directed to substituted triazole compounds and the pharmaceutically acceptable salts, esters, or prodrugs thereof, their preparation, pharmaceutical compositions, and uses for treating KSP mediated diseases, wherein the compounds are represented by the general Formula:

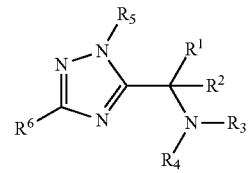

wherein, $R^1$ can be selected from $C_{1-6}$ alkoxy-$C_{1-4}$-alkyl, $C_{1-6}$ straight chain alkyl, $C_{3-6}$ branched alkyl, and —$C_{3-6}$ cyclo alkyl;

$R^2$ is selected from H, and $C_{1-6}$ straight chain alkyl;

$R^3$ represents —$(CH_2)_{0-3}$ substituted or unsubstituted pyrrolidinyl or an optionally substituted $C_{3-5}$ alkyl;

$R^4$ is selected from —C(O)—$CH_2OH$, —C(O)-tetrahydrofuranyl, —C(O)—CH($CH_3$)—OH,
—C(O)-unsubstituted morpholinyl, and —C(O)-morpholinyl substituted with up to three alkyl groups;

$R^5$ is selected from substituted or unsubstituted benzyl, wherein the substituents are selected from Cl, F, Br, and I; and $R^6$ is selected from phenyl substituted with up to three halogen atoms.

In certain embodiments of these compounds of Formula I: $R^1$ is selected from $C_{1-6}$ straight chain alkyl, $C_{3-6}$ branched alkyl, and —$C_{3-6}$ cyclo alkyl;

$R^2$ is selected from H, and $C_{1-6}$ straight chain alkyl;

$R^3$ represents —$(CH_2)_{0-3}$ substituted or unsubstituted pyrrolidinyl;

$R^4$ is selected from —C(O)—$CH_2OH$, —C(O)-tetrahydrofuranyl, —C(O)—CH($CH_3$)—OH,
—C(O)-unsubstituted morpholinyl, and —C(O)-morpholinyl substituted with up to three alkyl groups;

$R^5$ is selected from substituted or unsubstituted benzyl, wherein the substituents are selected from Cl, F, Br, and I; and $R^6$ is selected from phenyl substituted with up to three halogen atoms.

In other embodiments, $R^1$ is $C_{1-6}$alkoxy-$C_{1-4}$alkyl, such as methoxy-substituted $C_{1-4}$ alkyl and 2-methoxy-2-propyl.

The invention also provides methods for making and for using these compounds, and pharmaceutical compositions containing these compounds, as further described herein.

DETAILED DESCRIPTION OF EMBODIMENTS OF THE INVENTION

Compounds of the invention include those of Formula (I) or a pharmaceutically acceptable salt, ester, or prodrug thereof:

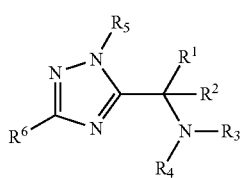

(I)

wherein:

$R^1$ is selected from $C_{1-6}$alkoxy-$C_{1-4}$alkyl, $C_{1-6}$ straight chain alkyl, $C_{3-6}$ branched alkyl, and $C_{3-6}$ cyclo alkyl;

$R^2$ is selected from H, and $C_{1-6}$ straight chain alkyl;

$R^3$ represents —(CH$_2$)$_{0-3}$-substituted or unsubstituted pyrrolidinyl, such as —CH$_2$-pyrrolidinyl;

$R^4$ is selected from —C(O)—CH$_2$OH, —C(O)-tetrahydrofuranyl, —C(O)—CH(CH$_3$)—OH, —C(O)-unsubstituted morpholinyl, and —C(O)-morpholinyl substituted with up to three alkyl groups;

$R^5$ is selected from substituted or unsubstituted benzyl, wherein the substituents are selected from Cl, F, Br, and I; and $R^6$ is selected from phenyl substituted with up to three halogen atoms.

In compounds of Formula I, $R^1$ is often a branched-chain alkyl or an alkoxy alkyl, and $R^2$ is often H. In a preferred embodiment, the compound of Formula I can be this isomer:

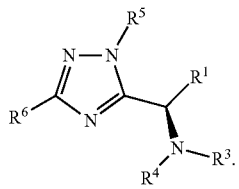

In these compounds, $R^5$ is often benzyl, which is optionally substituted with up to 3 halogen atoms on the phenyl ring of the benzyl group. $R^5$ can be unsubstituted; when it is substituted, it is often substituted with one or two fluorine atoms.

$R^6$ is typically an optionally substituted phenyl ring; in some embodiments, it is phenyl substituted by 1-2 halo groups. In preferred embodiments, $R^6$ is fluorophenyl or difluorophenyl, particularly 2,5-difluorophenyl.

In certain embodiments of these compounds of Formula I, $R^1$ is selected from $C_{1-6}$ straight chain alkyl, $C_{3-6}$ branched alkyl, and —$C_{3-6}$ cyclo alkyl.

A specific embodiment of the present invention provides a compound of Formula I, wherein:

$R^1$ is selected from $C_{1-6}$alkoxy-$C_{1-4}$alkyl, preferably methoxy-substituted $C_{1-4}$alkyl;

$R^2$ represents H;

$R^3$ represents —(CH$_2$)$_{1-3}$-substituted pyrrolidinyl;

$R^4$ is selected from —C(O)-tetrahydrofuranyl, —C(O)—CH(CH$_3$)—OH, —C(O)-morpholinyl substituted with up to three alkyl groups;

$R^5$ represents benzyl, or benzyl substituted with up to two fluoro atoms; and $R^6$ is selected from phenyl substituted with up to two halogen atoms.

A further preferred embodiment of the present invention provides a compound of

Formula I, wherein:

$R^1$ is selected from $C_{3-6}$ branched alkyl;

$R^2$ represents H;

$R^3$ represents —(CH$_2$)$_{1-3}$-substituted pyrrolidinyl;

$R^4$ is selected from —C(O)-tetrahydrofuranyl, —C(O)—CH(CH$_3$)—OH, —C(O)-morpholinyl substituted with up to three alkyl groups;

$R^5$ represents benzyl, or benzyl substituted with up to two fluoro atoms; and $R^6$ is selected from phenyl substituted with up to two halogen atoms.

A further preferred embodiment of the present invention provides a compound of

Formula I, wherein:

$R^1$ represents t-butyl;

$R^3$ represents —(CH$_2$)-fluoro-pyrrolidinyl;

$R^4$ is selected from —C(O)-tetrahydrofuranyl, —C(O)—CH(CH$_3$)—OH, —C(O)-2,6-dimethyl morpholinyl;

$R^5$ represents benzyl, or benzyl substituted with one fluoro atom; and $R^6$ is selected from phenyl substituted with up to two fluoro atoms.

A further preferred embodiment of the present invention provides a compound of

Formula I, wherein:

$R^1$ represents methoxy-$C_{1-4}$alkyl;

$R^3$ represents —(CH$_2$)-fluoro-pyrrolidinyl;

$R^4$ is selected from —C(O)-tetrahydrofuranyl, —C(O)—CH(CH$_3$)—OH, —C(O)-2,6-dimethyl morpholinyl;

$R^5$ represents benzyl, or benzyl substituted with one fluoro atom; and $R^6$ is selected from phenyl substituted with up to two fluoro atoms.

Another preferred embodiment provides a compound of Formula I wherein, $R^3$ represents —(CH$_2$)$_{1-3}$-fluoro-pyrrolidinyl; and $R^4$ represents —C(O)-2-tetrahydrofuranyl, —C(O)—CH(CH$_3$)—OH, —C(O)-2,6-dimethyl morpholinyl. In particularly preferred embodiments, $R^4$ is selected from:

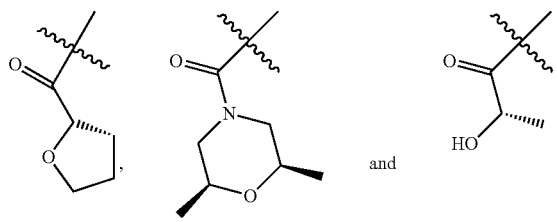

These R4 groups can be racemic or optically active; in preferred embodiments, R4 is an optically active group having the absolute stereochemistry depicted here. Typically, it is one enantiomer and is substantially free of its opposite enantiomer, i.e., the R4 group has an enantiomeric excess of at least 90% and often at least 95%.

Yet another preferred embodiment of the present invention provides a compound of Formula I, wherein:

$R^3$ represents a ((3R,4R)-4-fluoropyrrolidin-3-yl)methyl group

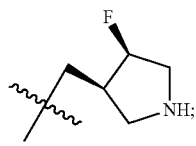 [SMILES: *C[C@@H]1CNC[C@@H]1F]

$R^4$ is selected from —C(O)—CH(CH$_3$)—OH, and

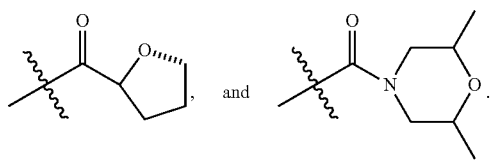

In particularly preferred embodiments, $R^4$ is selected from:

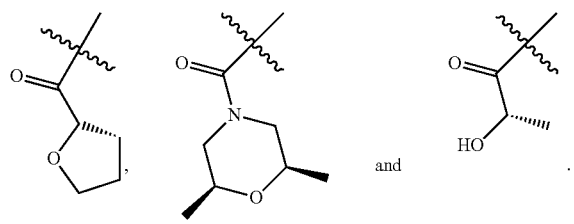

A further preferred embodiment of the present invention provides a compound of Formula I, wherein:

$R^5$ represents

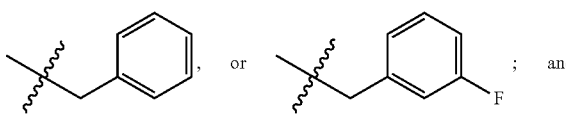

$R^6$ is

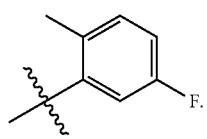 [SMILES: *c1cc(F)ccc1C]

In another embodiment, the invention provides compounds of Formula II:

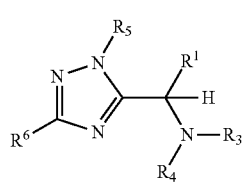

(II)

wherein, $R^1$ can be selected from $C_{1-6}$alkoxy-$C_{1-4}$-alkyl, $C_{1-6}$ straight chain alkyl, $C_{3-6}$ branched alkyl, and —$C_{3-6}$ cyclo alkyl;

$R^3$ represents —(CH$_2$)$_{0-3}$-substituted or unsubstituted pyrrolidinyl or $C_{3-5}$ alkyl substituted with up to three groups selected from amino and halo;

$R^4$ is selected from —C(O)—CH$_2$OH, —C(O)-tetrahydrofuranyl, —C(O)—CH(CH$_3$)—OH, —C(O)-unsubstituted morpholinyl, and —C(O)-morpholinyl substituted with up to three alkyl groups;

$R^5$ is selected from substituted or unsubstituted benzyl, wherein the substituents are selected from Cl, F, Br, and I (preferably F); and $R^6$ is selected from phenyl substituted with up to three halogen atoms, preferably F or Cl or both.

In compounds of Formula II, where $R^5$ or $R^6$ is substituted, preferred substituents are F and Cl.

In compounds of Formula II, $R^1$ is often a branched-chain alkyl substituted with an alkoxy group such as methoxy, and $R^2$ is often H. In a preferred embodiment, the compound of Formula II can be this isomer having the absolute stereochemistry shown:

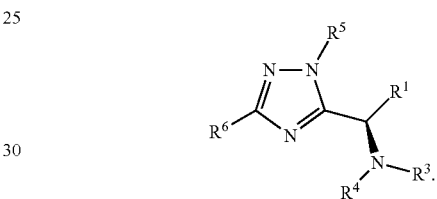

In particularly preferred embodiments of the compounds of Formula II, $R^4$ is selected from:

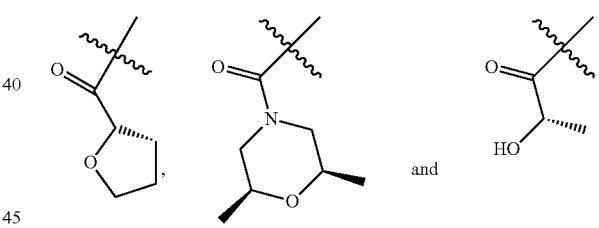

Preferably, these groups are optically active and have the absolute stereochemistry shown.

Yet another preferred embodiment of the present invention provides a compound of Formula II, wherein $R^3$ represents

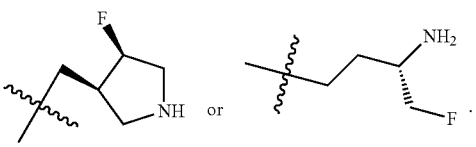 [SMILES: *C[C@@H]1CNC[C@@H]1F ; "or" ; *CC[C@H](N)CF ; "."]

These $R^3$ groups can be racemic or optically active; in preferred embodiments, $R^3$ is an optically active group having the absolute stereochemistry depicted here. Typically, it is one enantiomer and is substantially free of its opposite enantiomer, i.e., the $R^3$ group has an enantiomeric excess of at least 90% and often at least 95%.

In the compounds of Formula II, $R^5$ is often benzyl, which is optionally substituted with up to 3 halogen atoms on the phenyl ring of the benzyl group. $R^5$ can be unsubstituted; when it is substituted, it is often substituted with one or two fluorine atoms.

In the compounds of Formula II, $R^6$ is typically an optionally substituted phenyl ring; in some embodiments, it is phenyl substituted by 1-2 halo groups. In preferred embodiments, $R^6$ is fluorophenyl or difluorophenyl, particularly 2,5-difluorophenyl.

In certain embodiments of these compounds of Formula II:
$R^1$ is selected from C1-6 alkoxy-C1-4-alkyl, C3-6 branched alkyl, and C3-6 cyclo alkyl;
$R^3$ represents —(CH$_2$)$_{0-3}$-substituted pyrrolidinyl such as a ((3R,4R)-4-fluoropyrrolidin-3-yl)methyl group or —CH$_2$—CH$_2$—CH(NH$_2$)—CH$_2$F which is preferably

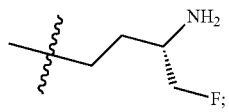

$R^4$ is selected from —C(O)—CH$_2$OH, —C(O)-tetrahydrofuranyl, —C(O)—CH(CH$_3$)—OH, —C(O)-unsubstituted morpholinyl, and —C(O)-morpholinyl substituted with up to three alkyl groups;
$R^5$ is selected from substituted or unsubstituted benzyl, wherein the substituents are selected from Cl, F, Br, and I; and
$R^6$ is selected from phenyl substituted with up to three halogen atoms.

In certain embodiments of the compounds of Formula II, $R^1$ is methoxy-substituted C1-4 alkyl. In preferred embodiments of these compounds, $R^1$ is 2-methoxy-2-propyl.

In compounds of Formula II, $R^3$ can contain a substituted pyrrolidinyl; for example, it can represent —(CH$_2$)$_{1-2}$-substituted pyrrolidinyl such as a ((3R,4R)-4-fluoropyrrolidin-3-yl)methyl group. The pyrrolidinyl can be attached at any position of the ring, typically at a carbon atom and preferably at position 3 when counting the ring nitrogen atom as position 1. The pyrrolidinyl group can be substituted with groups such as halo, lower alkyl and lower alkoxy. Preferably, the pyrrolidinyl ring is substituted by at least one halo on a ring carbon atom, generally F; in addition, it is optionally substituted by lower alkyl, typically Me or Et, and optionally the lower alkyl is on N.

In preferred embodiments of any of the above-described compounds of Formula II, $R^3$ represents —CH$_2$—CH$_2$—CH(NH$_2$)—CH$_2$F such as

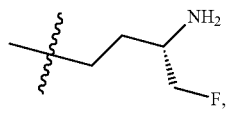

or —(CH$_2$)$_{1-2}$-substituted pyrrolidinyl, wherein the group —(CH$_2$)$_{1-2}$-substituted pyrrolidinyl can be, for example:

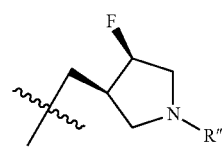

wherein R" is H, Me, Et, isopropyl, or n-propyl. Preferably, the pyrrolidinyl group has the absolute stereochemical configuration shown here, i.e., it is a ((3R,4R)-4-fluoropyrrolidin-3-yl)methyl group wherein R" is H, Me, Et, isopropyl or n-propyl.

In preferred embodiments of the compounds of Formula II, $R^4$ is selected from —C(O)—CH(CH$_3$)—OH,

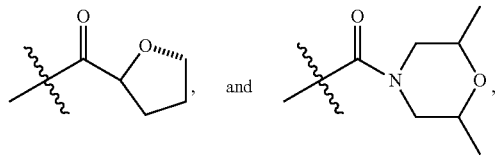

In particularly preferred embodiments of these compounds, $R^4$ is selected from:

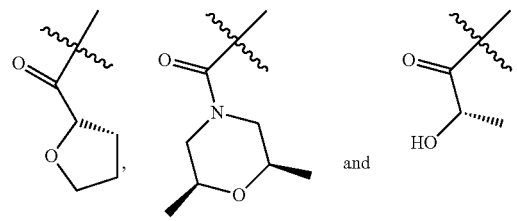

Also preferably in these compounds, $R^5$ represents

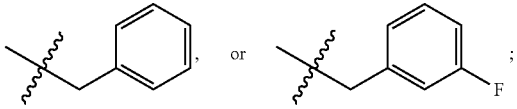 [SMILES: *Cc1ccccc1 ; *Cc1cccc(F)c1]

and in some such embodiments, $R^6$ is

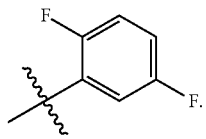 [SMILES: *c1cc(F)ccc1F]

A particularly preferred embodiment of the present invention provides a compound of Formula I or II selected from:

N—((R)-1-(3-(2,5-difluorophenyl)-1-(3-fluorobenzyl)-1H-1,2,4-triazol-5-yl)-2,2-dimethylpropyl)-N-(((3R,4R)-4-fluoropyrrolidin-3-yl)methyl)-2,6-dimethylmorpholine-4-carboxamide;

N—((R)-1-(1-benzyl-3-(2,5-difluorophenyl)-1H-1,2,4-triazol-5-yl)-2,2-dimethylpropyl)-N-(((3R,4R)-4-fluoropyrrolidin-3-yl)methyl)-2,6-dimethylmorpholine-4-carboxamide;

(S)—N—((R)-1-(1-benzyl-3-(2,5-difluorophenyl)-1H-1,2,4-triazol-5-yl)-2,2-dimethylpropyl)-N-(((3R,4R)-4-fluoropyrrolidin-3-yl)methyl)tetrahydrofuran-2-carboxamide;

(S)—N—((R)-1-(3-(2,5-difluorophenyl)-1-(3-fluorobenzyl)-1H-1,2,4-triazol-5-yl)-2,2-dimethylpropyl)-N-(((3R,4R)-4-fluoropyrrolidin-3-yl)methyl)tetrahydrofuran-2-carboxamide;

(S)—N—((R)-1-(3-(2,5-difluorophenyl)-1-(3-fluorobenzyl)-1H-1,2,4-triazol-5-yl)-2,2-dimethylpropyl)-N-(((3R,4R)-4-fluoropyrrolidin-3-yl)methyl)-2-hydroxypropanamide; and (S)—N—((R)-1-(1-benzyl-3-(2,5-difluorophenyl)-1H-1,2,4-triazol-5-yl)-2,2-dimethylpropyl)-N-(((3R,4R)-4-fluoropyrrolidin-3-yl)methyl)-2-hydroxypropanamide.

Another particularly preferred embodiment of the present invention provides a compound of Formula I or II selected from:

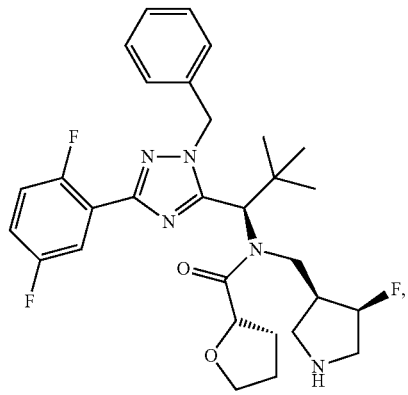

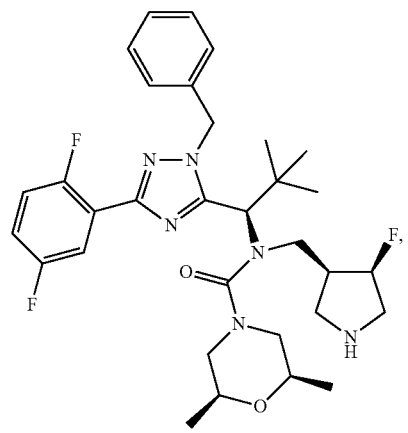

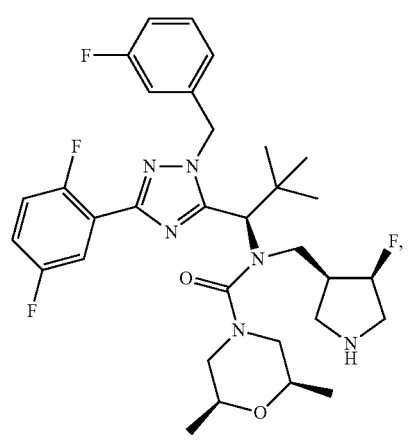

-continued

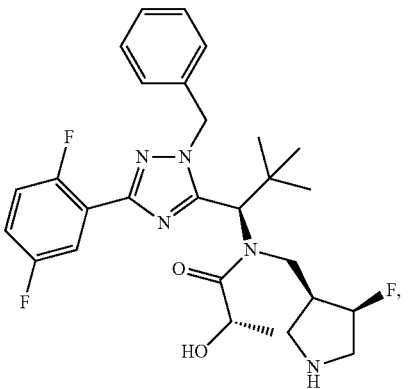

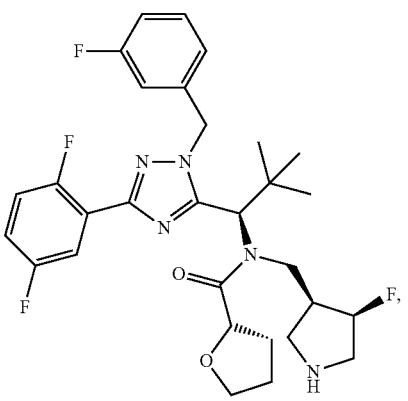

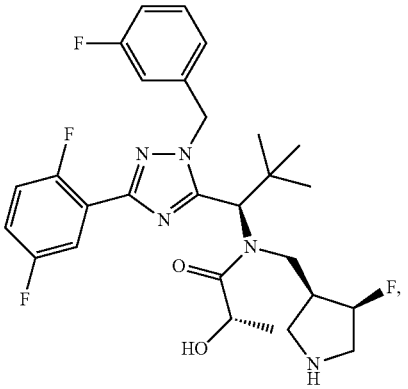

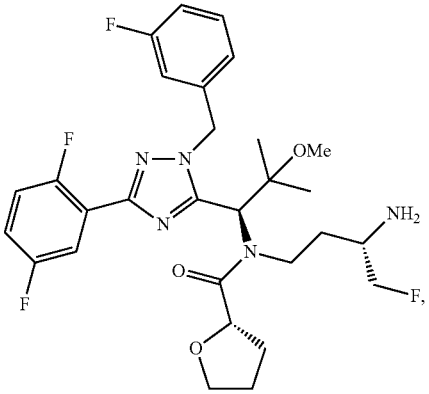

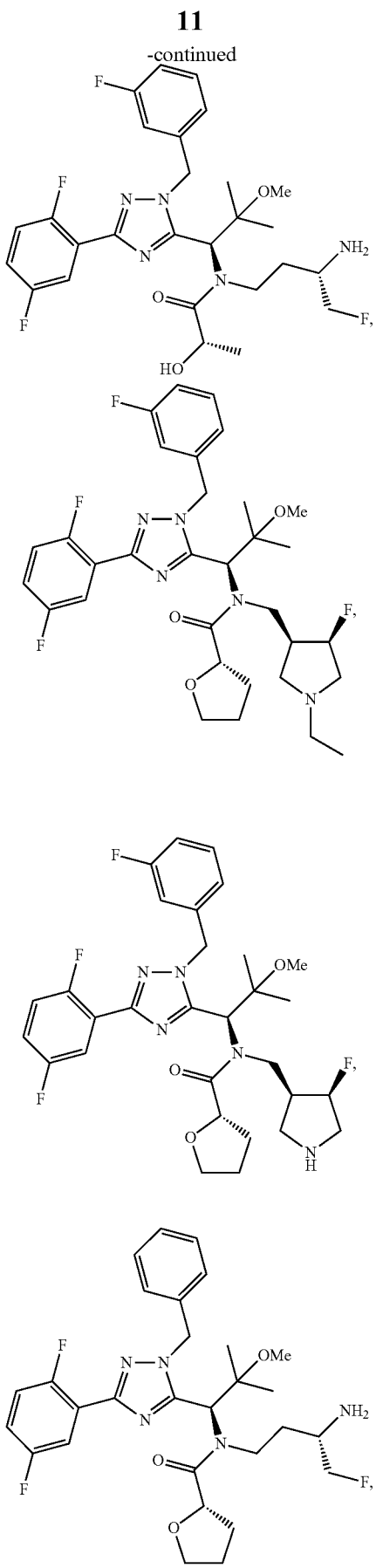

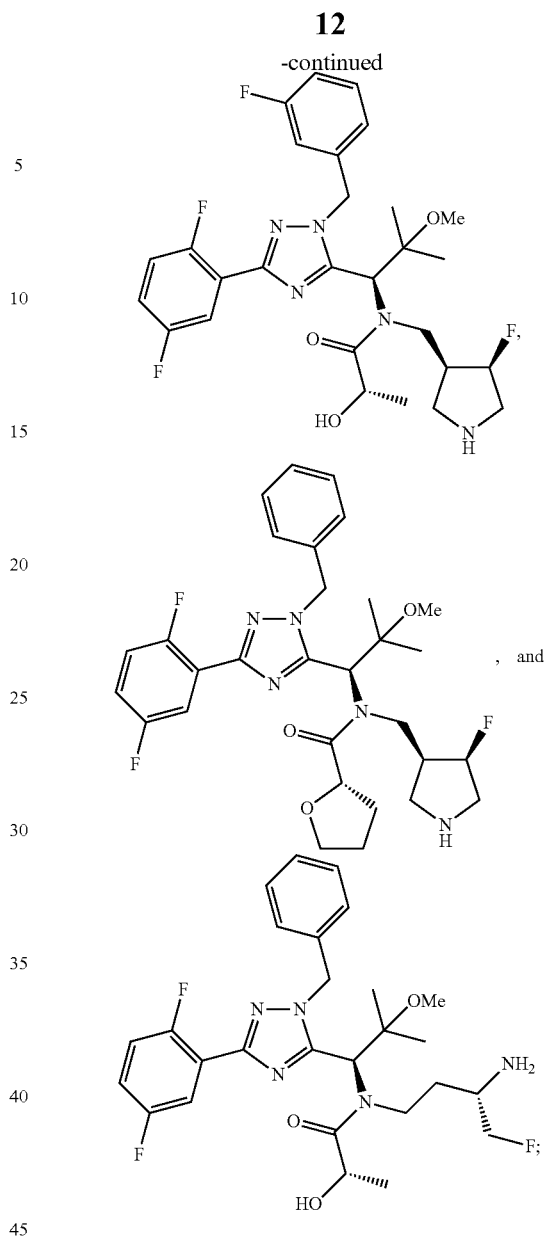

and the pharmaceutically acceptable salts of these compounds.

Another aspect of the present invention provides a pharmaceutical composition comprising a therapeutically effective amount of a compound of Formula I or II, including any of the embodiments of these compounds disclosed above, and a pharmaceutically acceptable carrier. A preferred embodiment of this aspect of the invention provides a composition further comprising at least one additional agent for the treatment of cancer. Provided in a further preferred embodiment is a composition wherein the additional agent for the treatment of cancer is selected from the group consisting of irinotecan, topotecan, gemcitabine, imatinib, trastuzumab, 5-fluorouracil, leucovorin, carboplatin, cisplatin, docetaxel, paclitaxel, tezacitabine, cyclophosphamide, vinca alkaloids, anthracyclines, rituximab, and trastuzumab.

Provided in yet another aspect of the present invention is a method of treating a disorder mediated, at least in part, by KSP in a mammalian patient comprising administering to a mammalian patient in need of such treatment a therapeutically effective amount of a composition of comprising a compound of Formula I or II including any of the embodiments of these compounds disclosed above. A preferred embodiment provides method of treating a disorder mediated, at least in part, by KSP in a mammalian patient comprising administering to a mammalian patient in need of such treatment a therapeutically effective amount of a composition comprising a compound of any of the embodiments of the compounds of Formula I or II described above, and at least one additional agent for the treatment of cancer. A preferred embodiment of this aspect of the invention provides a method of treating a disorder mediated, at least in part, by KSP in a mammalian patient wherein the disorder is a cellular proliferative disease; preferably the cellular proliferative disease is cancer.

A further preferred embodiment of this aspect of the invention provides a method of treating a cellular proliferative disease as disclosed above, wherein the cellular proliferative disease is cancer selected from a group consisting of lung and bronchus; prostate; breast; pancreas; colon and rectum; thyroid; stomach; liver and intrahepatic bile duct; kidney and renal pelvis; urinary bladder; uterine corpus; uterine cervix; ovary; multiple myeloma; esophagus; acute myelogenous leukemia; chronic myelogenous leukemia; lymphocytic leukemia; myeloid leukemia; brain; oral cavity and pharynx; larynx; small intestine; non-Hodgkin lymphoma; melanoma; and villous colon adenoma.

Yet another preferred embodiment of this aspect of the invention provides a method wherein the additional agent for the treatment of cancer is selected from the group consisting of irinotecan, topotecan, gemcitabine, imatinib, trastuzumab, 5-fluorouracil, leucovorin, carboplatin, cisplatin, docetaxel, paclitaxel, tezacitabine, cyclophosphamide, vinca alkaloids, anthracyclines, rituximab, and trastuzumab.

A particularly preferred embodiment of the present aspect provides a method for inhibiting KSP in a mammalian patient, wherein said method comprises administering to the patient an effective KSP-inhibiting amount of a compound of Formula I or II according to any of the embodiments described herein. In some embodiments, the method employs a compound of Formula I or II as described above; for example, a compound of Formula I wherein:

$R^1$ is selected from $C_{1-6}$ straight chain alkyl, $C_{3-6}$ branched alkyl, and —$C_{3-6}$ cyclo alkyl;

$R^2$ is selected from H, and $C_{1-6}$ straight chain alkyl;

$R^3$ represents —$(CH_2)_{0-3}$ substituted or unsubstituted pyrrolidinyl;

$R^4$ is selected from —C(O)—$CH_2$OH, —C(O)-tetrahydrofuranyl, —C(O)—CH($CH_3$)—OH, —C(O)-unsubstituted morpholinyl, and —C(O)-morpholinyl substituted with up to three alkyl groups;

$R^5$ is selected from substituted or unsubstituted benzyl, wherein the substituents are selected from Cl, F, Br, and I; and $R^6$ is selected from phenyl substituted with up to three halogen atoms.

The patient for such methods is generally a human, and typically has been diagnosed as being in need of such treatment prior to initiating these methods.

Another preferred embodiment provides a method comprising administering to the patient an effective KSP-inhibiting amount of a compound of Formula I or II according to any of the embodiments described above. In some embodiments, the method uses a compound of Formula I wherein:

$R^1$ is selected from $C_{3-6}$ branched alkyl;

$R^2$ represents H;

$R^3$ represents —$(CH_2)_{1-3}$-substituted pyrrolidinyl;

$R^4$ is selected from —C(O)-tetrahydrofuranyl, —C(O)—CH($CH_3$)—OH, —C(O)-morpholinyl substituted with up to three alkyl groups;

$R^5$ represents benzyl, or benzyl substituted with at least two fluoro atoms; and $R^6$ is selected from phenyl substituted with up to two halogen atoms.

A further particularly preferred embodiment provides a method comprising administering a compound of Formula I, wherein:

$R^1$ represents t-butyl;

$R^3$ represents —$(CH_2)$-fluoro-pyrrolidinyl;

$R^4$ is selected from —C(O)-tetrahydrofuranyl, —C(O)—CH($CH_3$)—OH, —C(O)-2,6-dimethyl morpholinyl;

$R^5$ represents benzyl, or benzyl substituted with one fluoro atom; and $R^6$ is selected from phenyl substituted with up to two fluoro atoms.

A further preferred embodiment provides a method comprising administering a compound of Formula II, wherein:

$R^1$ represents 2-methoxy-2-propyl;

$R^3$ represents —$(CH_2)$-fluoro-pyrrolidinyl or —$CH_2$—$CH_2$—CH($NH_2$)—$CH_2$F;

$R^4$ is selected from —C(O)-tetrahydrofuranyl, —C(O)—CH($CH_3$)—OH, —C(O)-2,6-dimethyl morpholinyl;

$R^5$ represents benzyl, or benzyl substituted with one fluoro atom; and $R^6$ is selected from phenyl substituted with up to two fluoro atoms.

Yet another particularly preferred embodiment provides a method of administering a compound of Formula I or II to treat conditions such as cancer. The method can use a compound according to any of the above-described embodiments, including a compound of Formula I or II, wherein:

$R^3$ represents

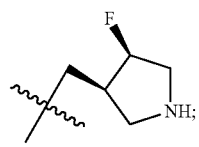 [SMILES: *C[C@@H]1CNC[C@@H]1F]

$R^4$ is selected from —C(O)—CH($CH_3$)—OH,

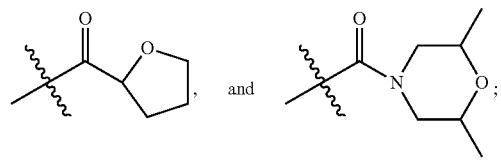 [SMILES: *C(=O)C1CCCO1 ; *C(=O)N1CC(C)OC(C)C1]

$R^5$ represents

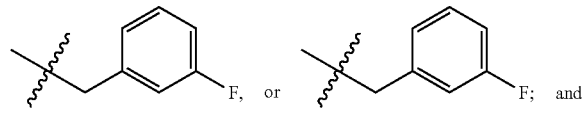 [SMILES: *Cc1cccc(F)c1 ; *Cc1cccc(F)c1 ; "and"]

$R^6$ is

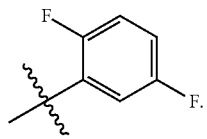 [SMILES: *c1cc(F)ccc1F]

A specifically preferred embodiment of the methods of treatment described above provides a method for inhibiting KSP in a mammalian patient, wherein said method comprises administering to the patient an effective KSP-inhibiting amount of a compound of Formula I selected from:

N—((R)-1-(3-(2,5-difluorophenyl)-1-(3-fluorobenzyl)-1H-1,2,4-triazol-5-yl)-2,2-dimethylpropyl)-N-(((3R,4R)-4-fluoropyrrolidin-3-yl)methyl)-2,6-dimethylmorpholine-4-carboxamide;

N—((R)-1-(1-benzyl-3-(2,5-difluorophenyl)-1H-1,2,4-triazol-5-yl)-2,2-dimethylpropyl)-N-(((3R,4R)-4-fluoropyrrolidin-3-yl)methyl)-2,6-dimethylmorpholine-4-carboxamide;

(S)—N—((R)-1-(1-benzyl-3-(2,5-difluorophenyl)-1H-1,2,4-triazol-5-yl)-2,2-dimethylpropyl)-N-(((3R,4R)-4-fluoropyrrolidin-3-yl)methyl)tetrahydrofuran-2-carboxamide;

(S)—N—((R)-1-(3-(2,5-difluorophenyl)-1-(3-fluorobenzyl)-1H-1,2,4-triazol-5-yl)-2,2-dimethylpropyl)-N-(((3R,4R)-4-fluoropyrrolidin-3-yl)methyl)tetrahydrofuran-2-carboxamide;

(S)—N—((R)-1-(3-(2,5-difluorophenyl)-1-(3-fluorobenzyl)-1H-1,2,4-triazol-5-yl)-2,2-dimethylpropyl)-N-(((3R,4R)-4-fluoropyrrolidin-3-yl)methyl)-2-hydroxypropanamide; and (S)—N—((R)-1-(1-benzyl-3-(2,5-difluorophenyl)-1H-1,2,4-triazol-5-yl)-2,2-dimethylpropyl)-N-(((3R,4R)-4-fluoropyrrolidin-3-yl)methyl)-2-hydroxypropanamide.

Another specifically preferred embodiment provides a method for inhibiting KSP in a mammalian patient, wherein said method comprises administering to the patient an effective KSP-inhibiting amount of a compound of Formula I or II selected from:

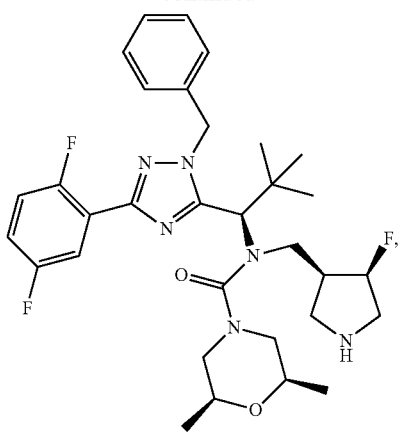

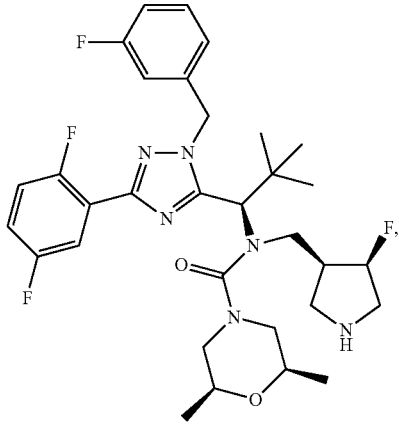

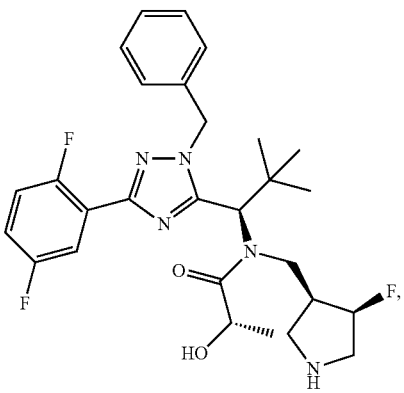

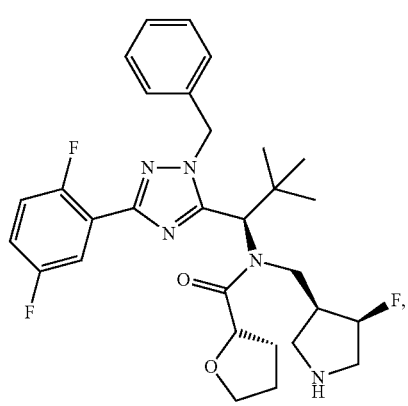

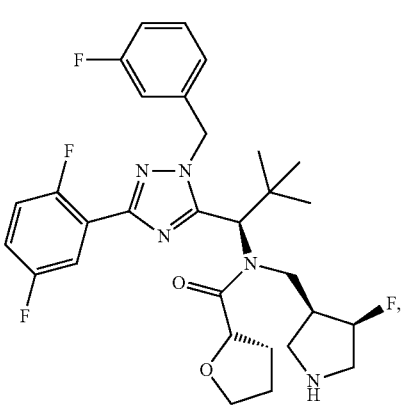

17
-continued
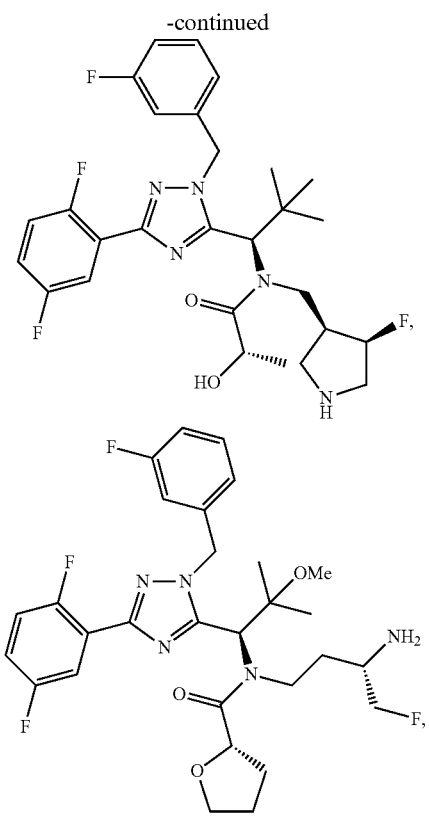
18
-continued
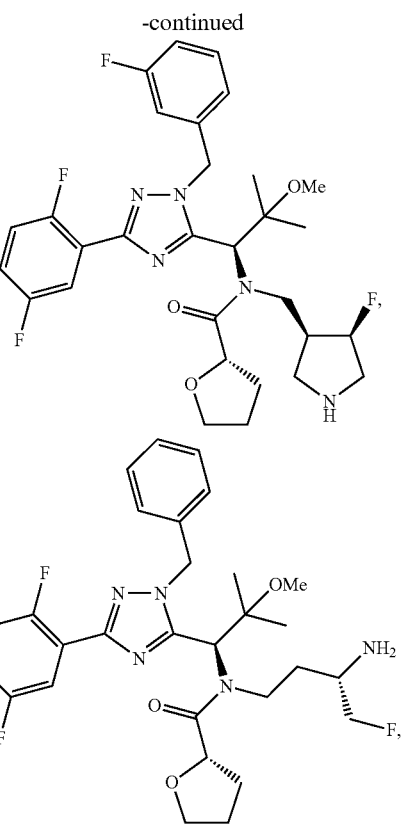
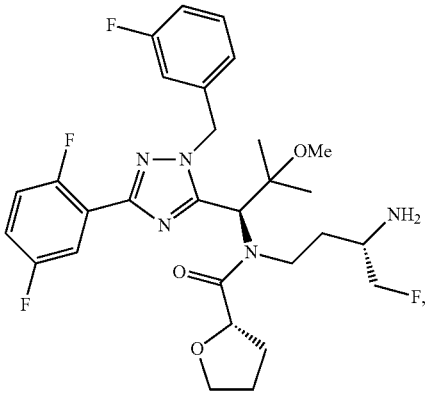
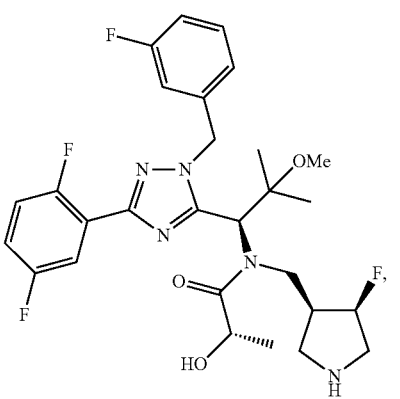
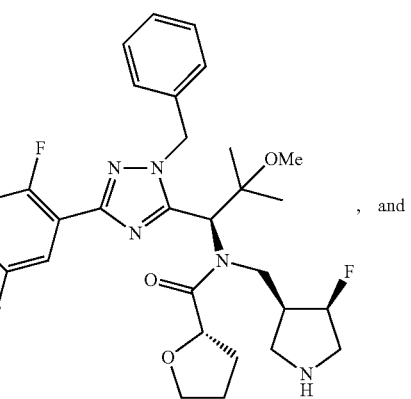
, and -continued

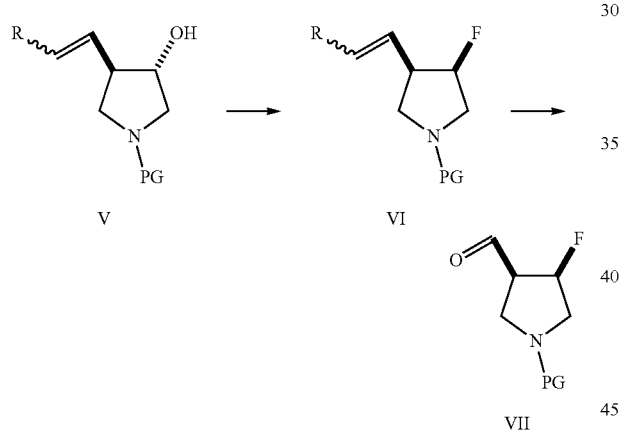

or a pharmaceutically acceptable salt of one of these compounds.

In another aspect, the invention provides a method to make certain compounds of Formula I or II and key intermediates for their synthesis. Scheme 2 herein depicts one such method for making a preferred pyrrolidine ring moiety for compounds such as those depicted above. The synthetic method for making this fluorinated pyrrolidine comprises fluorination of a trans-3,4-disubstituted pyrrolidine of Formula V to provide a cis-fluorinated vinyl pyrrolidine compound of Formula VI, and oxidizing the olefin of the compound of Formula VI to provide an aldehyde of Formula VII, as shown below:

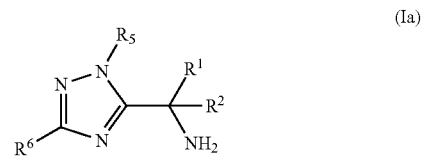

These transformations can be done on racemic compounds, or with optically active compounds; in some embodiments, the compounds of Formula V or VI or VII is optically active and has the absolute stereochemistry shown here, with an enantiomeric excess of at least 90%. In the compounds of Formulas V-VII, R is H or an optionally substituted C1-C6 alkyl or aryl, and PG represents a protecting group suitable for use on an aliphatic nitrogen atom. In some embodiments, R is H, and the compound of Formula V can be prepared from an epoxide of a protected 3-pyrroline (see compound 2.3 in Scheme 2) by reaction of the epoxide with a Grignard reagent, for example. The trans-hydroxy group of Formula V can be converted into the cis-fluoro group in Formula VI using any suitable reagent that provides an $S_N2$ exchange to achieve inversion of the chiral center. In some embodiments, this is accomplished using a fluoride source in an inert solvent, and a reagent that activates the hydroxyl to make it a suitable leaving group. For example a fluoride salt such as trialkylamine trihydrofluoride (e.g., $Et_3N$-trihydrofluoride) or HF-pyridine can be used in a suitable solvent inert to the reaction conditions along with an alkyl or aryl sulfonyl fluoride, such as C1-C6 perfluoralkyl sulfonyl fluoride to convert the hydroxyl to F with stereochemical inversion.

The vinylogous group in the compounds of Formula VI can be oxidized to an aldehyde using various conventional methods such as treatment with osmium tetroxide and sodium metaperiodate, or using ozone, to provide the compound of Formula VII. Methods for this transformation are known in the art.

The compound of Formula VII can then be incorporated into a compound of Formula I by various methods, including a reductive amination reaction as described herein; or various nucleophilic addition reactions known in the art for use with such aldehydes and nucleophilic carbon groups suitable for the desired target compound. In one embodiment, the compound of Formula VII is attached via reductive amination to a compound of Formula Ia as shown in Scheme 3 to provide a compound of Formula Ib as illustrated below. The compound of Formula Ia wherein $R^3$ is H is optionally protected if it includes a group such as a free amine or hydroxyl requiring protection.

Suitable protecting groups (PG) for use in these reactions and intermediates include amides (e.g., formamide, acetamide, trichloroacetamide) and carbamates (e.g., methyl, ethyl, trichloroethyl, t-butyl, or benzyl carbamate). The amides and carbamates are of general formula —C(O)-L-A, wherein L is a bond (for amides) or —O— (for carbamates), and A is an optionally substituted alkyl (C1-6 preferably) or aryl (preferably phenyl); or A can be H when L is a bond.

In some embodiments, this method further comprises reductive amination of the compound of Formula VII with a compound of Formula Ia:

(Ia)

wherein:
$R^1$ is selected from $C_{1-6}$alkoxy-$C_{1-4}$alkyl, $C_{1-6}$ straight chain alkyl, $C_{3-6}$ branched alkyl, and —$C_{3-6}$ cyclo alkyl;
$R^2$ is selected from H, and $C_{1-6}$ straight chain alkyl;
$R^5$ is selected from substituted or unsubstituted benzyl, wherein the substituents are selected from Cl, F, Br, and I; and
$R^6$ is selected from phenyl substituted with up to three halogen atoms;
to provide a compound of Formula Ib:

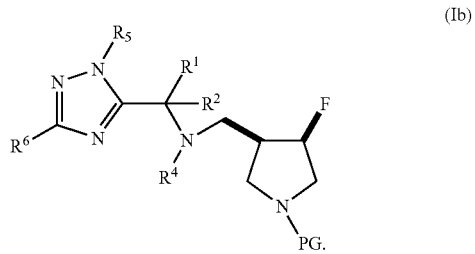

In some embodiments, any of the foregoing methods of synthesis further comprises synthesizing the compound of Formula V from an epoxide of Formula IV,

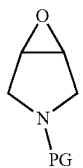

(IV)

by opening the epoxide with an organometallic reagent of the formula

wherein R is H or an optionally substituted alkyl or aryl group, and M is a metallic group selected from Li, MgX, and ZnX, where X is a halogen, to provide the compound of Formula V. For this step, a preferred organometallic reagent is:

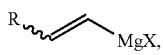

wherein X is Cl, Br or I.

The invention thus provides novel intermediates of Formula VI and VII as described above, as well as methods to use these intermediates for making compounds of Formula I or Ib.

The compounds used in and produced by these methods may be racemic, or any of the compounds having at least one chiral center can be separated into single enantiomers or single diastereomers as appropriate. In the present invention, it is sometimes preferably to separate the two enantiomers of the compound of Formula V or VI in order to use a single enantiomer for making compounds of Formula I or Ib. In some embodiments, the compound of Formula V or VI is made in racemic form, and is then separated by chiral chromatography or other conventional means to provide an optically active compound, preferably essentially free of its enantiomer. In a preferred embodiment, the compound of Formula V or VI is optically active and is of the specific absolute stereochemistry depicted herein. In some such embodiments, it is essentially free of the opposite enantiomer.

Representative Compounds of the Invention

Specific compounds within the scope of this invention are exemplified in Table 1 in the Experimental section.

B. Definitions and Overview

As discussed above, the present invention is directed in part to new substituted triazole compounds.

It is to be understood that the terminology used herein is for the purpose of describing particular embodiments only and is not intended to limit the scope of the present invention. It must be noted that as used herein and in the claims, the singular forms "a," and "the" include plural referents unless the context clearly dictates otherwise. In this specification and in the claims which follow, reference will be made to a number of terms which shall be defined to have the following meanings:

As used herein, "alkyl" or "straight chain alkyl" refers to monovalent saturated aliphatic hydrocarbyl groups having from 1 to 6 carbon atoms and more preferably 1 to 3 carbon atoms. This term is exemplified by groups such as methyl, ethyl, n-propyl, n-pentyl and the like.

The term "branched alkyl" as used herein refers to a monovalent saturated branched alkyl group having from 3 to 6 carbon atoms. This term is exemplified by groups such as i-butyl, i-propyl, t-butyl, and the like.

"Cyclo alkyl" refers to a alkyl group having from 3 to 6 carbon atoms and wherein three or more carbon atoms are connected to each other so as to form a cycli structure. Illustrative examples include cyclo propyl, cyclo butyl, cyclo pentyl, and cyclo hexyl group.

"Alkoxyalkyl" as used herein refers to an alkyl group that is substituted with at least one alkoxy group. If not otherwise described, the alkoxyalkyl group comprises up to 10 carbon atoms in the alkoxy group, and up to 10 carbon atoms in the alkyl group. It attaches to the base molecule through the alkyl group. In some instances, these groups are described according to the number of carbon atoms in the alkoxy group and/or in the alkyl group, such as for example $C_{1-6}$ alkoxy-$C_{1-4}$-alkyl, which refers to an alkyl group having 1-4 carbon atoms, which is substituted with a C1-C6 alkoxy group. Suitable alkoxyalkyl groups include methoxymethyl; methoxyethyl; ethoxymethyl; ethoxyethyl; methoxypropyl; and methoxyisopropyl (2-methoxy-2-propyl).

"Halo" or "halogen" refers to fluoro, chloro, bromo and/or iodo and preferably is fluoro or chloro.

"Biological activity" as used herein refers to an inhibition concentration when tested in at least one of the assays outlined in any of Examples 12-14 and as defined in at least one example thereof.

As used herein, the term "pharmaceutically acceptable salts" refers to the nontoxic acid or alkaline earth metal salts of the compounds of Formula (I) or (II). These salts can be prepared in situ during the final isolation and purification of the compounds of Formula (I) and (II) or by separately reacting the base or acid functions with a suitable organic or inorganic acid or base, respectively. Representative salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemi-sulfate, heptanoate, hexanoate, fumarate, hydrochloride, hydrobromide, hydroiodide, 2-hydroxyethanesulfonate, lactate, maleate, methanesulfonate, nicotinate, 2-napth-alenesulfonate, oxalate, pamoate, pectinate, persulfate, 3-phenylproionate, picrate, pivalate, propionate, succinate, sulfate, tartrate, thiocyanate, p-toluenesulfonate and undecanoate. Also, the basic nitrogen-containing groups can be quaternized with such agents as alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to form pharmaceutically acceptable acid addition salts include such inorganic acids as hydrochloric acid, sulfuric acid and phosphoric acid and such organic acids as oxalic acid, maleic acid, methanesulfonic acid, succinic acid and citric acid. Basic addition salts can be prepared in situ during the final isolation and purification of the compounds of Formula (I) or (II) or separately by reacting carboxylic acid moieties with a suitable base such as the hydroxide, carbonate or bicarbonate of a pharmaceutically acceptable metal cation or with ammonia, or an organic primary, secondary or tertiary amine Pharmaceutically acceptable salts include, but are not limited to, cations based on the alkali and alkaline earth metals, such as sodium, lithium, potassium, calcium, magnesium, aluminum salts and the like, as well as ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like.

As used herein, the term "pharmaceutically acceptable ester" refers to esters which hydrolyze in vivo and include those that break down in the human body to leave the parent compound, a salt thereof, or a pharmaceutically active metabolite. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Representative examples of particular esters include, but are not limited to, formates, acetates, propionates, butyrates, acrylates and ethylsuccinates.

The term "pharmaceutically acceptable prodrug" as used herein refers to those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound or a pharmaceutically active metabolite of the above formula, for example by hydrolysis in blood. A discussion is provided in T. Higuchi and V. Stella, PRO-DRUGS AS NOVEL DELIVERY SYSTEMS, Vol. 14 of the A.C.S. Symposium Series, and in Edward B. Roche, ed., BIOREVERSIBLE CARRIERS IN DRUG DESIGN, American Pharmaceutical Association and Pergamon Press, 1987, both of which are incorporated herein by reference.

As used herein "anticancer agents" or "agent for the treatment of cancer" refers to agents that include, by way of example only, agents that induce apoptosis; polynucleotides (e.g., ribozymes); polypeptides (e.g., enzymes); drugs; biological mimetics; alkaloids; alkylating agents; antitumor antibiotics; antimetabolites; hormones; platinum compounds; monoclonal antibodies conjugated with anticancer drugs, toxins, and/or radionuclides; biological response modifiers (e.g. interferons and interleukins, etc.); adoptive immunotherapy agents; hematopoietic growth factors; agents that induce tumor cell differentiation (e.g. all-trans-retinoic acid, etc.); gene therapy reagents; antisense therapy reagents and nucleotides; tumor vaccines; inhibitors of angiogenesis, and the like. Numerous other agents are well within the purview of one of skill in the art.

It is understood that in all substituted groups defined above, polymers arrived at by defining substituents with further substituents to themselves are not intended for inclusion herein. In such cases, the maximum number of such substituents is three. For example, serial substitutions of substituted aryl groups with two other substituted aryl groups are limited to -substituted aryl-(substituted aryl)-substituted aryl.

Similarly, it is understood that the above definitions are not intended to include impermissible substitution patterns (e.g., methyl substituted with 5 fluoro groups or a hydroxy group alpha to ethenylic or acetylenic unsaturation). Such impermissible substitution patterns are well known to the skilled artisan.

Compounds of this invention may exhibit stereoisomerism by virtue of the presence of one or more asymmetric or chiral centers in the compounds. The present invention contemplates the various stereoisomers and mixtures thereof. Certain of the compounds of the invention comprise asymmetrically substituted carbon atoms. Such asymmetrically substituted carbon atoms can result in the compounds of the invention comprising mixtures of stereoisomers at a particular asymmetrically substituted carbon atom or a single stereoisomer. As a result, racemic mixtures, mixtures of diastereomers, single enantiomer, as well as single diastereomers of the compounds of the invention are included in the present invention. The terms "S" and "R" configuration, as used herein, are as defined by the IUPAC 1974 "RECOMMENDATIONS FOR SECTION E, FUNDAMENTAL STEREOCHEMISTRY," Pure Appl. Chem. 45:13-30, 1976. Desired enantiomers can be obtained by chiral synthesis from commercially available chiral starting materials by methods well known in the art, or may be obtained from mixtures of the enantiomers by separating the desired enantiomer by using known techniques.

Compounds of this invention may also exhibit geometrical isomerism. Geometrical isomers include the cis and trans forms of compounds of the invention having alkenyl or alkenylenyl moieties. The present invention comprises the individual geometrical isomers and stereoisomers and mixtures thereof.

C. Compound Preparation

The compounds of this invention can be prepared from readily available starting materials using the following general methods and procedures. Unless otherwise indicated, the starting materials are commercially available and well known in the art. It will be appreciated that where typical or preferred process conditions (i.e., reaction temperatures, times, mole ratios of reactants, solvents, pressures) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and P. G. M. Wuts, Protecting Groups in Organic Synthesis, Second Edition, Wiley, New York, 1991, and references cited therein.

Furthermore, the compounds of this invention may contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

Compounds of the invention can be prepared by methods known in the art and further described herein. For example, methods for making compounds of formula (I) are described in published application PCT/US2007/084154 (WO 2008/063912). Examples of additional synthesis methods applicable to the preparation of compounds of formula (I) are provided herein.

An example of the preparation of certain KSP inhibitors of Formula I is shown below in Scheme 1.

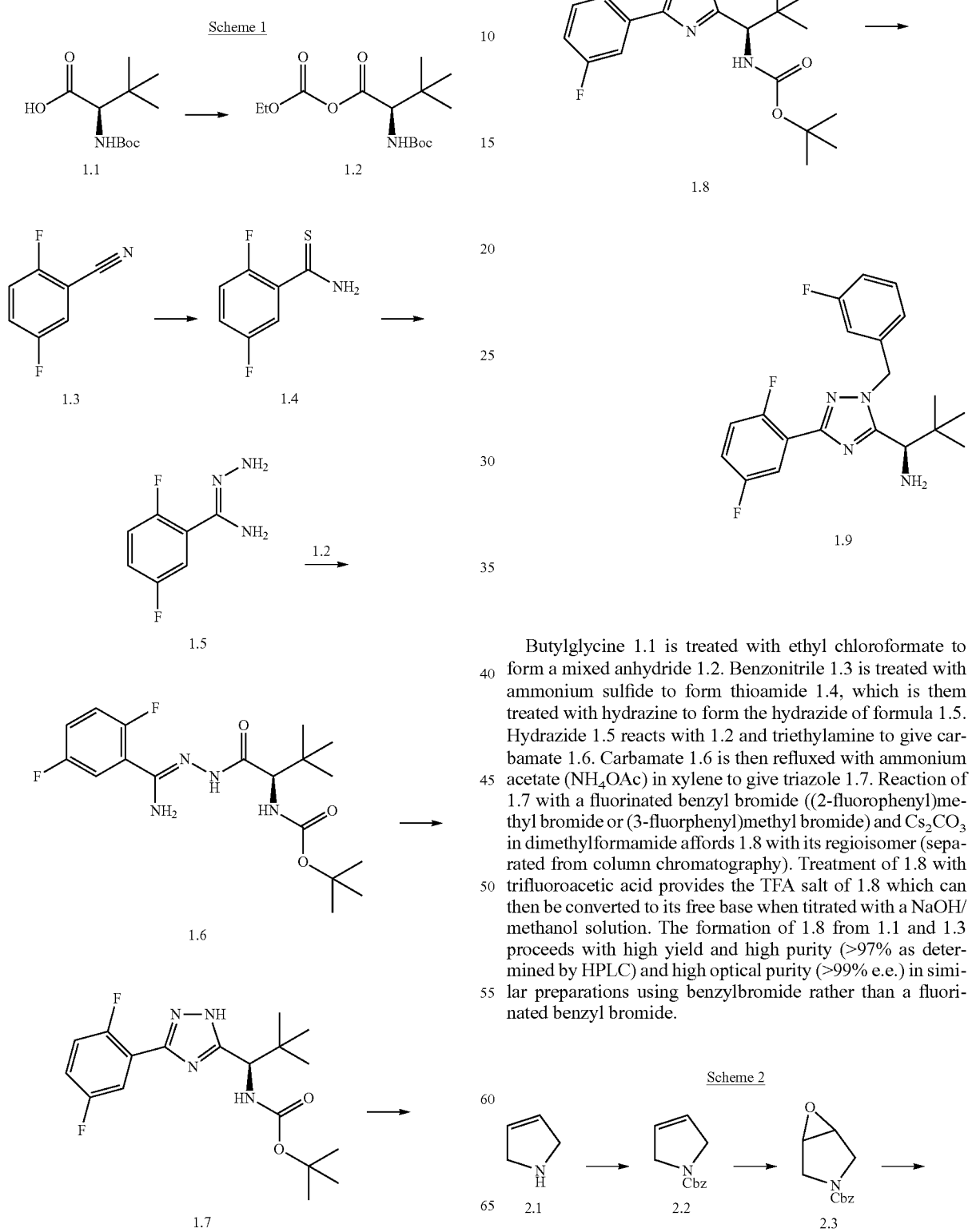

Butylglycine 1.1 is treated with ethyl chloroformate to form a mixed anhydride 1.2. Benzonitrile 1.3 is treated with ammonium sulfide to form thioamide 1.4, which is them treated with hydrazine to form the hydrazide of formula 1.5. Hydrazide 1.5 reacts with 1.2 and triethylamine to give carbamate 1.6. Carbamate 1.6 is then refluxed with ammonium acetate (NH$_4$OAc) in xylene to give triazole 1.7. Reaction of 1.7 with a fluorinated benzyl bromide ((2-fluorophenyl)methyl bromide or (3-fluorphenyl)methyl bromide) and Cs$_2$CO$_3$ in dimethylformamide affords 1.8 with its regioisomer (separated from column chromatography). Treatment of 1.8 with trifluoroacetic acid provides the TFA salt of 1.8 which can then be converted to its free base when titrated with a NaOH/methanol solution. The formation of 1.8 from 1.1 and 1.3 proceeds with high yield and high purity (>97% as determined by HPLC) and high optical purity (>99% e.e.) in similar preparations using benzylbromide rather than a fluorinated benzyl bromide.

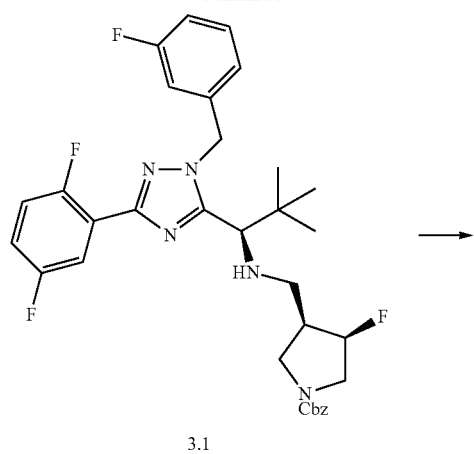

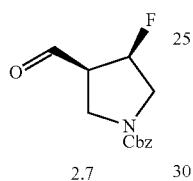

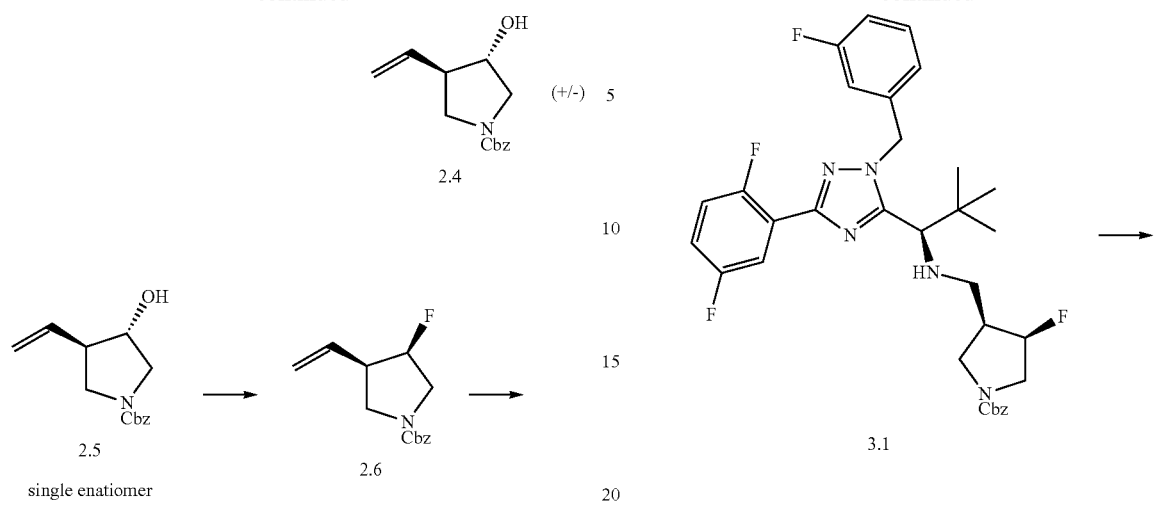

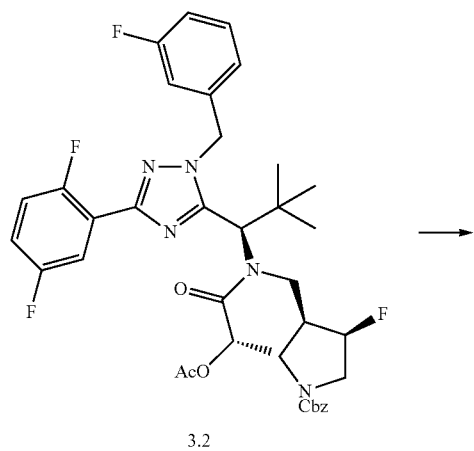

Compound 1.9 can be reacted with aldehyde 2.7 under reductive amination conditions to give secondary amine 3.1, which can then be acylated to provide compounds of formula (I). Scheme 2 illustrates the preparation of aldehyde 2.7 that can be used in the reductive amination step to prepare compounds of formula I, particularly compounds of formula Ia. Cyclic amine 2.1 is protected with Cbz group to give compound 2.2. Epoxide 2.3 is obtained from MCPBA epoxidation of compound 2.2. Epoxide gives racemic mixture of alcohol 2.4 by reacting vinylmagnesium bromide and copper bromide. Alcohol 2.5 as a single enantiomer is obtained by chiral column chromatography. Alcohol 2.5 is subjected to a fluorination condition to give vinyl fluoropyrrolidine 2.6. Vinyl fluoropyrrolidine 2.6 undergoes subsequent dihydroxylation/oxidative cleavage to give aldehyde 2.7.

Scheme 3

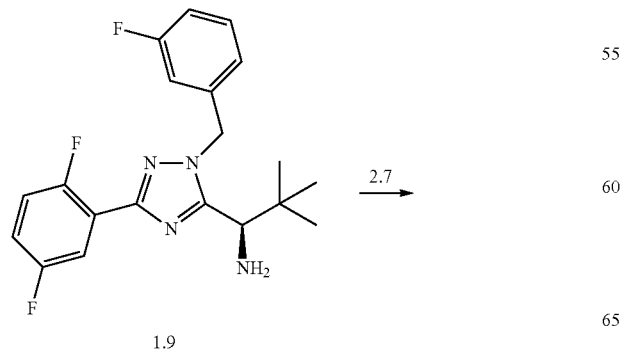

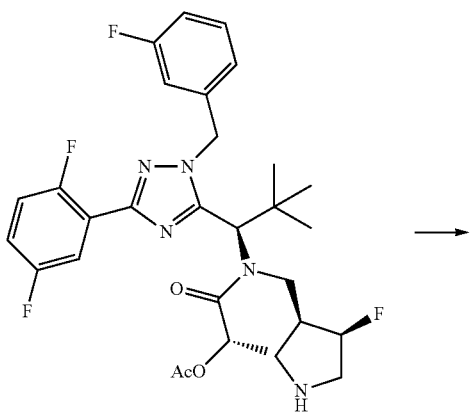

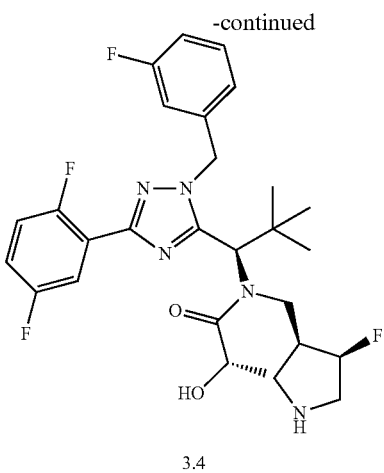

3.4

After the attachment of the fluoropyrrolidine moiety, known acylating agents and conditions are used to acylate the acyclic amine to provide compounds of formula (I), after which a protecting group on the nitrogen of the pyrrolidine ring and/or a protecting group of the acylating moiety is deprotected. Scheme 3 illustrates the reductive amination to provide secondary amine 3.1. Acylation of the amine 3.1 followed by deprotection of the Cbz group and removal of a protecting group on the free hydroxyl group provides compound 3.4. Suitable protective groups for the pyrrolidine ring nitrogen, for example, benzyl carbamates that can be removed by hydrogenolysis and t-butyl carbamates that can be selectively removed with reagents such as trimethylsilyl iodide or acid.

Scheme 4

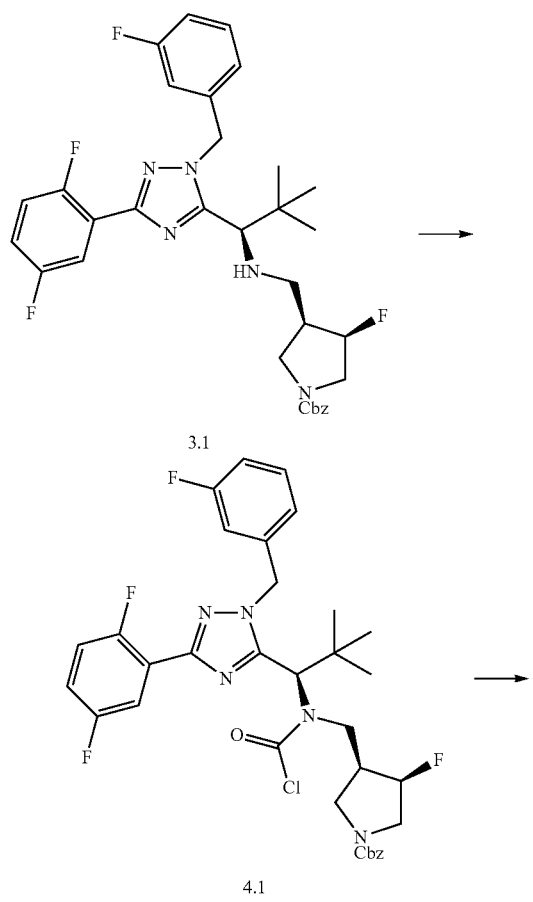

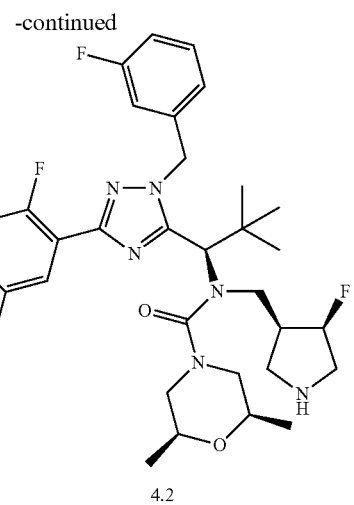

4.2

Scheme 4 represents general description for urea formation from secondary amine 3.1. Secondary amine 3.1 reacts phosgene or triphosgene to give chlorocompound 4.1, which directly reacts with amine to give urea compounds of formular (I), after which a protecting group on the nitrogen of the pyrrolidine ring is deprotected. Scheme 4 illustrated the chlorocarbonylation of secondary amine 3.1 to give compound 4.1, which immediately reacts with morpholine followed by removal of Cbz group to give compound 4.2.

Note that the absolute stereochemistry of the chiral centers in this molecule is identified based on the chirality of known starting materials or intermediates. HPLC and nmr data support the conclusion that the above process provides the compound as a single isomer.

Suitable acylating agents and acids for the acylation step include acyl halides, anhydrides, and acids having the appropriate structures (see formula I). Suitable amide coupling conditions include use of a variety of amide coupling reagents to form the amide bond, such as the carbodiimides N—N'-dicyclohexylcarbodiimide (DCC), N—N'-diisopropylcarbodiimide (DIPCDI), and 1-ethyl-3-(3'-dimethylaminopropyl)carbodiimide (EDCI). The carbodiimides may be used in conjunction with additives such as dimethylaminopyridine (DMAP) or benzotriazoles such as 7-aza-1-hydroxybenzotriazole (HOAt), 1-hydroxybenzotriazole (HOBt), and 6-chloro-1-hydroxybenzotriazole (Cl-HOBt); conditions for such amide bond formations are well known in the art.

Additional amide coupling reagents also include aminium and phosphonium based reagents. Aminium salts include N-[(dimethylamino)-1H-1,2,3-triazolo[4,5-b]pyridine-1-ylmethylene]-N-methylmethanaminium hexafluorophosphate N-oxide (HATU), N-[(1H-benzotriazol-1-yl)(dimethylamino)methylene]-N-methylmethanaminium hexafluorophosphate N-oxide (HBTU), N-[(1H-6-chlorobenzotriazol-1-yl)(dimethylamino)methylene]-N-methylmethanaminium hexafluorophosphate N-oxide (HCTU), N-[(1H-benzotriazol-1-yl)(dimethylamino)methylene]-N-methylmethanaminium tetrafluoroborate N-oxide (TBTU), and N-[(1H-6-chlorobenzotriazol-1-yl)(dimethylamino)methylene]-N-methylmethanaminium tetrafluoroborate N-oxide (TCTU). Phosphonium salts include benzotriazole-1-yl-oxy-tris-(dimethylamino)-phosphonium hexafluorophosphate (BOP), 7-azabenzotriazol-1-yl-N-oxy-tris(pyrrolidino)phosphonium hexafluorophosphate (PyAOP) and benzotriazol-1-yl-N-oxy-tris(pyrrolidino) phosphonium hexafluorophosphate (PyBOP).

The amide formation step may be conducted in a polar solvent such as dimethylformamide (DMF) and may also include an organic base such as diisopropylethylamine (DIEA) or dimethylaminopyridine (DMAP).

The following compounds in Table 1 were prepared by using one of the methods outlined above. Table I also provides IC50 values for the various examples.

D. Pharmaceutical Formulations

When employed as pharmaceuticals, the compounds of the subject invention are usually administered in the form of pharmaceutical compositions. These compositions can be administered by a variety of routes including oral, parenteral, transdermal, topical, rectal, and intranasal. These compounds are effective, for example, as both injectable and oral compositions. Such compositions are prepared in a manner well known in the pharmaceutical art and comprise at least one active compound.

This invention also includes pharmaceutical compositions which contain, as the active ingredient, one or more of the compounds of the subject invention above associated with pharmaceutically acceptable carriers. In making the compositions of this invention, the active ingredient is usually mixed with an excipient, diluted by an excipient or enclosed within such a carrier which can be in the form of a capsule, sachet, paper or other container. The excipient employed is typically an excipient suitable for administration to human subjects or other mammals. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g., about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The quantity of active component, that is the compound according to the subject invention, in the pharmaceutical composition and unit dosage form thereof may be varied or adjusted widely depending upon the particular application, the potency of the particular compound and the desired concentration.

The compositions are preferably formulated in a unit dosage form, each dosage containing from about 1 to about 500 mg, usually about 5 to about 100 mg, occasionally about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Preferably, the compound of the subject invention above is employed at no more than about 20 weight percent of the pharmaceutical composition, more preferably no more than about 15 weight percent, with the balance being pharmaceutically inert carrier(s).

The active compound is effective over a wide dosage range and is generally administered in a pharmaceutically or therapeutically effective amount. It will be understood, however, that the amount of the compound actually administered will be determined by a physician, in the light of the relevant circumstances, including the condition to be treated, the severity of the condition being treated, the chosen route of administration, the actual compound administered, the age, weight, and response of the individual patient, the severity of the patient's symptoms, and the like.

In therapeutic use for treating, or combating, cancer in mammals, the compounds or pharmaceutical compositions thereof will be administered by any appropriate route, such as orally, topically, transdermally, and/or parenterally at a dosage to obtain and maintain a concentration, that is, an amount, or blood-level of active component in the mammal undergoing treatment that will be therapeutically effective. Generally, such therapeutically effective amount of dosage of active component (i.e., an effective dosage) will be in the range of about 0.1 to about 100, more preferably about 1.0 to about 50 mg/kg of body weight/day.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices which deliver the formulation in an appropriate manner.

The following formulation examples illustrate representative pharmaceutical compositions of the present invention.

FORMULATION EXAMPLE 1

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules in 340 mg quantities.

FORMULATION EXAMPLE 2

A tablet formula is prepared using the ingredients below:

| Ingredient | Quantity (mg/tablet) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

FORMULATION EXAMPLE 3

A dry powder inhaler formulation is prepared containing the following components:

| Ingredient | Weight % |
|---|---|
| Active Ingredient | 5 |
| Lactose | 95 |

The active ingredient is mixed with the lactose and the mixture is added to a dry powder inhaling appliance.

FORMULATION EXAMPLE 4

Tablets, each containing 30 mg of active ingredient, are prepared as follows

| Ingredient | Quantity (mg/tablet) |
|---|---|
| Active Ingredient | 30.0 mg |
| Starch | 45.0 mg |
| Macrocrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

FORMULATION EXAMPLE 5

Capsules, each containing 40 mg of medicament are made as follows:

| Ingredient | Quantity (mg/capsule) |
|---|---|
| Active Ingredient | 40.0 mg |
| Starch | 109.0 mg |
| Magnesium stearate | 1.0 mg |
| Total | 150.0 mg |

The active ingredient, starch and magnesium stearate are blended, passed through a No. 20 mesh U.S. sieve, and filled into hard gelatin capsules in 150 mg quantities.

FORMULATION EXAMPLE 6

Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

FORMULATION EXAMPLE 7

Suspensions, each containing 50 mg of medicament per 5.0 mL dose are made as follows:

| Ingredient | Amount |
|---|---|
| Active Ingredient | 50.0 mg |
| Xanthan gum | 4.0 mg |
| Sodium carboxymethyl cellulose (11%)/ Macrocrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

FORMULATION EXAMPLE 8

| Ingredient | Quantity (mg/capsule) |
|---|---|
| Active Ingredient | 15.0 mg |
| Starch | 407.0 mg |
| Magnesium stearate | 3.0 mg |
| Total | 425.0 mg |

The active ingredient, starch, and magnesium stearate are blended, passed through a No. 20 mesh U.S. sieve, and filled into hard gelatin capsules in 425.0 mg quantities.

FORMULATION EXAMPLE 9

A subcutaneous formulation may be prepared as follows:

| Ingredient | Quantity |
|---|---|
| Active Ingredient | 5.0 mg |
| Corn Oil | 1.0 mL |

FORMULATION EXAMPLE 10

A topical formulation may be prepared as follows:

| Ingredient | Quantity |
|---|---|
| Active Ingredient | 1-10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

FORMULATION EXAMPLE 11

An illustrative example of an intravenous formulation may be prepared as follows:

| Ingredient | Quantity |
|---|---|
| Active Ingredient | 250 mg |
| Isotonic saline | 1000 mL |

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472 which is herein incorporated by reference.

Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

Other suitable formulations for use in the present invention can be found in Remington's Pharmaceutical Sciences, Mack Publishing Company, Philadelphia, Pa., 17th ed. (1985).

E. Dosage and Administration

As noted above, the compounds described herein are suitable for use in a variety of drug delivery systems described above. Additionally, in order to enhance the in vivo serum half-life of the administered compound, the compounds may be encapsulated, introduced into the lumen of liposomes, prepared as a colloid, or other conventional techniques may be employed which provide an extended serum half-life of the compounds. A variety of methods are available for preparing liposomes, as described in, e.g., Szoka, et al., U.S. Pat. Nos. 4,235,871, 4,501,728 and 4,837,028 each of which is incorporated herein by reference.

Compounds of the instant invention are useful for inhibiting or treating a disorder mediated, at least in part, by the activity of KSP. In one aspect, the disorder that is mediated, at least in part by KSP, is a cellular proliferative disorder. The term "cellular proliferative disorder" or "cell proliferative disorder" refers to diseases including, for example, cancer, tumor, hyperplasia, restenosis, cardiac hypertrophy, immune disorder and inflammation. The present invention provides methods of treating a human or mammalian subject in need of such treatment, comprising administering to the subject a therapeutically effective amount of a compound of formula I or II, either alone or in combination with other anticancer agents.

The compounds of the invention are useful in vitro or in vivo in inhibiting the growth of cancer cells. The term "cancer" refers to cancer diseases including, for example, lung and bronchus; prostate; breast; pancreas; colon and rectum; thyroid; stomach; liver and intrahepatic bile duct; kidney and renal pelvis; urinary bladder; uterine corpus; uterine cervix; ovary; multiple myeloma; esophagus; acute myelogenous leukemia; chronic myelogenous leukemia; lymphocytic leukemia; myeloid leukemia; brain; oral cavity and pharynx; larynx; small intestine; non-hodgkin lymphoma; melanoma; and villous colon adenoma.

Cancer also includes tumors or neoplasms selected from the group consisting of carcinomas, adenocarcinomas, sarcomas, and hematological malignancies.

Additionally, the type of cancer can be selected from the group consisting of growth of solid tumors/malignancies, myxoid and round cell carcinoma, locally advanced tumors, human soft tissue carcinoma, cancer metastases, squamous cell carcinoma, esophageal squamous cell carcinoma, oral carcinoma, cutaneous T cell lymphoma, Hodgkin's lymphoma, non-Hodgkin's lymphoma, cancer of the adrenal cortex, ACTH-producing tumors, nonsmall cell cancers, breast cancer, gastrointestinal cancers, urological cancers, malignancies of the female genital tract, malignancies of the male genital tract, kidney cancer, brain cancer, bone cancers, skin cancers, thyroid cancer, retinoblastoma, neuroblastoma, peritoneal effusion, malignant pleural effusion, mesothelioma, Wilms's tumors, gall bladder cancer, trophoblastic neoplasms, hemangiopericytoma, and Kaposi's sarcoma.

A compound or composition of this invention may be administered to a mammal by a suitable route, such as orally, intravenously, parenterally, transdermally, topically, rectally, or intranasally.

Mammals include, for example, humans and other primates, pet or companion animals, such as dogs and cats, laboratory animals, such as rats, mice and rabbits, and farm animals, such as horses, pigs, sheep, and cattle.

Tumors or neoplasms include growths of tissue cells in which the multiplication of the cells is uncontrolled and progressive. Some such growths are benign, but others are termed "malignant" and can lead to death of the organism. Malignant neoplasms or "cancers" are distinguished from benign growths in that, in addition to exhibiting aggressive cellular proliferation, they can invade surrounding tissues and metastasize. Moreover, malignant neoplasms are characterized in that they show a greater loss of differentiation (greater "dedifferentiation") and organization relative to one another and to surrounding tissues. This property is called "anaplasia."

Compounds having the desired biological activity may be modified as necessary to provide desired properties such as improved pharmacological properties (e.g., in vivo stability, bio-availability), or the ability to be detected in diagnostic applications. Stability can be assayed in a variety of ways such as by measuring the half-life of the compounds during incubation with peptidases or human plasma or serum.

For diagnostic purposes, a wide variety of labels may be linked to the compounds, which may provide, directly or indirectly, a detectable signal. Thus, the compounds and/or compositions of the subject invention may be modified in a variety of ways for a variety of end purposes while still retaining biological activity. In addition, various reactive sites may be introduced for linking to particles, solid substrates, macromolecules, and the like.

Labeled compounds can be used in a variety of in vivo or in vitro applications. A wide variety of labels may be employed, such as radionuclides (e.g., gamma-emitting radioisotopes such as technetium-99 or indium-111), fluorescers (e.g., fluorescein), enzymes, enzyme substrates, enzyme cofactors, enzyme inhibitors, chemiluminescent compounds, bioluminescent compounds, and the like. Those of ordinary skill in the art will know of other suitable labels for binding to the complexes, or will be able to ascertain such using routine experimentation. The binding of these labels is achieved using standard techniques common to those of ordinary skill in the art.

Pharmaceutical compositions of the invention are suitable for use in a variety of drug delivery systems. Suitable formulations for use in the present invention are found in Remington's Pharmaceutical Sciences, Mack Publishing Company, Philadelphia, Pa., 17th ed. (1985).

The amount administered to the patient will vary depending upon what is being administered, the purpose of the administration, such as prophylaxis or therapy, the state of the patient, the manner of administration, and the like. In therapeutic applications, compositions are administered to a patient already suffering from a disease in an amount sufficient to cure or at least partially arrest the progression or symptoms of the disease and its complications. An amount adequate to accomplish this is defined as "therapeutically effective dose." Amounts effective for this use will depend on the disease condition being treated as well as by the judgment of the attending clinician depending upon factors such as the severity of the disease, disorder or condition, the age, weight and general condition of the patient, and the like.

The compounds administered to a patient are typically in the form of pharmaceutical compositions described above. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the compound preparations typically will be between about 3 and 11, more preferably from about 5 to 9 and most preferably from about 7 to 8. It will be understood that use of certain of the foregoing excipients, carriers, or stabilizers will result in the formation of pharmaceutical salts.

The therapeutic dosage of the compounds and/or compositions of the present invention will vary according to, for example, the particular use for which the treatment is made, the manner of administration of the compound, the health and condition of the patient, and the judgment of the prescribing physician. For example, for oral administration, the dose will typically be in the range of about 5 µg to about 50 mg per kilogram body weight per day, preferably about 1 mg to about 10 mg per kilogram body weight per day. In the alternative, for intravenous administration, the dose will typically be in the range of about 5 µg to about 50 mg per kilogram body weight, preferably about 500 µg to about 5000 µg per kilogram body weight. Alternative routes of administration contemplated include, but are not limited to, intranasal, transdermal, inhaled, subcutaneous and intramuscular. Effective doses can be extrapolated from dose-response curves derived from in vitro or animal model test systems.

In general, the compounds and/or compositions of the subject invention will be administered in a therapeutically effective amount by any of the accepted modes of administration for agents that serve similar utilities. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound and/or composition used in the method of the invention, the therapeutically effective dose can be estimated initially from cell culture assays. A dose may be formulated in animal models to achieve a circulating plasma concentration range which includes the $IC_{50}$ (the concentration of the test compound which achieves a half-maximal inhibition of activity) as determined in cell culture. Such information can be used to more accurately determine useful doses in humans. Levels in plasma may be measured, for example, by high performance liquid chromatography.

The following synthetic and biological examples are offered to illustrate this invention and are not to be construed in any way as limiting the scope of this invention.

EXAMPLES

Referring to the examples that follow, compounds of the present invention were synthesized using the methods described herein, or other methods, which are well known in the art. It is understood that compounds not prepared or analyzed may be prepared or analyzed using the methods described herein, or other methods, which are well known in the art.

The compounds and/or intermediates were characterized by high performance liquid chromatography (HPLC) using a Waters Millenium chromatography system with a 2690 Separation Module (Milford, Mass.). The analytical columns were Alltima C-18 reversed phase, 4.6×250 mm from Alltech (Deerfield, Ill.). A gradient elution was used, typically starting with 5% acetonitrile/95% water and progressing to 100% acetonitrile over a period of 40 minutes. All solvents contained 0.1% trifluoroacetic acid (TFA). Compounds were detected by ultraviolet light (UV) absorption at either 220 or 254 nm. HPLC solvents were from Burdick and Jackson (Muskegan, Mich.), or Fisher Scientific (Pittsburgh, Pa.). In some instances, purity was assessed by thin layer chromatography (TLC) using glass or plastic backed silica gel plates, such as, for example, Baker-Flex Silica Gel 1B2-F flexible sheets. TLC results were readily detected visually under ultraviolet light, or by employing well known iodine vapor and other various staining techniques.

Mass spectrometric analysis was performed on one of two LC/MS instruments: a Waters System (Alliance HT HPLC and a Micromass ZQ mass spectrometer; Column: Eclipse XDB-C18, 2.1×50 mm; solvent system: 5-95% (or 35-95%, or 65-95% or 95-95%) acetonitrile in water with 0.05% TFA; flow rate 0.8 mL/min; molecular weight range 500-1500; cone Voltage 20 V; column temperature 40° C.) or a Hewlett Packard System (Series 1100 HPLC; Column: Eclipse XDB-C18, 2.1×50 mm; solvent system: 1-95% acetonitrile in water with 0.05% TFA; flow rate 0.4 mL/min; molecular weight range 150-850; cone Voltage 50 V; column temperature 30° C.). All masses were reported as those of the protonated parent ions.

GC/MS analysis is performed on a Hewlett Packard instrument (HP6890 Series gas chromatograph with a Mass Selective Detector 5973; injector volume: 1 mL; initial column temperature: 50° C.; final column temperature: 250° C.; ramp time: 20 minutes; gas flow rate: 1 mL/min; column: 5% phenyl methyl siloxane, Model No. HP 190915-443, dimensions: 30.0 m×25 m×0.25 m).

Nuclear magnetic resonance (NMR) analysis was performed on some of the compounds with a Varian 300 MHz NMR (Palo Alto, Calif.). The spectral reference was either TMS or the known chemical shift of the solvent. Some compound samples were run at elevated temperatures (e.g., 75° C.) to promote increased sample solubility.

The purity of some of the invention compounds is assessed by elemental analysis (Desert Analytics, Tucson, Ariz.).

Melting points are determined on a Laboratory Devices Mel-Temp apparatus (Holliston, Mass.).

Preparative separations were carried out using a Flash 40 chromatography system and KP-Sil, 60A (Biotage, Charlottesville, Va.), or by flash column chromatography using silica gel (230-400 mesh) packing material, or by HPLC using a C-18 reversed phase column. Typical solvents employed for the Flash 40 Biotage system and flash column chromatography were dichloromethane, methanol, EtOAc, hexane, acetone, aqueous hydroxyamine and triethyl amine Typical solvents employed for the reverse phase HPLC were varying concentrations of acetonitrile and water with 0.1% trifluoroacetic acid.

Unless otherwise stated, all temperatures are in degrees Celsius. Also, in these examples and elsewhere, abbreviations have the following meanings:

| | |
|---|---|
| AcOH = | acetic acid |
| aq. = | aqueous |
| ATP = | adenosine triphosphate |
| Boc = | tert-butyloxycarbonyl |
| BSA = | bovine serum albumin |
| CAM = | ceric ammonium molybdate |
| DCM = | dichloromethane |
| DIAD = | diisopropyl azodicarboxylate |
| DIBAL = | diisobutylaluminum hydride |
| DIEA = | diisopropylethylamine |
| DIPEA = | diisopropylethylamine |
| DMAP = | dimethylaminopyridine |
| DMF = | dimethylformamide |
| DMSO = | dimethylsulfoxide |
| DTT = | dithiothreitol |
| eq. = | equivalents |
| Et2O = | diethyl ether |
| Et3N = | triethyl amine |
| EtOAc = | ethyl acetate |
| EtOH = | ethanol |
| g = | gram |
| h = | hour |
| HPLC = | high performance liquid chromatography |
| L = | liter |
| LC/MS = | liquid chromatography/mass spectroscopy |
| M = | molar |
| m = | meter |
| m/z = | mass/charge ratio |
| MeNH2 = | methyl amine |
| mg = | milligram |
| min = | minute |
| mL = | milliliter |
| mm = | millimeter |
| mM = | millimolar |
| mmol = | millimole |
| mol = | mole |

| | |
|---|---|
| N = | normal |
| nm = | nanometer |
| nM = | nanomolar |
| NMR = | nuclear magnetic resonance |
| PPh3 = | triphenyl phosphine |
| PhCF3 = | trifluoromethylbenzene |
| psi = | pounds per square inch |
| RT = | room temperature |
| sat. = | saturated |
| TEA = | triethylamine |
| THF = | tetrahydrofuran |
| TFA = | trifluoroacetic acid |
| TLC = | thin layer chromatography |
| TMS = | trimethylsilyl |
| TMSCl = | trimethylsilyl chloride |
| μg = | microgram |
| μL = | microliter |
| μM = | Micromolar |
| Uplc = | Ultra performance liquid chromatography |

Example 1

(S)—N—((R)-1-(1-benzyl-3-(2,5-difluorophenyl)-1H-1,2,4-triazol-5-yl)-2,2-dimethylpropyl)-N-(((3R,4R)-4-fluoropyrrolidin-3-yl)methyl)tetrahydrofuran-2-carboxamide

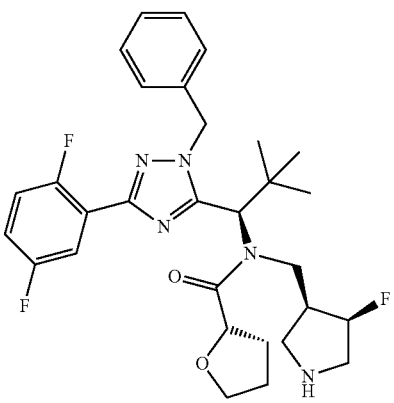

Procedure

Cbz Protection of 2,5-dihydro-1H-pyrrole

To a solution of 2,5-dihydro-1H-pyrrole (30 g, 434 mmol, 96% from Alfa Aesar) in dioxane (1000 mL, 0.43 M solution) was added CbzOSu (130 g, 521 mmol). After being stirred at room temperature for 18 h, the reaction mixture was concentrated to around 300 mL, diluted with 1000 mL of EtOAc. The organic layer was washed with water and brine, dried over anhydrous Na$_2$SO$_4$, filtered, and concentrated in vacuo. The desired benzyl 2,5-dihydro-1H-pyrrole-1-carboxylate was obtained in 91% yield (80.0 g) as a colorless oil by flash column chromatography. Rf=0.6 (30% EtOAc in hexanes).

$^1$H NMR (CDCl$_3$, 400 MHz): δ 7.32 (5H, m), 5.80 (2H, m), 5.77 (2H, s), 4.22 (4H, m). LC/MS (uplc): MH$^+$ 204.2, 160.1 (−44), 0.86 min.

Epoxidation of benzyl 2,5-dihydro-1H-pyrrole-1-carboxylate

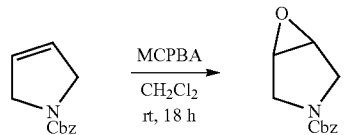 [SMILES: O=C(OCc1ccccc1)N1CC=CC1 ; O=C(OCc1ccccc1)N1CC2OC2C1]

To a solution of benzyl 2,5-dihydro-1H-pyrrole-1-carboxylate (33 g, 163 mmol; 90% from Aldrich) in dichloromethane (540 mL, 0.3 M solution) was added MCPBA (44 g, 340 mmol, 77% from Aldrich). After the reaction mixture was stirred at room temperature for 18 h, 500 mL of saturated Na$_2$CO$_3$ aqueous solution was added and the resulting mixture was stirred at room temperature for 1 h. The organic layer was separated, washed with water and brine, dried over anhydrous Na$_2$SO$_4$, filtered, and concentrated in vacuo. The desired product as a yellow oil was obtained in 83% yield (29.5 g) by flash column chromatography. $^1$H NMR (CDCl$_3$, 400 MHz): δ 3.38 (2H, m), 3.68 (2H, m), 3.87 (2H, m), 5.11 (2H, s), 7.33 (5H, m). LC/MS (uplc): MH$^+$ 220.0, 0.69 min.

Ring Opening of benzyl 6-oxa-3-azabicyclo[3.1.0]hexane-3-carboxylate

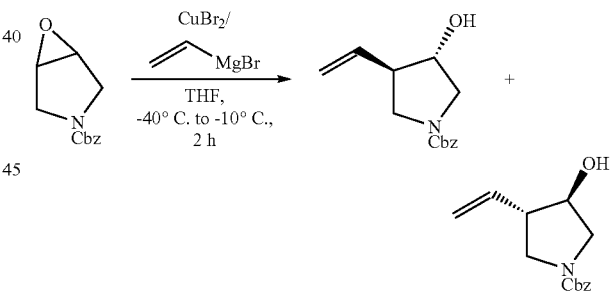

To a solution of benzyl 6-oxa-3-azabicyclo[3.1.0]hexane-3-carboxylate (28.5 g, 130 mmol) and CuBr.SMe$_2$ (26.7 g, 130 mmol) in anhydrous THF (260 mL, 0.5 M solution) at −40° C. was slowly added vinyl magnesium bromide (520 mL, 1.0 M solution in THF). The reaction mixture was then warmed up to −20° C. for 2 h. After quenched with saturated NH$_4$Cl aqueous solution (200 mL), the reaction mixture was extracted with EtOAc (500 mL). The organic layer was washed with water and brine, dried over anhydrous Na$_2$SO$_4$, filtered and concentrated in vacuo. The desired racemic mixture of trans-(±)-benzyl 3-hydroxy-4-vinylpyrrolidine-1-carboxylate was obtained in 48% yield (15.5 g) as a yellow oil by flash column chromatography. Rf=0.2 (30% EtOAc in hexanes). $^1$H NMR (CDCl$_3$, 400 MHz): δ 2.71 (1H, m), 3.28 (2H, m), 3.72 (2H, m), 4.11 (1H, m), 5.14 (2H, s), 5.16-5.23 (2H, m), 5.69 (1H, m), 7.33 (5H, m). LC/MS (uplc): MH⁺ 248.0, 0.78 min.

Resolution of trans-(±)-benzyl
3-hydroxy-4-vinylpyrrolidine-1-carboxylate

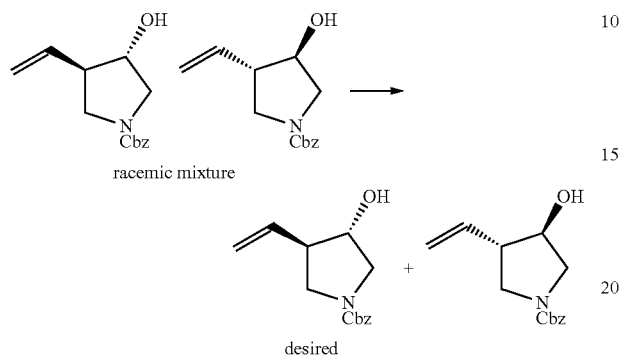

The racemic mixture of trans-(±)-benzyl 3-hydroxy-4-vinylpyrrolidine-1-carboxylate (14 g) was resolved by using chiral HPLC (Chiralpak AD-H Heptane:EtOH:MeOH, 8:1:1). The desired enantiomerically enriched (3S,4R)-benzyl 3-hydroxy-4-vinylpyrrolidine-1-carboxylate (6.7 min; 6.3 g, >99.5% ee) and undesired (3R,4S)-benzyl 3-hydroxy-4-vinylpyrrolidine-1-carboxylate (9.3 min; 6.7 g, 99.5% ee) were obtained with 92% recovery.

Fluorination of (3S,4R)-benzyl
3-hydroxy-4-vinylpyrrolidine-1-carboxylate

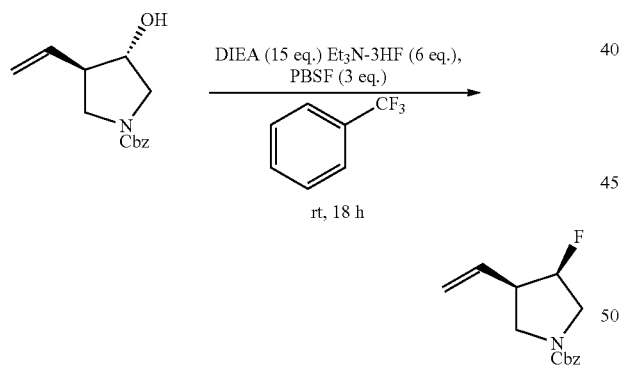

To a solution of (3S,4R)-benzyl 3-hydroxy-4-vinylpyrrolidine-1-carboxylate (5.0 g, 20.2 mmol) in PhCF₃ (81 mL, 0.25 M solution) was added N,N-diisopropylethylamine (53 mL, 303 mmol), triethylamine trihydrofluoride (19.8 mL, 121 mmol) and perfluoro-1-butanesulfonyl fluoride (PBSF, 3.6 mL, 20.2 mmol). The resulting mixture was stirred at room temperature. After 60 and 120 minutes, additional perfluoro-1-butanesulfonyl fluoride (3.6 mL, 20.2 mmol) was added. After 18 hours, the reaction mixture was transferred to a separatory funnel and was washed twice with 50 mL of 1.0 N HCl (Caution! lots of heat produced), twice with saturated NaHCO₃ aqueous solution, and once with H₂O and brine. The organic phase was dried over anhydrous Na₂SO₄, filtered and concentrated to provide a crude brown oil. The pure (3R,4R)-benzyl 3-fluoro-4-vinylpyrrolidine-1-carboxylate was obtained in 81% yield (4.1 g) as a yellow oil by flash column chromatography (SiO₂, 10%-30% EtOAc in hexanes). Rf=0.55 (30% EtOAc in hexanes). ¹H NMR (CDCl₃, 400 MHz): δ 7.37-7.25 (5H, m), 5.9 (1H, m), 5.24 (2H, m), 5.14 (2H, m), 5.03 (1H, dt, J=52.8, 3.2 Hz), 3.9-3.5 (3H, m), 3.53 (1H, m), 2.83 (1H, m). ¹³C NMR (CDCl₃, 100 MHz): δ 154.7, 154.6, 136.6, 131.89, 131.83, 128.48, 128.02, 127.94, 119.00, 118.94, 95.23, 94.47, 93.42, 92.67, 66.99, 66.94, 53.16, 52.94, 52.83, 52.60, 48.17, 48.02, 47.91, 47.83, 47.2, 47.1. LC/MS (uplc): MH⁺250.0, 0.93 min.

Oxidative Cleavage of Vinyl Fluoropyrrolidine

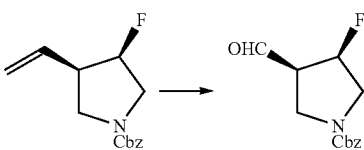 [SMILES: C=C[C@@H]1CN(C(=O)OCc2ccccc2)C[C@@H]1F ; O=C[C@@H]1CN(C(=O)OCc2ccccc2)C[C@@H]1F]

To a solution of (3R,4R)-benzyl 3-fluoro-4-vinylpyrrolidine-1-carboxylate (1.78 g, 7.15 mmol) in CH₃OH and H₂O (2:1, 30 mL, 0.2 M solution) was added a solution of OsO₄ in H₂O (3 mL of a 4% w/v solution, 0.5 mmol). NaIO₄ (4.6 g, 21.5 mmol) was then added in a single portion and the resulting mixture was stirred at room temperature. After 2 hours, the mixture was filtered to remove precipitated white solids and the filter cake was washed with EtOAc. The filtrate was concentrated in vacuo to remove the majority of the organic solvents. The residue was extracted with three portions of EtOAc and the combined organic layer was dried over anhydrous Na₂SO₄, filtered and concentrated. The crude (3R,4S)-benzyl 3-fluoro-4-formylpyrrolidine-1-carboxylate was used for the next step without further purification. LC/MS (uplc): MH⁺ 208.2 (−44), 252.0, 0.69 min.

Synthesis of 2,5-difluorobenzothioamide

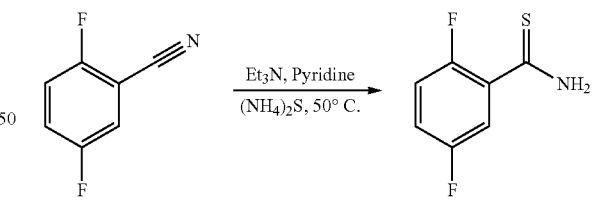

A stirred solution of 2,5-difluorobenzonitrile (25 g, 180 mmol) in pyridine (90 mL) was treated with 20 wt % ammonium sulfide in water (67.4 mL, 198 mmol) and triethylamine (27.4 mL, 198 mmol). The reaction mixture was stirred at 50° C. for 5 hr until the reaction was complete. After cooling to room temperature, the mixture was diluted with cold water and extracted with EtOAc. The organic layer was separated, then washed with H₂O (×3), brine (×3), then dried over anhydrous Na₂SO₄, filtered, and evaporated under reduced pressure to give the crude product. Purification on silica gel column (20% EtOAc in hexanes) to afford 2,5-difluorobenzothioamide as yellow solid (31.0 g, 99%). ¹H NMR (CDCl₃, 300 MHz): δ 7.12 (m, 2H), 7.90 (br, 2H), 8.08 (m, 1H). LC/MS (uplc): MH⁺174.0, 0.64 min.

Synthesis of 2,5-difluorobenzimidohydrazide

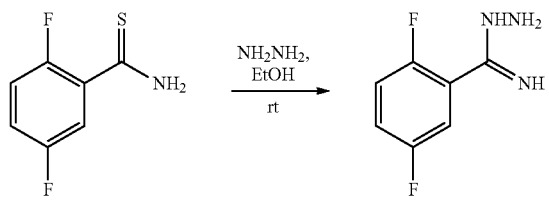 [SMILES: NC(=S)c1cc(F)ccc1F ; N=C(NN)c1cc(F)ccc1F]

To a stirred solution of 2,5-difluorobenzothioamide (22.5 g, 129.7 mmol) in EtOH (150 mL) was added hydrazine (6.1 mL, 194.5 mmol). After stirring at room temperature for 30 min, reaction was complete by LC/MS and white solid precipitated. The precipitate was filtered and washed with Hexanes to afford 2,5-difluorobenzimidohydrazide (5.52 g, 94%).

Acylation of 2,5-difluorobenzimidohydrazide

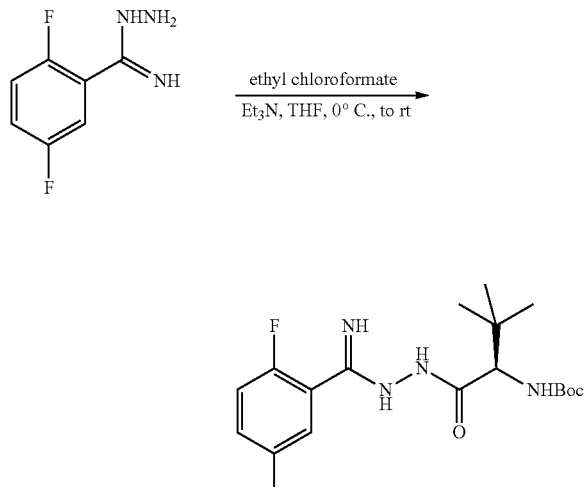

The N-Boc-D-tert-butylglycine (7.5 g, 32.4 mmol) was converted to a mixed anhydride by adding ethyl chloroformate (3.41 mL, 35.6 mmol), Et₃N (6.8 mL, 48.6 mmol) in anhydrous THF (65 mL, 0.5 M) at −5° C. to 0° C. The mixture was stirred at −5° C. for 30 min. The resulting solid was filtered off and additional anhydrous THF was added to wash the precipitate. The resulting reaction solution was then added to a THF solution of 2,5-difluorobenzimido-hydrazide (5.53 g, 32.4 mmol) at −5° C. Then the reaction was gradually warmed to room temperature and stirred for overnight. Once the reaction was complete, the mixture was partitioned between EtOAc and H₂O. The organic layer was separated and washed with H₂O, brine, then dried over anhydrous Na₂SO₄, filtered, and evaporated under reduced pressure to give the crude product, which was purified on silica gel column (50% EtOAc in Hexanes) to afford (R)-tert-butyl 1-(2-((2,5-difluorophenyl)(imino)methyl)hydrazinyl)-3,3-dimethyl-1-oxobutan-2-ylcarbamate (67%). Rf=0.4 (50% EtOAc in Hexanes). LC/MS (uplc): MH⁺ 385.3, 0.65 min.

Synthesis of (R)-tert-butyl 1-(3-(2,5-difluorophenyl)-1H-1,2,4-triazol-5-yl)-2,2-dimethylpropylcarbamate

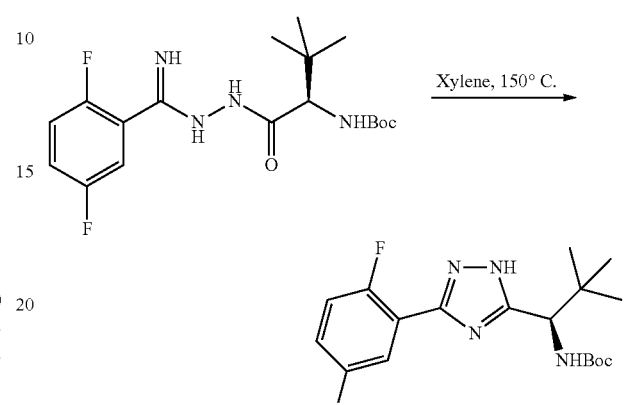

(R)-tert-Butyl 1-(2-((2,5-difluorophenyl)(imino)methyl)hydrazinyl)-3,3-dimethyl-1-oxobutan-2-ylcarbamate (8.35 g, 21.7 mmol) was dissolved in xylenes (200 mL). A Dean-Stark trap was equipped and the reaction mixture was heated to 150° C. Once the reaction was complete, the mixture was allowed to cool to room temperature, then partitioned between EtOAc and saturated aqueous NaHCO₃ solution. The organic layer was separated, then washed with saturated aqueous NaHCO₃ solution, H₂O, and brine, then dried over Na₂SO₄, filtered, and evaporated under reduced pressure to give (R)-tert-butyl 1-(3-(2,5-difluorophenyl)-1H-1,2,4-triazol-5-yl)-2,2-dimethylpropylcarbamate (7.81 g, 98%), which was used for the next step without further purification. LC/MS (uplc): MH⁺ 367.2, 0.98 min.

Alkylation of (R)-tert-butyl 1-(3-(2,5-difluorophenyl)-1H-1,2,4-triazol-5-yl)-2,2-dimethylpropylcarbamate with benzyl bromide

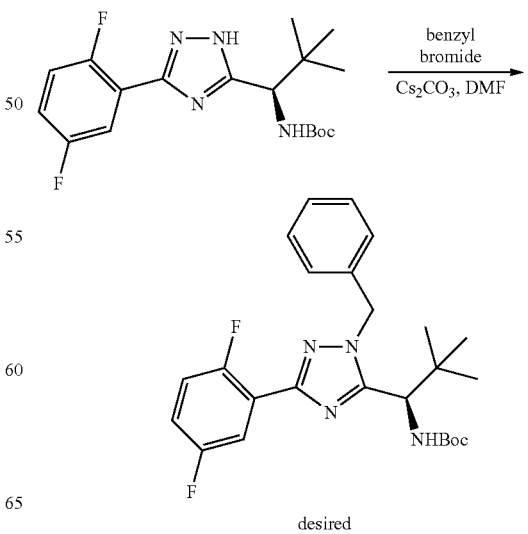

desired

47
-continued

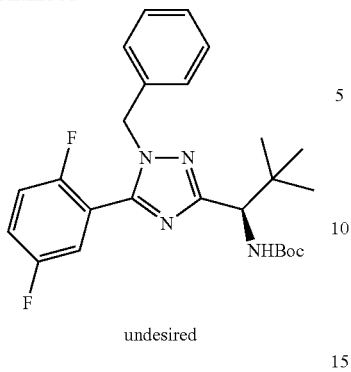

undesired

To a stirred suspension of (R)-tert-butyl 1-(3-(2,5-difluorophenyl)-1H-1,2,4-triazol-5-yl)-2,2-dimethylpropylcarbamate (5.89 g, 16.1 mmol) and Cs₂CO₃ (10.5 g, 32.2 mmol) in DMF (46 mL, 0.35 M) was added benzyl bromide (2.11 mL, 17.7 mmol). Once the organic layer was separated and washed with H₂O, brine, then dried over Na₂SO₄, filtered, and evaporated in vacuo to give (R)-tert-butyl 1-(1-benzyl-3-(2,5-difluorophenyl)-1H-1,2,4-triazol-5-yl)-2,2-dimethyl-propyl-carbamate. The desired regioisomer was obtained on silica gel column (0% to 100% EtOAc in Hexanes, 3.25 g, 44.3%). The structure was verified by ¹H NMR nOe experiments.

For the desired isomer, ((R)-tert-butyl 1-(1-benzyl-3-(2,5-difluorophenyl)-1H-1,2,4-triazol-5-yl)-2,2-dimethylpropyl-carbamate): crystals, LC/MS (uplc): MH⁺457.2, 1.36 min. ¹H NMR (CDCl₃, 300 MHz): δ 7.78 (m, 1H), 7.29-7.39 (m, 5H), 7.00-7.18 (m, 2H), 5.53 (s, 2H), 5.20 (d, 2H), 4.83 (m, 2H), 1.41 (s, 9H), 0.91 (s, 9H). For the undesired isomer, ((R)-tert-butyl 1-(1-benzyl-5-(2,5-difluorophenyl)-1H-1,2,4-triazol-3-yl)-2,2-dimethylpropylcarbamate): colorless oil, LC/MS (uplc): MH⁺ 457.2, 1.25 min. ¹H NMR (CDCl₃, 300 MHz): δ 7.25 (m, 5H), 7.15 (m, 2H), 7.05 (m, 1H), 5.45 (d, 2H), 5.28 (s, 2H), 4.85 (d, 2H), 1.43 (s, 9H), 0.97 (s, 9H).

Deprotection of (R)-tert-butyl 1-(1-benzyl-3-(2,5-difluorophenyl)-1H-1,2,4-triazol-5-yl)-2,2-dimethyl-propylcarbamate

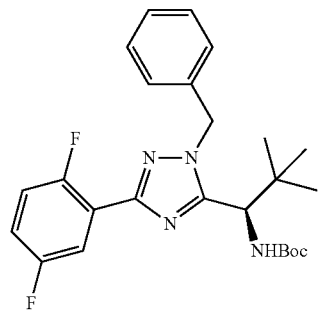

25% TFA in CH₂Cl₂
rt

48
-continued

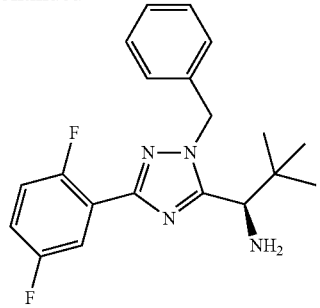

(R)-tert-Butyl 1-(1-benzyl-3-(2,5-difluorophenyl)-1H-1,2,4-triazol-5-yl)-2,2-dimethylpropylcarbamate (3.25 g, 7.13 mmol) was treated with TFA (10 mL) in CH₂Cl₂ (30 ml). Once the reaction was complete, the reaction was concentrated in vacuo and then partitioned between EtOAc and saturated aqueous NaHCO₃ solution. The organics were separated, then washed with H₂O, brine, then dried over Na₂SO₄, filtered, and evaporated under reduced pressure to give (R)-1-(1-benzyl-3-(2,5-difluorophenyl)-1H-1,2,4-triazol-5-yl)-2,2-dimethylpropan-1-amine which was directly used for the next step without further purification (2.32 g, 91%). LC/MS (uplc): MH⁺ 357.1, 0.82 min.

Reductive Alkylation

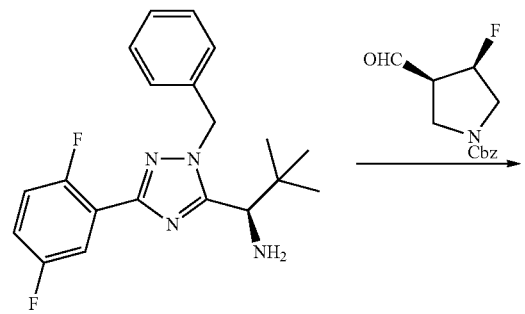

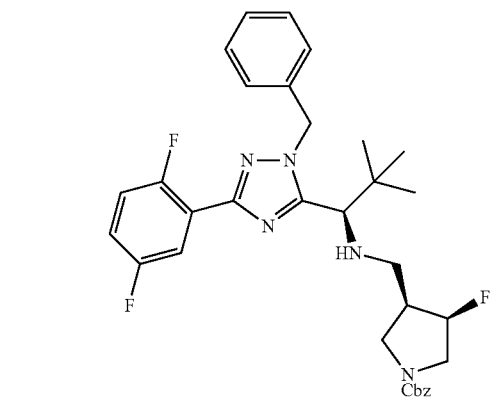

-continued

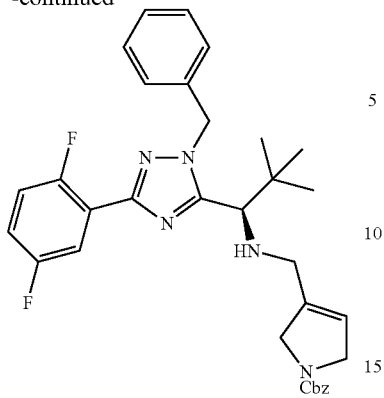

To a solution of (R)-1-(1-benzyl-3-(2,5-difluorophenyl)-1H-1,2,4-triazol-5-yl)-2,2-dimethylpropan-1-amine (2.55 g, 7.15 mmol) in CH$_2$Cl$_2$ (59 mL) was added the crude (3R,4S)-benzyl 3-fluoro-4-formylpyrrolidine-1-carboxylate (obtained from 1.4 equiv. of (3R,4R)-benzyl 3-fluoro-4-vinylpyrrolidine-1-carboxylate) in CH$_2$Cl$_2$ (10 mL) and NaBH(OAc)$_3$ (2.3 g, 10.7 mmol). The reaction mixture was then stirred for 16 h at room temperature. After quenched with saturated NaHCO$_3$ aqueous solution, the reaction mixture was extracted with EtOAc. The organic layer was washed with water and brine, dried over anhydrous Na$_2$SO$_4$, filtered and concentrated. The crude reductive amination product was contaminated by the HF eliminated alkene product, which was not separable on either silica column chromatography or preparative reverse phase HPLC. Therefore, the crude mixture (3.0 g) was dissolved in acetone and water (5:1, 120 mL). 4-Methylmorpholine N-oxide (715 mg, 6.1 mmol) and OsO$_4$ (2.15 mL of a 4% w/v solution) were added to this reaction mixture, which was then stirred for over the weekend at room temperature. After removal of acetone in vacuo, the remaining aqueous layer was extracted with EtOAc. The organic layer was washed with water and brine, dried over anhydrous Na$_2$SO$_4$, filtered and concentrated. The desired (3R,4R)-benzyl 3-(((R)-1-(1-benzyl-3-(2,5-difluorophenyl)-1H-1,2,4-triazol-5-yl)-2,2-dimethylpropylamino)methyl)-4-fluoropyrrolidine-1-carboxylate was obtained on silica column chromatography (35% to 80% EtOAc in Hexanes, 1.5 g, 35%). LC/MS (uplc) MH+ 592.3, 0.97 min.

Reductive Alkylation

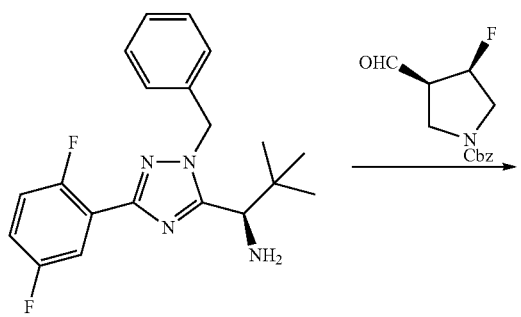

-continued

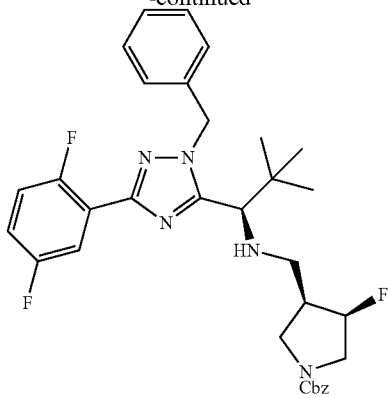

To a solution of (R)-1-(1-benzyl-3-(2,5-difluorophenyl)-1H-1,2,4-triazol-5-yl)-2,2-dimethylpropan-1-amine (2.55 g, 7.15 mmol) in CH$_2$Cl$_2$ (59 mL) was added the crude (3R,4S)-benzyl 3-fluoro-4-formylpyrrolidine-1-carboxylate (obtained from 1.4 equiv. of (3R,4R)-benzyl 3-fluoro-4-vinylpyrrolidine-1-carboxylate) in CH$_2$Cl$_2$ (10 mL) and NaBH(OAc)$_3$ (2.3 g, 10.7 mmol). The reaction mixture was then stirred for 16 h at room temperature. After quenched with saturated NaHCO$_3$ aqueous solution, the reaction mixture was extracted with EtOAc. The organic layer was washed with water and brine, dried over anhydrous Na$_2$SO$_4$, filtered and concentrated. The crude reductive amination product was contaminated by the HF eliminated alkene product, which was not separable on either silica column chromatography or preparative reverse phase HPLC. Therefore, the crude mixture (3.0 g) was dissolved in acetone and water (5:1, 120 mL). 4-Methylmorpholine N-oxide (715 mg, 6.1 mmol) and OsO$_4$ (2.15 mL of a 4% w/v solution) were added to this reaction mixture, which was then stirred for over the weekend at room temperature. After removal of acetone in vacuo, the remaining aqueous layer was extracted with EtOAc. The organic layer was washed with water and brine, dried over anhydrous Na$_2$SO$_4$, filtered and concentrated. The desired (3R,4R)-benzyl 3-(((R)-1-(1-benzyl-3-(2,5-difluorophenyl)-1H-1,2,4-triazol-5-yl)-2,2-dimethylpropylamino)methyl)-4-fluoropyrrolidine-1-carboxylate was obtained on silica column chromatography (35% to 80% EtOAc in Hexanes, 1.5 g, 35%). LC/MS (uplc) MH+ 592.3, 0.97 min.

Preparation of Acid Chloride

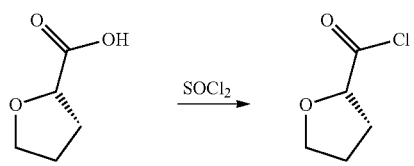

(S)-Tetrahydrofuran-2-carboxylic acid (5.1 g, 44 mmol) was dissolved with $SOCl_2$ (15 mL). The reaction mixture was refluxed for 30 min. After volatile material was removed in vacuo, the crude (S)-tetrahydrofuran-2-carbonyl chloride (6.0 g, >99%) was used for the next step.

Amide Bond Formation

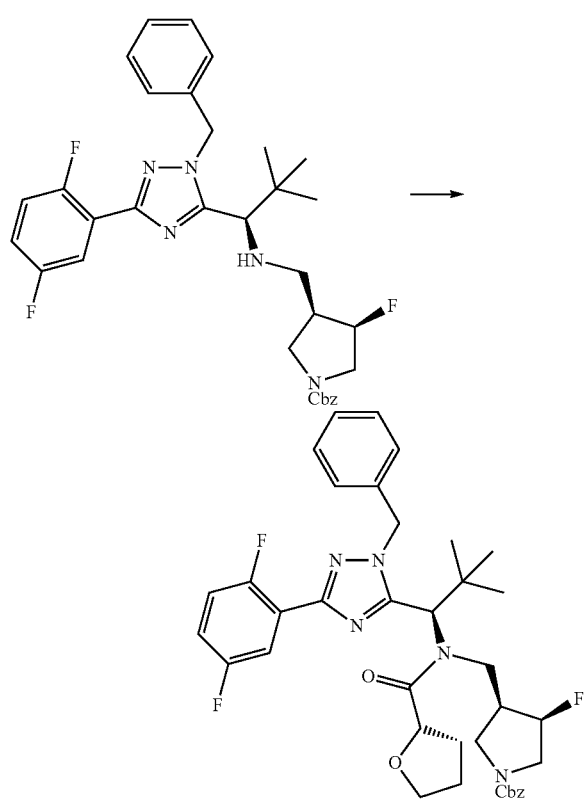

To a solution of (3R,4R)-benzyl 3-(((R)-1-(1-benzyl-3-(2,5-difluorophenyl)-1H-1,2,4-triazol-5-yl)-2,2-dimethylpropylamino)methyl)-4-fluoropyrrolidine-1-carboxylate (500 mg, 0.845 mmol) in dichloromethane (8.5 mL, 0.1 M solution) at room temperature was added triethylamine (236 µL, 1.69 mmol). The crude (S)-tetrahydrofuran-2-carbonyl chloride (227 mg, 1.69 mmol) was then added dropwise over 2 min. The resulting solution was stirred at room temperature for overnight. The reaction mixture was quenched with $H_2O$ and extracted with EtOAc. The organic layer was dried over anhydrous sodium sulfate and filtered. After the volatile organic materials were removed in vacuo, the desired (3R, 4R)-benzyl 3-(((S)—N—((R)-1-(1-benzyl-3-(2,5-difluorophenyl)-1H-1,2,4-triazol-5-yl)-2,2-dimethylpropyl)tetrahydrofuran-2-carboxamido)methyl)-4-fluoropyrrolidine-1-carboxylate was purified on flash column chromatography (yield: N/A) 0%-100%, EtOAc in hexanes). LC/MS (uplc): MH+ 690.5, 1.35 min.

Deprotection

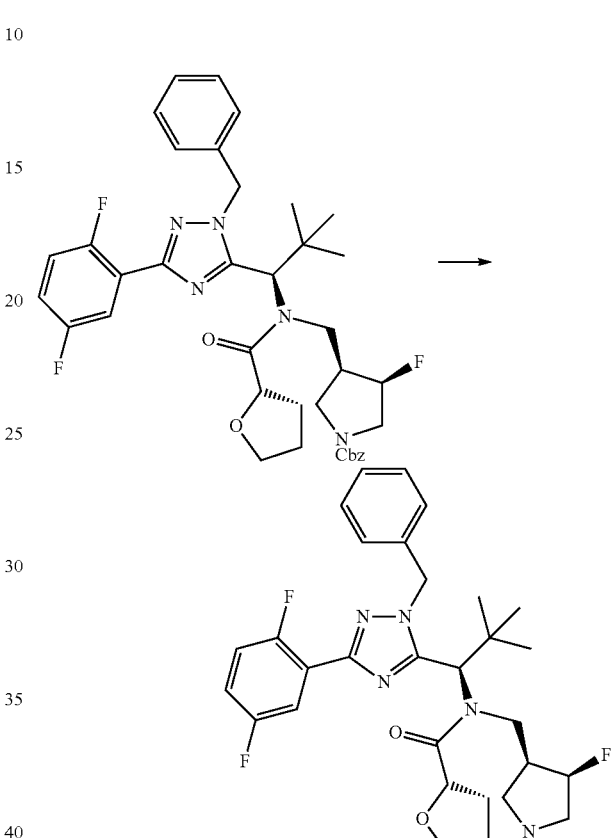

To a solution of (3R,4R)-benzyl 3-(((S)—N—((R)-1-(1-benzyl-3-(2,5-difluorophenyl)-1H-1,2,4-triazol-5-yl)-2,2-dimethylpropyl)tetrahydrofuran-2-carboxamido)methyl)-4-fluoropyrrolidine-1-carboxylate (583 mg, 0.845 mmol) in degassed EtOAc (8 mL, 0.1 M solution) was added Pd/C (899 mg, 10 wt %) under anhydrous $N_2$ atmosphere. After flushed with hydrogen gas, the reaction mixture equipped with a hydrogen gas balloon was stirred at room temperature for overnight. The reaction mixture was filtered through Celite® pad that was washed with EtOAc. The volatile organic filtrate was removed in vacuo to give the crude product, which was purified by preparative reverse phase HPLC. The combined fractions of the product were neutralized with saturated $NaHCO_3$ solution, which was then extracted with EtOAc. The organic layer was dried over anhydrous sodium sulfate, filtered and concentrated in vacuo. The dried product was then dissolved in acetonitrile and water (1:1 ratio) and lyophilized for 48 h. The white powdery (S)—N—((R)-1-(1-benzyl-3-(2,5-difluorophenyl)-1H-1,2,4-triazol-5-yl)-2,2-dimethylpropyl)-N-(((3S,4R)-4-fluoropyrrolidin-3-yl)methyl)tetrahydrofuran-2-carboxamide was obtained in 27.9% yield (131 mg) as a free amine $^1$H NMR ($CD_3Cl$, 400 MHz): δ 7.82 (1H, m), 7.53 (2H, m), 7.35-7.27 (3H, m), 7.14 (1H, m), 7.06 (1H, m), 6.14 (1H, s), 5.45 (2H, m), 4.85 (2H, m), 4.72 (1H, m), 4.21 (1H, m), 3.97 (1H, m), 3.83 (1H, m), 3.02 (1H, m), 2.80

(1H, m), 2.33-1.80 (6H, m), 1.25 (1H, s), 1.01 (1H, m), 0.99 (9H, s). LC/MS (uplc): MH⁺556.4, 0.99 min.

Example 2

N—((R)-1-(1-benzyl-3-(2,5-difluorophenyl)-1H-1,2,4-triazol-5-yl)-2,2-dimethylpropyl)-N-(((3R,4R)-4-fluoropyrrolidin-3-yl)methyl)-2,6-dimethylmorpholine-4-carboxamide

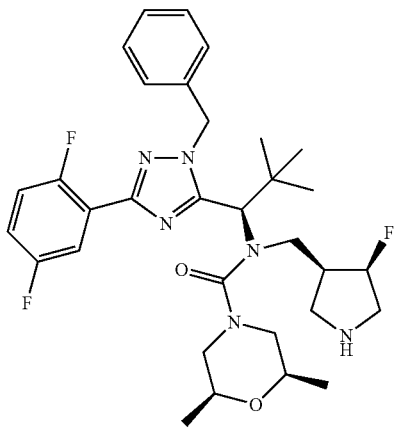 [SMILES: C[C@@H]1CN(C(=O)N(C[C@@H]2CNC[C@@H]2F)[C@@H](c2nc(-c3cc(F)ccc3F)nn2Cc2ccccc2)C(C)(C)C)C[C@H](C)O1]

Procedure

Urea Formation

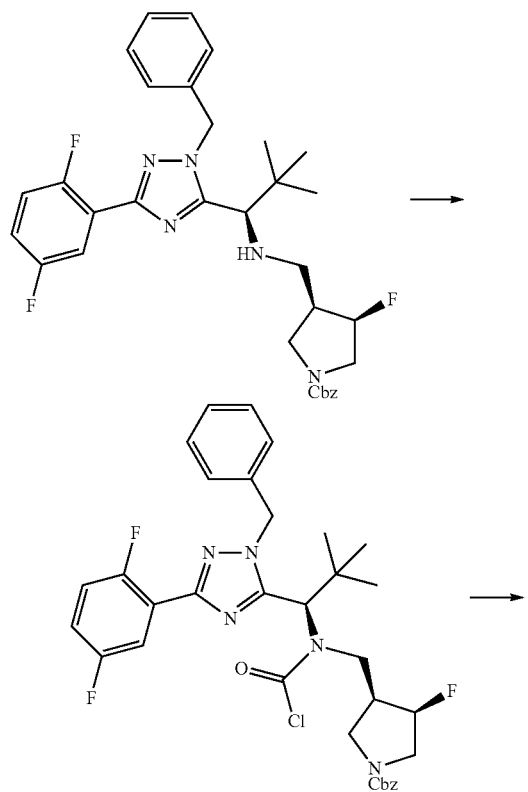

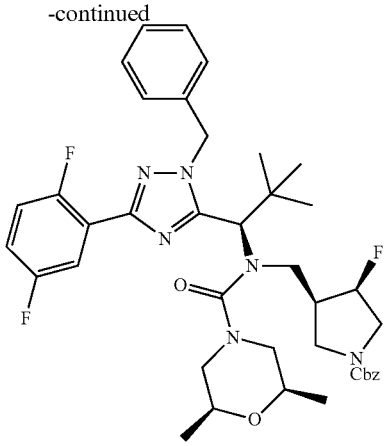

To a solution of (3R,4R)-benzyl 3-(((R)-1-(3-(2,5-difluorophenyl)-1-(3-fluorobenzyl)-1H-1,2,4-triazol-5-yl)-2,2-dimethylpropylamino)methyl)-4-fluoropyrrolidine-1-carboxylate (110 mg, 0.186 mmol) in dichloromethane (1.9 mL, 0.1 M solution) was added triethylamine (78 μL, 0.558 mmol) followed by addition of 20% phosgene in toluene (66 mg, 0.223 mmol) at room temperature. After the resulting solution was stirred at room temperature for 15 min (LC/MS (uplc): MH⁺654.3, 1.37 min for (3S,4R)-benzyl 3-((((R)-1-(1-benzyl-3-(2,5-difluorophenyl)-1H-1,2,4-triazol-5-yl)-2,2-dimethylpropyl)(chlorocarbonyl)amino)methyl)-4-fluoropyrrolidine-1-carboxylate), 2,6-dimethylmorpholine (64 mg, 0.558 mmol) was added and heat at 40° C. for overnight (in a seal tube). The reaction mixture was quenched with H₂O and extracted with EtOAc. The organic layer was washed with NaHCO₃ solution and brine, dried over anhydrous sodium sulfate, filtered and concentrated. After the volatile organic materials were removed in vacuo, the crude product was purified on preparative reverse phase HPLC. The combined fractions of the product were neutralized with saturated NaHCO₃ solution, which was then extracted with EtOAc. The organic layer was dried over anhydrous sodium sulfate, filtered and concentrated in vacuo to yield the desired (3R,4R)-benzyl 3-(((2S,6R)—N—(R)-1-(1-benzyl-3-(2,5-difluorophenyl)-1H-1,2,4-triazol-5-yl)-2,2-dimethylpropyl)-2,6-dimethylmorpholine-4-carboxamido)methyl)-4-fluoropyrrolidine-1-carboxylate (91 mg, 66.7%, over 2 steps). LC/MS (uplc): MH⁺733.5, 1.41 min.

Deprotection

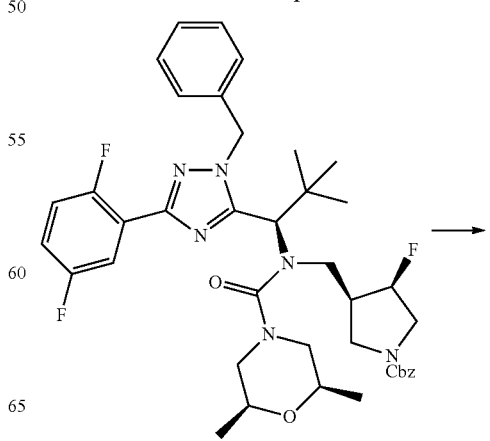

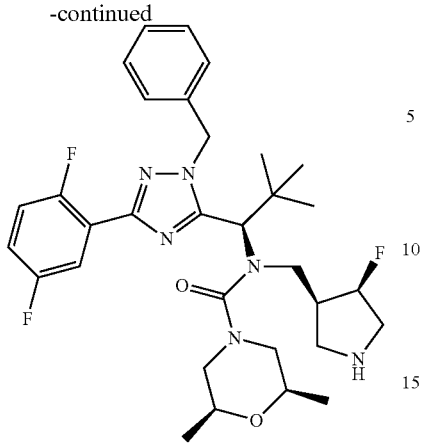

To a solution of (3R,4R)-benzyl 3-(((2S,6R)—N—((R)-1-(1-benzyl-3-(2,5-difluorophenyl)-1H-1,2,4-triazol-5-yl)-2,2-dimethylpropyl)-2,6-dimethylmorpholine-4-carboxamido)methyl)-4-fluoropyrrolidine-1-carboxylate (91 mg, 0.124 mmol) in degassed ethanol (12 mL, 0.1 M solution) was added Pd/C (2.64 mg, 10 wt %) under anhydrous $N_2$ atmosphere. After flushed with hydrogen gas, the reaction mixture equipped with a hydrogen gas balloon was stirred at room temperature for 45 min. The reaction mixture was filtered through Celite® pad that was washed with EtOAc. The volatile organic filtrate was removed in vacuo to give the crude product, which was purified by preparative reverse phase HPLC. The combined fractions of the product were neutralized with saturated $NaHCO_3$ solution, which was then extracted with EtOAc. The organic layer was dried over anhydrous sodium sulfate, filtered and concentrated in vacuo. The dried product was then dissolved in acetonitrile and water (1:1 ratio) and lyophilized for 48 h. The white powdery (2S,6R)—N—((R)-1-(1-benzyl-3-(2,5-difluorophenyl)-1H-1,2,4-triazol-5-yl)-2,2-dimethylpropyl)-N-(((3S,4R)-4-fluoropyrrolidin-3-yl)methyl)-2,6-dimethylmorpholine-4-carboxamide was obtained in 94% yield (70 mg) as a free amine $^1$H NMR ($CD_3Cl$, 300 MHz): δ 7.83 (1H, m), 7.52 (2H, m), 7.34-7.27 (3H, m), 7.08 (1H, m), 7.04 (1H, m), 5.94 (2H, m), 5.41 (1H, s), 3.92-3.62 (3H, m), 3.60-3.45 (3H, m), 3.17-2.58 (3H, m), 2.57-2.37 (1H, m), 2.35-2.04 (2H, m), 1.85 (2H, m), 1.20 (6H, s), 0.9 (1H, m), 0.8 (9H, s). LC/MS (uplc): $MH^+$ 599.5, 1.06 min.

Example 3

N—((R)-1-(3-(2,5-difluorophenyl)-1-(3-fluorobenzyl)-1H-1,2,4-triazol-5-yl)-2,2-dimethylpropyl)-N-(((3R,4R)-4-fluoropyrrolidin-3-yl)methyl)-2,6-dimethylmorpholine-4-carboxamide

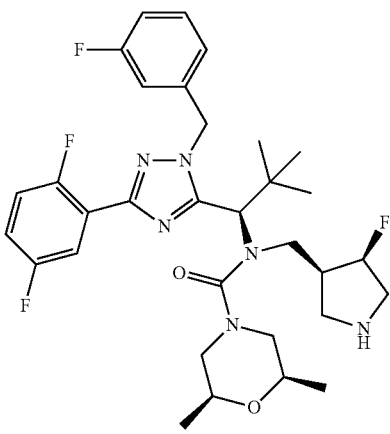 [SMILES: C[C@@H]1CN(C(=O)N(C[C@@H]2CNC[C@@H]2F)[C@@H](c2nc(-c3cc(F)ccc3F)nn2Cc2cccc(F)c2)C(C)(C)C)C[C@H](C)O1]

Procedure

Alkylation of (R)-tert-butyl 1-(3-(2,5-difluorophenyl)-1H-1,2,4-triazol-5-yl)-2,2-dimethylpropylcarbamate with 3-fluorobenzyl bromide (for CHIR782903)

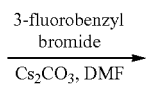

3-fluorobenzyl bromide
$Cs_2CO_3$, DMF

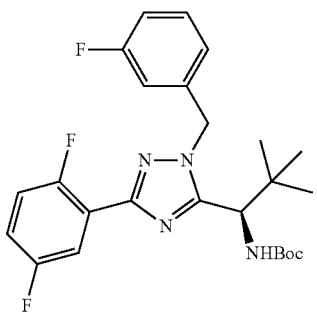

desired

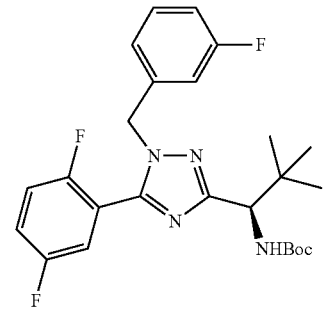

undesired

To a stirred suspension of (R)-tert-butyl 1-(3-(2,5-difluorophenyl)-1H-1,2,4-triazol-5-yl)-2,2-dimethylpropylcarbamate (5.89 g, 16.1 mmol) and $Cs_2CO_3$ (10.5 g, 32.2 mmol) in DMF (46 mL, 0.35 M) was added 3-fluorobenzyl bromide (2.17 mL, 17.7 mmol). Once the reaction was complete, the mixture was partitioned between EtOAc and $H_2O$. The organic layer was separated and washed with $H_2O$, brine, then dried over $Na_2SO_4$, filtered, and evaporated in vacuo to give (R)-tert-butyl 1-(3-(2,5-difluorophenyl)-1-(3-fluorobenzyl)-1H-1,2,4-triazol-5-yl)-2,2-dimethylpropylcarbamate. The desired less polar regioisomer was obtained by silica gel column (0% to 100% EtOAc in Hexanes, 5.05 g, 66.2%).

For the desired isomer, (R)-tert-butyl 1-(3-(2,5-difluorophenyl)-1-(3-fluorobenzyl)-1H-1,2,4-triazol-5-yl)-2,2-dimethylpropylcarbamate: LC/MS (uplc) 475.2, 1.35 min. For the undesired isomer (R)-tert-butyl 1-(5-(2,5-difluorophenyl)-1-(3-fluorobenzyl)-1H-1,2,4-triazol-3-yl)-2,2-dimethylpropylcarbamate. LC/MS (uplc) MH+ 475.2, 1.24 min.

Deprotection of (R)-tert-butyl 1-(1-benzyl-3-(2,5-difluorophenyl)-1H-1,2,4-triazol-5-yl)-2,2-dimethyl-propylcarbamate (for CHIR782903)

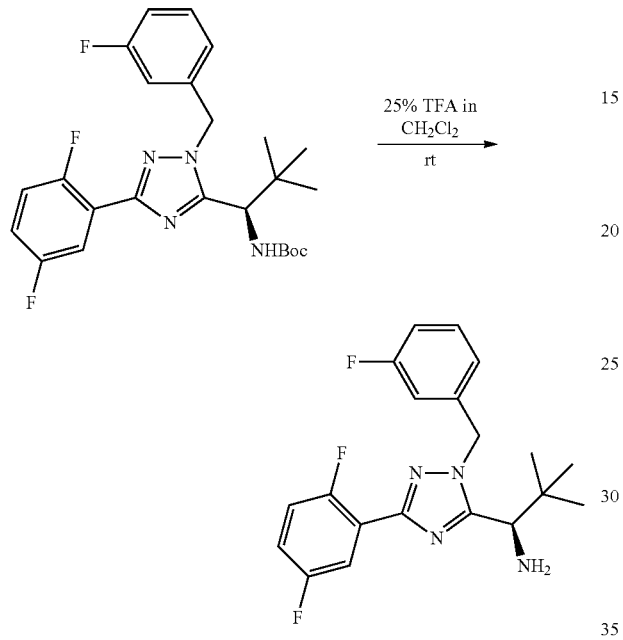

(R)-tert-butyl 1-(3-(2,5-difluorophenyl)-1-(3-fluorobenzyl)-1H-1,2,4-triazol-5-yl)-2,2-dimethylpropylcarbamate (5.05 g, 10.7 mmol) was treated with TFA (10 mL) in CH$_2$Cl$_2$ (30 ml). Once the reaction was complete, the reaction was concentrated in vacuo and then partitioned between EtOAc and saturated aqueous NaHCO$_3$ solution. The organics were separated, then washed with H$_2$O, brine, then dried over Na$_2$SO$_4$, filtered, and evaporated under reduced pressure to give (R)-1-(3-(2,5-difluorophenyl)-1-(3-fluorobenzyl)-1H-1,2,4-triazol-5-yl)-2,2-dimethylpropan-1-amine which was directly used for the next step without further purification (2.55 g, 64%). LC/MS (uplc) MH+ 375.1, 0.83 min.

Reductive Alkylation

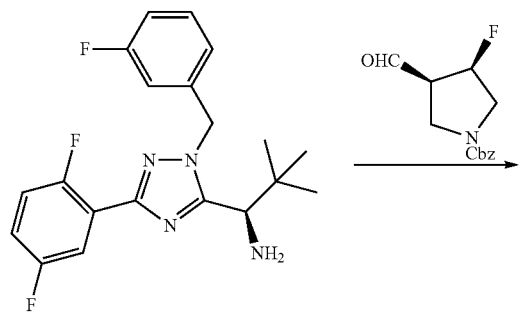

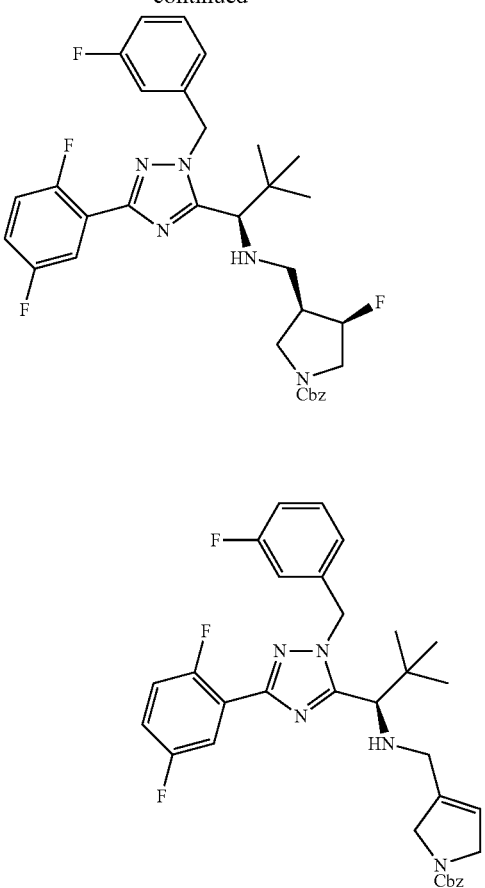

To a solution of (R)-1-(3-(2,5-difluorophenyl)-1-(3-fluorobenzyl)-1H-1,2,4-triazol-5-yl)-2,2-dimethylpropan-1-amine (2.55 g, 6.8 mmol) in CH$_2$Cl$_2$ (58 mL) was added the crude (3R,4S)-benzyl 3-fluoro-4-formylpyrrolidine-1-carboxylate (obtained from 1.4 equiv. of (3R,4R)-benzyl 3-fluoro-4-vinylpyrrolidine-1-carboxylate) in CH$_2$Cl$_2$ (10 mL) and NaBH(OAc)$_3$ (2.2 g, 10.2 mmol). The reaction mixture was then stirred for 16 h at room temperature. After quenched with saturated NaHCO$_3$ aqueous solution, the reaction mixture was extracted with EtOAc. The organic layer was washed with water and brine, dried over anhydrous Na$_2$SO$_4$, filtered and concentrated. The crude reductive amination product was contaminated by the HF eliminated alkene product, which was not separable on either silica column chromatography or preparative reverse phase HPLC. Therefore, the crude mixture (2.89 g) was dissolved in acetone and water (5:1, 120 mL). 4-Methylmorpholine N-oxide (667 mg, 5.7 mmol) and OsO$_4$ (1.51 mL of a 4% w/v solution) were added to this reaction mixture, which was then stirred for over the weekend at room temperature. After removal of acetone in vacuo, the remaining aqueous layer was extracted with EtOAc. The organic layer was washed with water and brine, dried over anhydrous Na$_2$SO$_4$, filtered and concentrated. The desired (3R,4R)-benzyl 3-(((R)-1-(3-(2,5-difluorophenyl)-1-(3-fluorobenzyl)-1H-1,2,4-triazol-5-yl)-2,2-dimethylpropylamino)methyl)-4-fluoropyrrolidine-1-carboxylate was obtained on silica column chromatography (40% to 90% EtOAc in Hexanes, 2.16 g, 52%). LC/MS (uplc): MH+ 610.2, 0.99 min.

Urea Formation

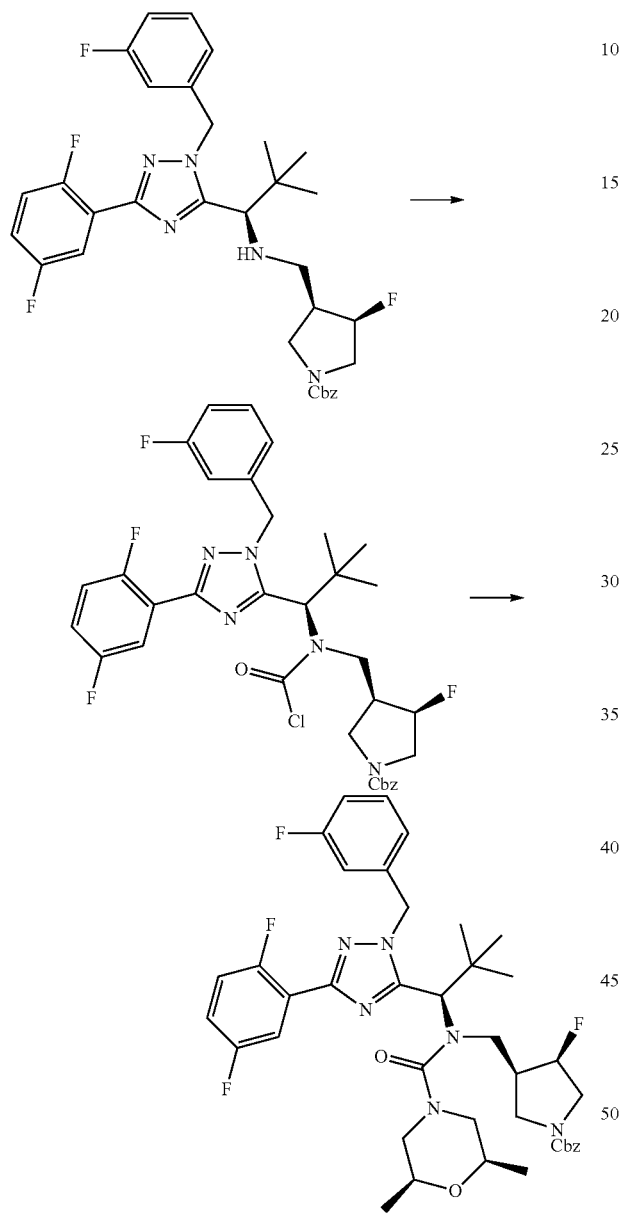

To a solution of (3R,4R)-benzyl 3-(((R)-1-(3-(2,5-difluorophenyl)-1-(3-fluorobenzyl)-1H-1,2,4-triazol-5-yl)-2,2-dimethylpropylamino)methyl)-4-fluoropyrrolidine-1-carboxylate (30 mg, 0.049 mmol) in dichloromethane (450 μL, 0.1 M solution) was added triethylamine (20.6 μL, 0.148 mmol) followed by addition of 20% phosgene in toluene (6.2 μL, 0.059 mmol) at room temperature. After the resulting solution was stirred at room temperature for 15 min (LC/MS (uplc): MH+ 654.3, 1.37 min for (3S,4R)-benzyl 3-((((R)-1-(1-benzyl-3-(2,5-difluorophenyl)-1H-1,2,4-triazol-5-yl)-2,2-dimethylpropyl)(chlorocarbonyl)amino)methyl)-4-fluoropyrrolidine-1-carboxylate), 2,6-dimethylmorpholine (64 mg, 0.558 mmol) was added and stirred for 15 min at room temperature. The reaction mixture was quenched with H₂O and extracted with EtOAc. The organic layer was washed with NaHCO₃ solution and brine, dried over anhydrous sodium sulfate, filtered and concentrated. After the volatile organic materials were removed in vacuo, the crude product was purified on preparative reverse phase HPLC. The combined fractions of the product were neutralized with saturated NaHCO₃ solution, which was then extracted with EtOAc. The organic layer was dried over anhydrous sodium sulfate, filtered and concentrated in vacuo to yield the desired (3R,4R)-benzyl 3-(((2S,6R)—N—((R)-1-(3-(2,5-difluorophenyl)-1-(3-fluorobenzyl)-1H-1,2,4-triazol-5-yl)-2,2-dimethylpropyl)-2,6-dimethylmorpholine-4-carboxamido)methyl)-4-fluoropyrrolidine-1-carboxylate (30 mg, 81%, over 2 steps). LC/MS (uplc): MH+ 751.5, 1.39 min.

Deprotection

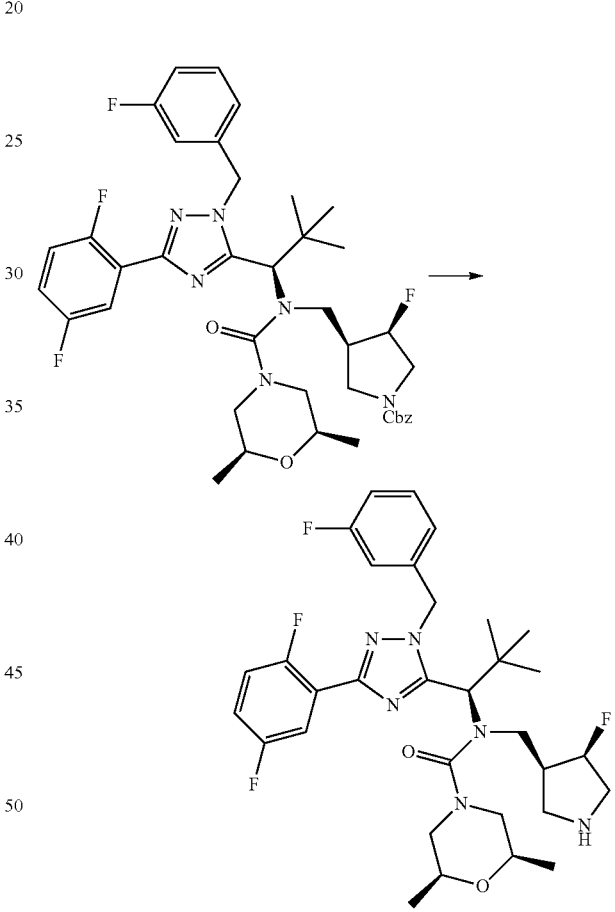

To a solution of (3R,4R)-benzyl 3-(((2S,6R)—N—((R)-1-(3-(2,5-difluorophenyl)-1-(3-fluorobenzyl)-1H-1,2,4-triazol-5-yl)-2,2-dimethylpropyl)-2,6-dimethylmorpholine-4-carboxamido)methyl)-4-fluoropyrrolidine-1-carboxylate (35 mg, 0.047 mmol) in degassed ethanol (10 mL, 4.7 mM solution) was added Pd/C (0.99 mg, 10 wt %) under anhydrous N₂ atmosphere. After flushed with hydrogen gas, the reaction mixture equipped with a hydrogen gas balloon was stirred at room temperature for overnight. The reaction mixture was filtered through Celite® pad that was washed with EtOAc. The volatile organic filtrate was removed in vacuo to give the crude product, which was purified by preparative reverse phase HPLC. The combined fractions of the product were neutralized with saturated NaHCO₃ solution, which was then extracted with EtOAc. The organic layer was dried over anhydrous sodium sulfate, filtered and concentrated in vacuo. The dried product was then dissolved in acetonitrile and water (1:1 ratio) and lyophilized for 48 h. The white powdery (2S,6R)—N—((R)-1-(3-(2,5-difluorophenyl)-1-(3-fluorobenzyl)-1H-1,2,4-triazol-5-yl)-2,2-dimethylpropyl)-N-(((3S,4R)-4-fluoropyrrolidin-3-yl)methyl)-2,6-dimethylmorpholine-4-carboxamide was obtained in 63% yield (18 mg) as a free amine $^1$H NMR (CD₃Cl, 300 MHz): δ 7.84 (1H, m), 7.32-6.95 (6H, m), 5.79 (2H, m), 5.36 (1H, s), 4.58 (1H, m), 3.91-3.72 (3H, m), 3.65-3.50 (3H, m), 3.04 (1H, m), 2.97-2.65 (2H, m), 2.53 (1H, m), 2.36 (1H, m), 2.18 (1H, m), 1.20 (6H, s), 0.9 (1H, m), 0.84 (9H, s). LC/MS (uplc): MH⁺ 617.5, 1.06 min.

Example 4

(S)—N—((R)-1-(1-benzyl-3-(2,5-difluorophenyl)-1H-1,2,4-triazol-5-yl)-2,2-dimethylpropyl)-N-(((3R,4R)-4-fluoropyrrolidin-3-yl)methyl)-2-hydroxypropanamide

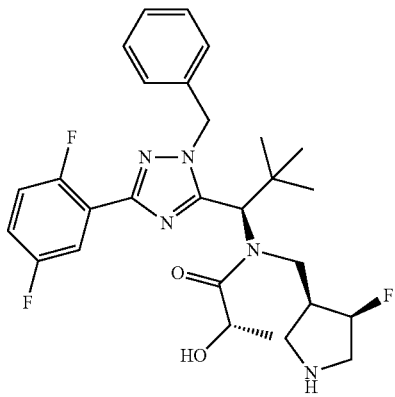 [SMILES: C[C@H](O)C(=O)N(C[C@@H]1CNC[C@@H]1F)[C@@H](c1nc(-c2cc(F)ccc2F)nn1Cc1ccccc1)C(C)(C)C]

Procedure

Amide Bond Formation

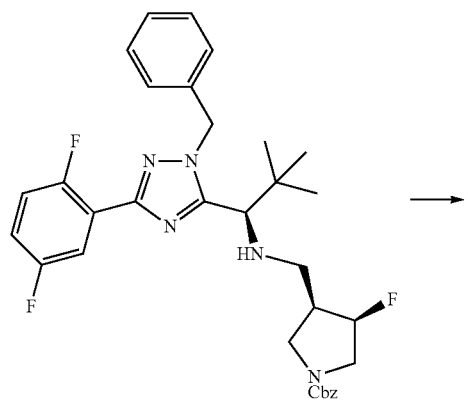

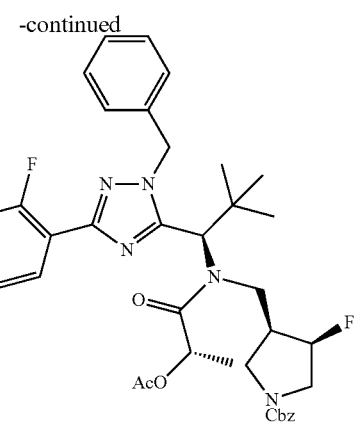

To a solution of (3R,4R)-benzyl 3-(((R)-1-(1-benzyl-3-(2,5-difluorophenyl)-1H-1,2,4-triazol-5-yl)-2,2-dimethylpropylamino)methyl)-4-fluoropyrrolidine-1-carboxylate (1.5 g, 2.53 mmol) in dichloromethane (25 mL, 0.1 M solution) at room temperature was added triethylamine (458 μL, 3.29 mmol). (S)-1-Chloro-1-oxopropan-2-yl acetate (416 μL, 3.29 mmol) was then added dropwise over 2 min. The resulting solution was stirred at room temperature for overnight. The reaction mixture was quenched with H₂O and extracted with EtOAc. The organic layer was dried over anhydrous sodium sulfate and filtered. After the volatile organic materials were removed in vacuo, the desired (3R,4R)-benzyl 3-(((S)-2-acetoxy-N-((R)-1-(1-benzyl-3-(2,5-difluorophenyl)-1H-1,2,4-triazol-5-yl)-2,2-dimethylpropyl)-propanamido)methyl)-4-fluoropyrrolidine-1-carboxylate was purified on flash column chromatography (0%-400%, EtOAc in hexanes). LC/MS (uplc): MH⁺ 706.5, 1.34 min.

Global Deprotection

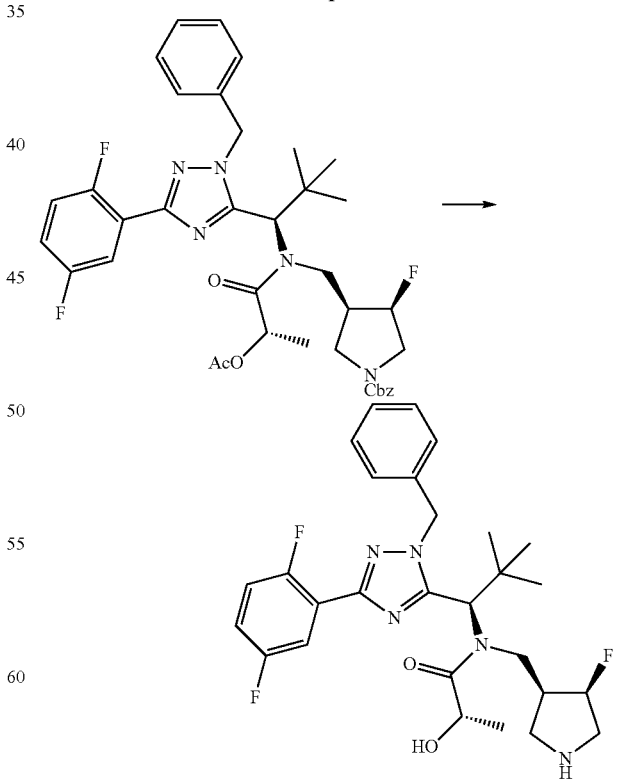

To a solution of (3R,4R)-benzyl 3-(((S)-2-acetoxy-N—((R)-1-(1-benzyl-3-(2,5-difluorophenyl)-1H-1,2,4-triazol-5- yl)-2,2-dimethylpropyl)propanamido)methyl)-4-fluoropyrrolidine-1-carboxylate (1.78 g, 2.53 mmol) in degassed EtOAc (25 mL, 0.1 M solution) was added Pd/C (178 mg, 10 wt %) under anhydrous $N_2$ atmosphere. After flushed with hydrogen gas, the reaction mixture equipped with a hydrogen gas balloon was stirred at room temperature for overnight. The reaction mixture was filtered through Celite® pad that was washed with EtOAc. The volatile organic filtrate was removed in vacuo to give the crude amine (LC/MS (uplc): $MH^+$ 572.4, 1.11 min). Then, the crude product was dissolved in MeOH (168 mL, 0.015 M solution) followed by addition of anhydrous potassium carbonate (3.5 g, 25 mmol). The reaction was then stirred for 15 min at room temperature. After white precipitate was removed by filtration, the organic filtrate was concentrated in vacuo. The crude product was purified by preparative reverse phase HPLC. The combined fractions of the product were neutralized with saturated $NaHCO_3$ solution, which was then extracted with EtOAc (200 mL). The organic layer was dried over anhydrous sodium sulfate, filtered and concentrated in vacuo. The dried product was then dissolved in acetonitrile and water (1:1 ratio) and lyophilized for 48 h. The white powdery (S)—N—((R)-1-(1-benzyl-3-(2,5-difluorophenyl)-1H-1,2,4-triazol-5-yl)-2,2-dimethylpropyl)-N-(((3S,4R)-4-fluoropyrrolidin-3-yl) methyl)-2-hydroxypropanamide was obtained in 65.5% yield (876 mg, over 3 steps) as a free amine $^1$H NMR ($CD_3Cl$, 400 MHz): 7.82 (1H, m), 7.52 (2H, m), 7.34-7.25 (3H, m), 7.16 (1H, m), 7.07 (1H, m), 6.09 (1H, s), 5.44 (2H, s), 4.61 (2H, m), 4.39 (1H, m), 3.78 (1H, m), 3.60 (1H, m), 2.92 (1H, m), 2.56 (1H, m), 2.16 (2H, m), 1.44 (3H, m), 1.22 (1H, m), 0.99 (9H, s), 0.42 (1H, m). LC/MS (uplc): $MH^+$ 530.3, 1.05 min.

Example 5

(S)—N—((R)-1-(3-(2,5-difluorophenyl)-1-(3-fluorobenzyl)-1H-1,2,4-triazol-5-yl)-2,2-dimethylpropyl)-N-(((3R,4R)-4-fluoropyrrolidin-3-yl)methyl) tetrahydrofuran-2-carboxamide

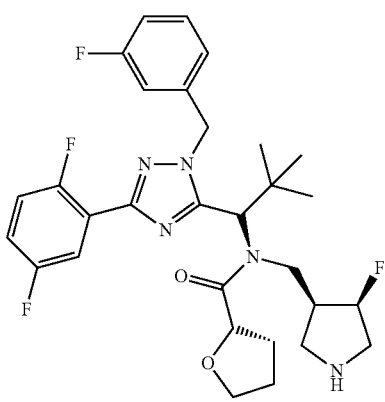

Procedure

Amide Bond Formation

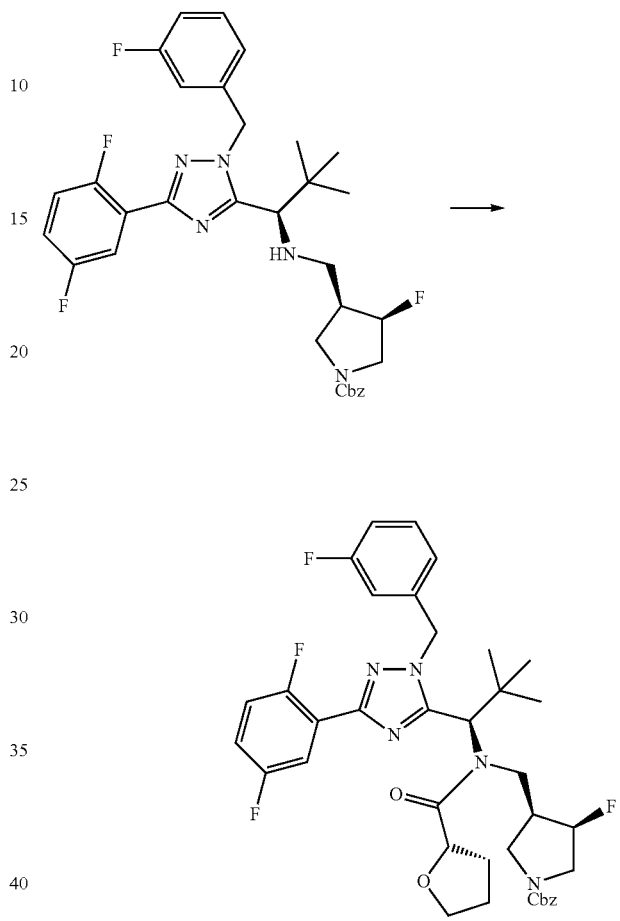

To a solution of (3R,4R)-benzyl 3-(((R)-1-(3-(2,5-difluorophenyl)-1-(3-fluorobenzyl)-1H-1,2,4-triazol-5-yl)-2,2-dimethylpropylamino)methyl)-4-fluoropyrrolidine-1-carboxylate (500 mg, 0.82 mmol) in dichloromethane (4 mL, 0.2 M solution) at room temperature was added triethylamine (229 µL, 1.64 mmol). The crude (S)-tetrahydrofuran-2-carbonyl chloride (221 mg, 1.64 mmol) was then added dropwise over 2 min. The resulting solution was stirred at room temperature for overnight. The reaction mixture was quenched with $H_2O$ and extracted with EtOAc. The organic layer was dried over anhydrous sodium sulfate and filtered. After the volatile organic materials were removed in vacuo, the desired (3R,4R)-benzyl 3-(((S)—N—((R)-1-(3-(2,5-difluorophenyl)-1-(3-fluorobenzyl)-1H-1,2,4-triazol-5-yl)-2,2-dimethylpropyl)tetrahydrofuran-2-carboxamido)methyl)-4-fluoropyrrolidine-1-carboxylate was purified on flash column chromatography (yield N/A; 0%-100%, EtOAc in hexanes). LC/MS (uplc): MH+ 708.4, 1.35 min.

Deprotection

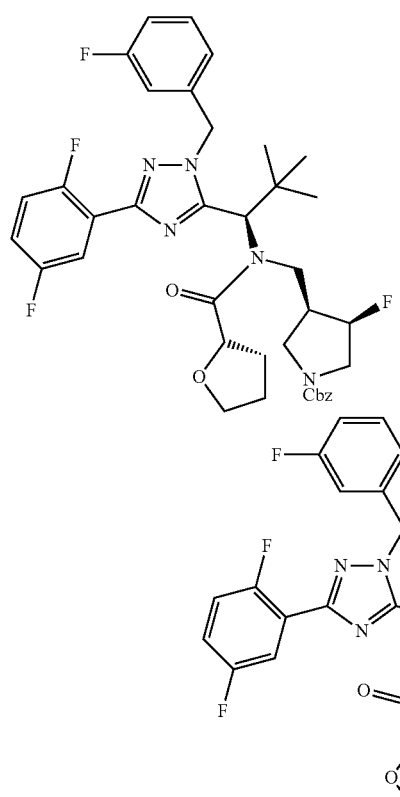

To a solution of (3R,4R)-benzyl 3-(((S)—N—((R)-1-(3-(2,5-difluorophenyl)-1-(3-fluorobenzyl)-1H-1,2,4-triazol-5-yl)-2,2-dimethylpropyl)tetrahydrofuran-2-carboxamido)methyl)-4-fluoropyrrolidine-1-carboxylate (580 mg, 0.82 mmol) in degassed EtOAc (80 mL, 0.1 M solution) was added Pd/C (873 mg, 10 wt %) under anhydrous N$_2$ atmosphere. After flushed with hydrogen gas, the reaction mixture equipped with a hydrogen gas balloon was stirred at room temperature for overnight. The reaction mixture was filtered through Celite® pad that was washed with EtOAc. The volatile organic filtrate was removed in vacuo to give the crude product, which was purified by preparative reverse phase HPLC. The combined fractions of the product were neutralized with saturated NaHCO$_3$ solution, which was then extracted with EtOAc. The organic layer was dried over anhydrous sodium sulfate, filtered and concentrated in vacuo. The dried product was then dissolved in acetonitrile and water (1:1 ratio) and lyophilized for 48 h. The white powdery (S)—N—((R)-1-(3-(2,5-difluorophenyl)-1-(3-fluorobenzyl)-1H-1,2,4-triazol-5-yl)-2,2-dimethylpropyl)-N-(((3S,4R)-4-fluoropyrrolidin-3-yl)methyl)tetrahydrofuran-2-carboxamide was obtained in 10.4% yield (48.9 mg) as a free amine. $^1$H NMR (CD$_3$Cl, 400 MHz): 7.82 (1H, m), 7.34-7.25 (3H, m), 7.22 (1H, m), 7.15 (1H, m), 7.07 (1H, m), 6.98 (1H, m), 6.10 (1H, s), 5.44 (2H, m), 4.86 (2H, m), 4.19 (1H, m), 3.96 (1H, m), 3.86 (2H, m), 3.05 (1H, m), 3.05 (1H, m), 2.37-1.70 (2H, m), 1.35-1.02 (5H, m), 0.99 (9H, s). LC/MS (uplc): MH+ 574.4, 0.98 min.

Example 6

(S)—N—((R)-1-(3-(2,5-difluorophenyl)-1-(3-fluorobenzyl)-1H-1,2,4-triazol-5-yl)-2,2-dimethylpropyl)-N-(((3R,4R)-4-fluoropyrrolidin-3-yl)methyl)-2-hydroxypropanamide

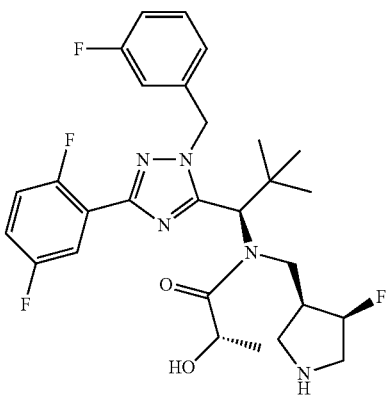 [SMILES: C[C@H](O)C(=O)N(C[C@@H]1CNC[C@@H]1F)[C@@H](c1nc(-c2cc(F)ccc2F)nn1Cc1cccc(F)c1)C(C)(C)C]

Amide Bond Formation

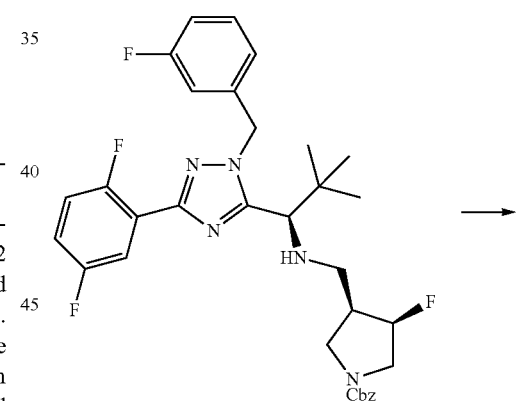

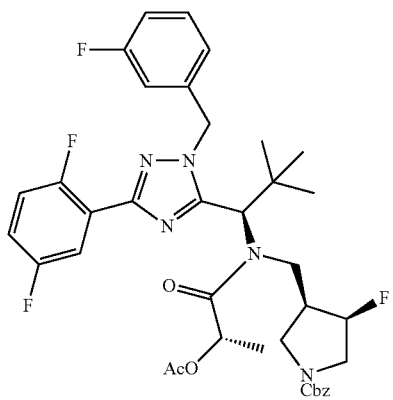

To a solution of (3R,4R)-benzyl 3-(((R)-1-(3-(2,5-difluorophenyl)-1-(3-fluorobenzyl)-1H-1,2,4-triazol-5-yl)-2,2-dimethylpropylamino)methyl)-4-fluoropyrrolidine-1-carboxylate (1.48 g, 2.43 mmol) in dichloromethane (25 mL, 0.1 M solution) at room temperature was added triethylamine (440 µL, 3.16 mmol). (S)-1-Chloro-1-oxopropan-2-yl acetate (400 µL, 3.16 mmol) was then added dropwise over 2 min. The resulting solution was stirred at room temperature for overnight. The reaction mixture was quenched with H₂O and extracted with EtOAc. The organic layer was dried over anhydrous sodium sulfate and filtered. After the volatile organic materials were removed in vacuo, the desired (3R,4R)-benzyl 3-(((S)-2-acetoxy-N-((R)-1-(3-(2,5-difluorophenyl)-1-(3-fluorobenzyl)-1H-1,2,4-triazol-5-yl)-2,2-dimethylpropyl)propanamido)methyl)-4-fluoropyrrolidine-1-carboxylate was purified by flash column chromatography (0%-100%, EtOAc in hexanes). LC/MS (uplc) MH+ 724.4, 1.34 min.

Global Deprotection

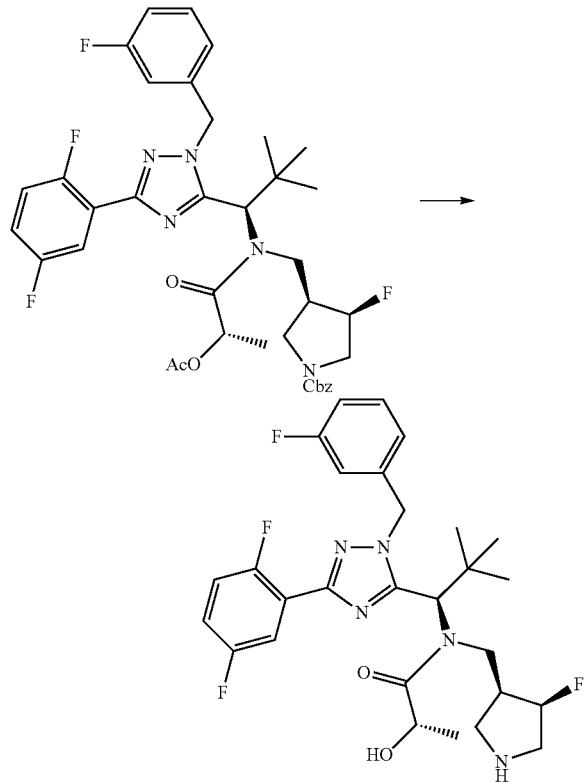

To a solution of (3R,4R)-benzyl 3-(((S)-2-acetoxy-N-((R)-1-(3-(2,5-difluorophenyl)-1-(3-fluorobenzyl)-1H-1,2,4-triazol-5-yl)-2,2-dimethylpropyl)propanamido)methyl)-4-fluoropyrrolidine-1-carboxylate (2.24 g, 3.09 mmol) in degassed EtOAc (25 mL, 0.1 M solution) was added Pd/C (224 mg, 10 wt %) under anhydrous N₂ atmosphere. After flushed with hydrogen gas, the reaction mixture equipped with a hydrogen gas balloon was stirred at room temperature for overnight. The reaction mixture was filtered through Celite® pad that was washed with EtOAc. The volatile organic filtrate was removed in vacuo to give the crude amine. Then, the crude product was dissolved in MeOH (200 mL, 0.015 M solution) followed by addition of anhydrous potassium carbonate (4.2 g, 30.9 mmol). The reaction was then stirred for 15 min at room temperature. After white precipitate was removed by filtration, the organic filtrate was concentrated in vacuo. The crude product was purified by preparative reverse phase HPLC. The combined fractions of the product were neutralized with saturated NaHCO₃ solution, which was then extracted with EtOAc (200 mL). The organic layer was dried over anhydrous sodium sulfate, filtered and concentrated in vacuo. The dried product was then dissolved in acetonitrile and water (1:1 ratio) and lyophilized for 48 h. The white powdery (S)—N—((R)-1-(3-(2,5-difluorophenyl)-1-(3-fluorobenzyl)-1H-1,2,4-triazol-5-yl)-2,2-dimethylpropyl)-N-(((3S,4R)-4-fluoropyrrolidin-3-yl)methyl)-2-hydroxypropanamide was obtained in 57% yield (962 mg, over 3 steps) as a free amine $^1$H NMR (CD₃OD, 400 MHz): 7.81 (1H, m), 7.40-7.16 (5H, m), 7.06 (1H, m), 6.12 (1H, s), 5.44 (2H, m), 4.77 (2H, m), 3.87 (1H, m), 2.82 (2H, m), 2.28 (1H, m), 2.17 (1H, m), 1.95 (1H, m), 1.43 (3H, m), 1.22 (1H, m), 0.91 (9H, s). LC/MS (uplc): MH⁺ 548.3, 0.94 min.

Example 7

Assay for Determining KSP Activity

This example provides a representative in vitro assay for determining KSP activity in vitro. Purified microtubules obtained from bovine brain were purchased from Cytoskeleton Inc. (Denver, Colo., USA). The motor domain of human KSP (Eg 5, KNSL1) was cloned, expressed, and purified to greater than 95% homogeneity. Biomol Green was purchased from BIOMOL International L.P. (Plymouth Meeting, Pa., USA). The microtubules were rapidly thawed at 37° C. for 10 minutes before making dilution. Microtubules and KSP motor protein (i.e., the KSP motor domain) were diluted in assay buffer (20 mM Tris-HCl (pH 7.5), 1 mM MgCl₂, 10 mM DTT and 0.125% BSA) to a final concentration of 50 µg/mL microtubules and 3 nM KSP.

To each well of the testing plate (96-well half area plate) containing 1.25 µL of inhibitor or test compound in DMSO (or DMSO only in the case of controls) were added 25 µL of ATP solution (ATP diluted to a concentration of 250 µM in assay buffer) and 25 µL of the above-described microtubule/KSP solution. The plates were incubated at RT for 2 hours. Following incubation, 65 µL of Biomol Green (a malachite green-based dye that detects the release of inorganic phosphate) with 0.015% Tween 20 was added to each well. The plates were incubated for an additional 15-20 minutes then the absorbance at 650 nm was determined using a Molecular Devices Spectrophotometer. The amount of absorbance at 650 nm corresponded to the amount of KSP activity in the samples. The IC₅₀ of each inhibitor or test compound was then determined based on the decrease in absorbance at 650 nm at each concentration, via nonlinear regression using either XLFit for Excel or Prism data analysis software by GraphPad Software Inc.

Preferred compounds of the invention have a biological activity as measured by an IC₅₀ of less than about 1 mM in assay protocols described in Example 7, with preferred embodiments having biological activity of less than about 25 µM, with particularly preferred embodiments having biological activity of less than about 1000 nM, and with the most preferred embodiments having biological activity of less than about 100 nM.

Table 1 lists structures, IC₅₀ values, mass spec data, and retention time for the illustrative examples representing the present invention.

TABLE 1

| CMPD # | STRUCTURE | Biological Activity (IC50) | retention time (min) | mass (MH+) | method |
|---|---|---|---|---|---|
| 1 | 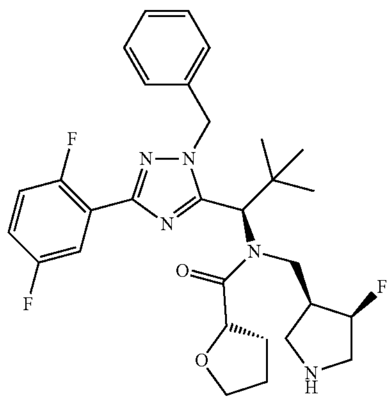 | 0.96 nM | 0.99 | 556.4 | LC/MS (uplc) |
| 2 | 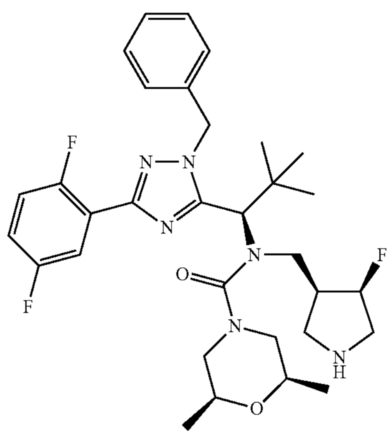 [SMILES: C[C@@H]1CN(C(=O)N(C[C@@H]2CNC[C@@H]2F)[C@@H](c2nc(-c3cc(F)ccc3F)nn2Cc2ccccc2)C(C)(C)C)C[C@H](C)O1] | 0.83 nM | 1.06 | 599.5 | LC/MS (uplc) |
| 3 | 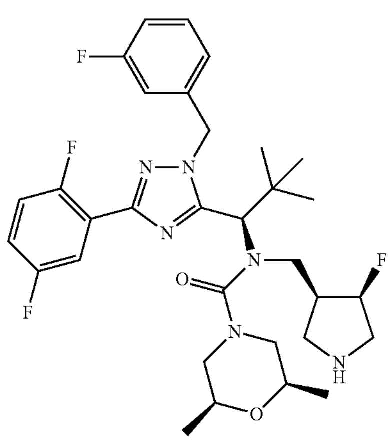 [SMILES: C[C@@H]1CN(C(=O)N(C[C@@H]2CNC[C@@H]2F)[C@@H](c2nc(-c3cc(F)ccc3F)nn2Cc2cccc(F)c2)C(C)(C)C)C[C@H](C)O1] | 0.74 nM | 1.06 | 617.5 | LC/MS (uplc) |

TABLE 1-continued

| CMPD # | STRUCTURE | Biological Activity (IC50) | retention time (min) | mass (MH+) | method |
| --- | --- | --- | --- | --- | --- |
| 4 | 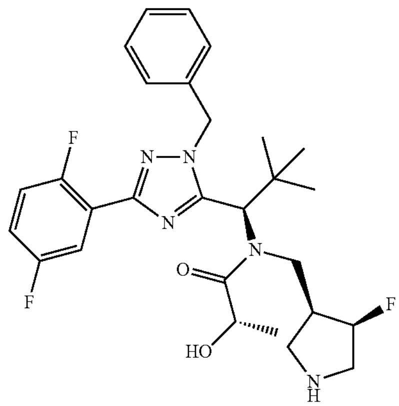 [SMILES: C[C@H](O)C(=O)N(C[C@@H]1CNC[C@@H]1F)[C@@H](c1nc(-c2cc(F)ccc2F)nn1Cc1ccccc1)C(C)(C)C] | 0.60 nM | 1.05 | 530.3 | LC/MS (uplc) |
| 5 | 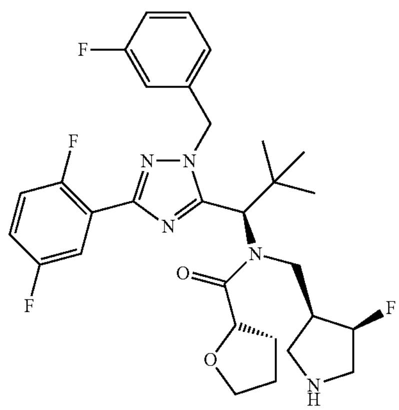 | 1.46 nM | 0.98 | 574.4 | LC/MS (uplc) |
| 6 | 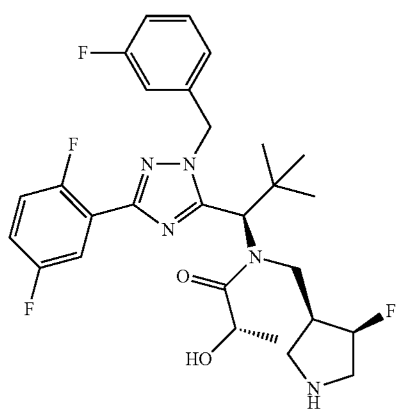 [SMILES: C[C@H](O)C(=O)N(C[C@@H]1CNC[C@@H]1F)[C@@H](c1nc(-c2cc(F)ccc2F)nn1Cc1cccc(F)c1)C(C)(C)C] | 0.83 nM | 0.94 | 548.3 | LC/MS (uplc) |

Additional compounds of the invention are in Table 2 below. These compounds were prepared similarly to those described above, and incorporate an alkoxy group in $R^1$. The alkoxy-containing portion of these compounds can be made as illustrated in the following Examples.

Example 9

Methylation of (R)-2-((tert-butoxycarbonyl)amino)-3-hydroxy-3-methylbutanoic acid

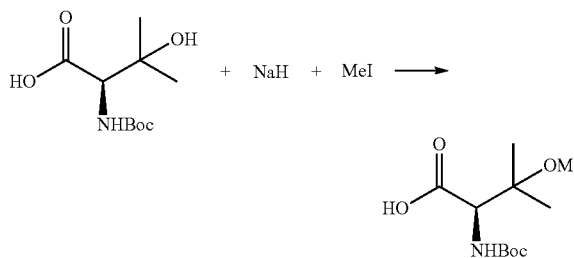

To a solution of sodium hydride suspension in mineral oil (60% wt) (3.86 g, 96 mmol) in dry THF (60 mL) were added (R)-2-((tert-butoxycarbonyl)amino)-3-hydroxy-3-methylbutanoic acid (7.5 g, 32.2 mmol) in THF (50 mL) at 0° C. slowly. After stirring for 1 h at room temperature, iodomethane (4.31 ml, 38.6 mmol) was added. The reaction mixture was stirred at room temperature overnight. After quenched with water, the reaction mixture was extracted by ether. The aqueous layers was acidify to pH=3 by adding 6 N HCl, then extracted by EtOAc. The organic layer was washed with brine, dried over anhydrous $Na_2SO_4$, filtered though Buchner funnel, and concentrated to yield crude (R)-2-((tert-butoxycarbonyl) amino)-3-methoxy-3-methylbutanoic acid (7 g, 28.3 mmol, 88%), which was used in next step reaction without purification. LC/MS (uplc): $MH^+$ 160.1, 0.68 min.

Acylation of 2,5-difluorobenzimidohydrazide

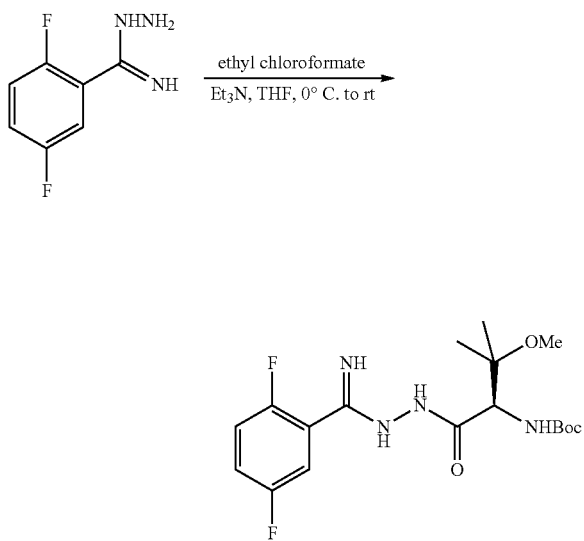

The crude (R)-2-((tert-butoxycarbonyl)amino)-3-methoxy-3-methylbutanoic acid (4 g, 16.2 mmol) was converted to a mixed anhydride by adding $Et_3N$ (3.38 ml, 24.26 mmol), ethyl chloroformate (1.931 g, 17.79 mmol) in anhydrous THF (32.4 ml, 0.5 M) at −5° C. to 0° C. The mixture was stirred at −5° C. for 30 min. The resulting solid was filtered off and additional anhydrous THF was added to wash the precipitate. The resulting reaction solution was then added to a THF solution of 2,5-difluorobenzimido-hydrazide (2.77 g, 16.18 mmol) at −5° C. Then the reaction was gradually warmed to room temperature and stirred for overnight. Once the reaction was complete, the mixture was partitioned between EtOAc and $H_2O$. The organic layer was separated and washed with $H_2O$, brine, then dried over anhydrous $Na_2SO_4$, filtered, and evaporated under reduced pressure to give the crude product, which was purified on silica gel column (50% EtOAc in Hexanes) to afford (R)-tert-butyl (1-(2-((2,5-difluorophenyl) (imino)methyl)hydrazinyl)-3-methoxy-3-methyl-1-oxobutan-2-yl)carbamate (1 g, 15%). LC/MS (uplc): $MH^+$ 401.2, 0.61 min.

Synthesis of (S)-tert-butyl (1-(3-(2,5-difluorophenyl)-1H-1,2,4-triazol-5-yl)-2-methoxy-2-methylpropyl)carbamate

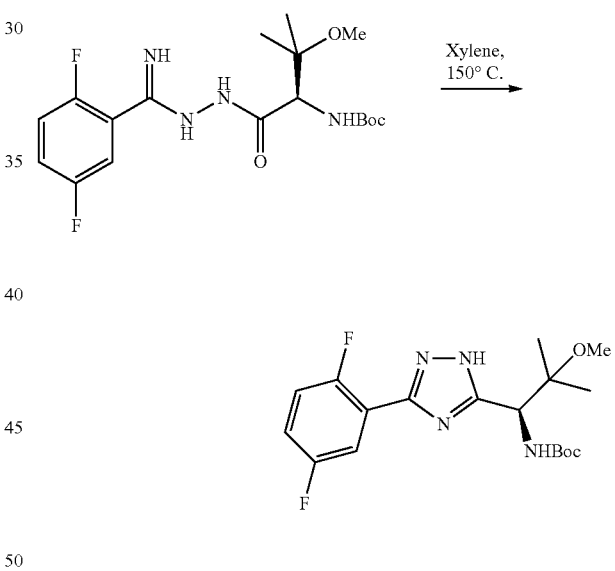

(R)-tert-Butyl 1-(2-((2,5-difluorophenyl)(imino)methyl) hydrazinyl)-3,3-dimethyl-1-oxobutan-2-ylcarbamate (1.0 g, 2.497 mmol) was dissolved in xylenes (8 mL). A Dean-Stark trap was equipped and the reaction mixture was heated to 160° C. Once the reaction was complete, the mixture was allowed to cool to room temperature, then partitioned between EtOAc and saturated aqueous $NaHCO_3$ solution. The organic layer was separated, then washed with saturated aqueous $NaHCO_3$ solution, $H_2O$, and brine, then dried over $Na_2SO_4$, filtered, and evaporated under reduced pressure to give (S)-tert-butyl (1-(3-(2,5-difluorophenyl)-1H-1,2,4-triazol-5-yl)-2-methoxy-2-methylpropyl)carbamate (0.97 g, 98%), which was used for the next step without further purification. LC/MS (uplc): $MH^+$ 383.2, 0.9 min.

TABLE 2

| Cmpd # | Mol Structure | KSP IC50 (uM) | LCMS/ Rt (min) | MH+ |
|---|---|---|---|---|
| 7 | | 0.00123 | 0.86 | 578.2 |
| 8 | | 0.00149 | 0.82 | 552.3 |
| 9 | | 0.04941 | 0.92 | 618.3 |

TABLE 2-continued

| Cmpd # | Mol Structure | KSP IC50 (uM) | LCMS/Rt (min) | MH+ |
|---|---|---|---|---|
| 10 | | 0.0009 | 0.88 | 590.2 |
| 11 | | 0.0014 | 0.86 | 560.4 |
| 12 | | 0.00087 | 0.85 | 564.4 |
| 13 | | 0.00069 | 0.89 | 572.4 |

TABLE 2-continued

| Cmpd # | Mol Structure | KSP IC50 (uM) | LCMS/ Rt (min) | MH+ |
|---|---|---|---|---|
| 14 | | 0.00234 | 0.82 | 534.4 |

NMR data for representative compounds of this type is provided here:

| Cmpd No. | $^1$H NMR data |
|---|---|
| 7 | $^1$H NMR (CD$_3$OD, 400 MHz) δ 7.87-7.73 (m, 1H), 7.45-7.31 (m, 1H), 7.32-7.11 (m, 4H), 7.11-6.95 (m, 1H), 6.2 (s, 1H), 5.61-5.29 (m, 2H), 4.81-4.69 (m, 1H), 4.51-4.3 (m, 1H), 4.29-3.97 (m, 3H), 3.95-3.80 (m, 1H), 3.75-3.61 (m, 1H), 3.16 (s, 3H), 2.38-2.21 (m, 1 H), 2.17-1.81 (m, 3H), 1.80-1.66 (m, 1H), 1.26-1.16 (m, 1H), 1.15 (s, 3H), 1.05 (s, 3H), 0.94-0.73 (m, 1H) |
| 8 | $^1$H NMR (CD$_3$OD, 400 MHz) δ 7.85-7.71 (m, 1H), 7.45-7.32 (m, 1H), 7.31-7.14 (m, 4H), 7.11-7.00 (m, 1H), 6.2 (s, 1H), 5.63-5.34 (m, 2H), 5.6-5.3 (m, 2H), 4.62-4.40 (m, 2H), 4.38-4.23 (m, 1H), 4.21-3.98 (m, 2H), 3.69-3.55 (m, 1H), 3.23-3.09 (m, 3H), 2.05-1.94 (m, 1H), 1.76-1.56 (m, 1H), 1.50-1.37 (m, 1H), 1.26-1.15 (m, 2H), 1.14 (s, 3H), 1.03 (s, 3H), 0.90-0.74 (m, 1H) |
| 10 | $^1$H NMR (CD$_3$OD, 400 MHz) δ 7.8 (m, 1H), 7.4 (m, 1H), 7.34-7.14 (m, 4H), 7.09 (m, 1H), 6.2 (s, 1H), 5.67-5.39 (m, 2H), 4.78 (m, 1H), 4.36-3.99 (m, 3H), 3.99-3.80 (m, 1H), 3.55-3.37 (m, 1H), 3.38-3.32 (m, 1H), 3.12 (s, 3H), 2.87-2.69 (m, 1H), 2.55-2.22 (m, 2H), 2.22-2.04 (m, 2H), 2.04-1.79 (m, 2H), 1.46-1.31 (m, 1H), 1.28-1.10 (m, 4H), 1.10-0.93 (m, 3H) |
| 14 | $^1$H NMR (CD$_3$Cl, 400 MHz): δ 7.80-7.68 (m, 1H), 7.4-7.26 (s, 4H), 7.22-6.97 (m, 3H), 6.10-5.97 (s, 1H), 5.56-5.25 (m, 2H), 4.68 (m, 1H), 4.30-3.89 (m, 3H), 3.86-3.51 (m, 1H), 3.2-3.1 (m, 1H), 3.07 (s, 3H), 1.58-1.43 (m, 2H), 1.35 (d, 3H), 1.25 (m, 1H), 1.05 (s, 3H), 0.94 (s, 3H), 0.5 (m, 1H) |

Example 8

Inhibition of Cellular Proliferation in Tumor Cell Lines Treated with KSP Inhibitors Cells are plated in 96-well plates at densities of about 500 cells per well of a 96-well plate and are allowed to grow for 24 hours. The cells are then treated with various concentrations of compounds for 72 hours. Then, 100 µl of CellTiter-Glo® solution are added. The CellTiter-Glo® assay measures the amount of ATP present in the well after lysing the cells; the ATP released is used in an enzymatic reaction including the enzyme Luciferease and its substrate Luciferin. The amount of light emitted is proportional to the amount of ATP, which in turn is proportional to the number of live cells in the well. (see Promega product catalog #G7573, CellTiter-Glo® Luminescent Cell Viability Assay). The cells are then incubated in the dark for 30 minutes. The amount of luminescence is determined for each well using a Wallac Trilux plate reader, which correlates with the number of cells per well. The number of viable cells in the wells that receive only DMSO (0.5%) serve as an indication of 0% inhibition, while wells without cells serve as 100% inhibition of cell growth. The compound concentration that results in a 50% growth inhibition (GI$_{50}$) is determined graphically from sigmoidal dose-response curves of log-transformed dose values versus cell counts (percent of control) at 72 hours of continuous compound exposure.

The cell lines used are listed below.
The cell proliferation assay is performed as described above.
 Cancer Cell Lines
 Colo 205-colon carcinoma
 RPMI 1640+10% FBS+1% L-glutamine+1% P/S+1% NaPyr.+Hepes+4.5 g/L Glucose+1% NaBicarb.
 MDA 435-breast cancer-high met
 EMEM+10% FBS+1% P/S+1% L-Glutamine+1% NEAA+1% NaPyr+1% vitamins
 HCT-15 and HCT116-colon carcinoma
 RPMI 1640+10% FBS+1% L-glutamine+1% P/S
 Drug Resistant Cell Lines
 KB3.1-colon epidermal carcinoma; parental cell line Iscove's+10% FBS+1% L-glutamine+1% P/S
KBV1-p-glycoprotein associated multi-drug resistant cell line
  RPMI 1640+10% FBS+1% L-glutamine+1% P/S+0.2 ug/mL Vinblastine
KB8.5-p-glycoprotein associated multi-drug resistant cell line
  DMEM+10% FBS+1% L-glutamine+1% P/S+10 ng/mL Colchicine Preferred compounds of the invention have a biological activity as measured by a $GI_{50}$ of less than about 1 mM in assay protocols described with some embodiments having biological activity of less than about 25 μM, with other embodiments having biological activity of less than about 1000 nM, and with still other embodiment having a $GI_{50}$ of less than about 100 nM.

Example 9

Clonogenic Softagar Assay Protocol

Human cancer cells are plated at a density of $3 \times 10^5$ cells per well in a 6-well plate. The next day, a compound of interest at a certain concentration is added to each well. After 24 and 48 hours of incubation, the cells are harvested, washed and counted. The following steps are performed using the Multimek 96 robot. Then, 500 viable cells per well are plated in a 96-well plate that is coated with PolyHema to prevent attachment of the cells to the bottom of the well. Agarose (3% stock) is melted, diluted in warmed media and added to the cells to a final concentration of 0.5%. After the soft agar solidified, the plates are incubated at 37° C. for 6 days. Alamar blue dye added to and plates are incubated for an additional 6 hours. The is measured on a plate reader and is considered to correlate with the number of colonies formed in soft agar. A cancerous cell is able to grow on the agar and thus will show an increase in optical density. A reading of decreased optical density means that the cancer cells are being inhibited. It is contemplated that compounds of this invention will exhibit a decrease in optical density.

The invention claimed is:

1. A compound of Formula I

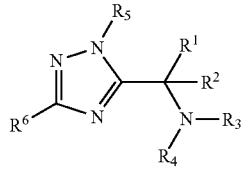

(I)

wherein:
$R^1$ is selected from $C_{1-6}$ alkoxy-$C_{1-4}$-alkyl;
$R^2$ is selected from H, and $C_{1-6}$ straight chain alkyl;
$R^3$ represents —(CH$_2$)$_{0-3}$ substituted or unsubstituted pyrrolidinyl;
$R^4$ is selected from —C(O)—CH$_2$OH, —C(O)-tetrahydrofuranyl, —C(O)—CH(CH$_3$)—OH, —C(O)-unsubstituted morpholinyl, and —C(O)-morpholinyl substituted with up to three alkyl groups;
$R^5$ is selected from substituted or unsubstituted benzyl, wherein the substituents are selected from Cl, F, Br, and I; and
$R^6$ is selected from phenyl substituted with up to three halogen atoms.

2. A compound of claim 1, wherein:
$R^1$ is selected from $C_{1-6}$alkoxy-$C_{1-4}$-alkyl;
$R^2$ represents H;
$R^3$ represents —(CH$_2$)$_{1-3}$-substituted pyrrolidinyl;
$R^4$ is selected from —C(O)-tetrahydrofuranyl, —C(O)—CH(CH$_3$)—OH, —C(O)-morpholinyl substituted with up to three alkyl groups;
$R^5$ represents benzyl, or benzyl substituted with up to two fluoro atoms; and
$R^6$ is selected from phenyl substituted with up to two halogen atoms.

3. A compound of claim 1, wherein:
$R^1$ represents $C_{1-6}$ alkoxy-$C_{1-4}$-alkyl;
$R^3$ represents —(CH$_2$)-fluoro-pyrrolidinyl;
$R^4$ is selected from —C(O)-tetrahydrofuranyl, —C(O)—CH(CH$_3$)—OH, —C(O)-2,6-dimethyl morpholinyl;
$R^5$ represents benzyl, or benzyl substituted with one fluoro atom; and
$R^6$ is selected from phenyl substituted with up to two fluoro atoms.

4. A compound of claim 2, wherein:
$R^3$ represents —(CH$_2$)$_{1-3}$-fluoro-pyrrolidinyl; and
$R^4$ represents —C(O)-2-tetrahydrofuranyl, —C(O)—CH(CH$_3$)—OH, or —C(O)-2,6-dimethyl morpholinyl.

5. A compound of claim 4, wherein:
$R^3$ represents

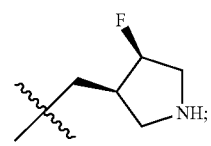 [SMILES: *C[C@@H]1CNC[C@@H]1F]

$R^4$ is selected from —C(O)—CH(CH$_3$)—OH, and

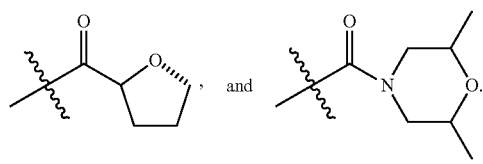

6. A compound of claim 5, wherein:
$R^5$ represents

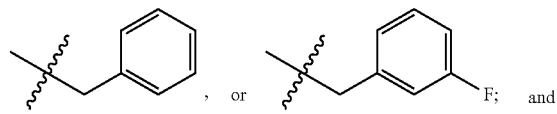 [SMILES: *Cc1ccccc1 ; *Cc1cccc(F)c1 ; "," ; "or" ; "and"]

$R^6$ is

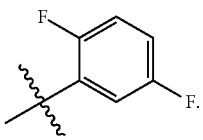 [SMILES: *c1cc(F)ccc1F]

7. A compound according to claim 1, wherein $R^4$ is selected from:

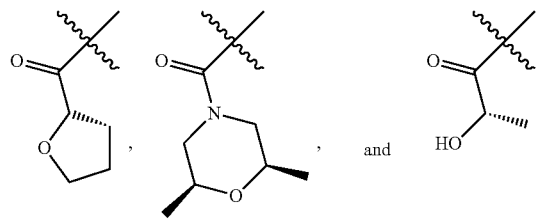

8. A compound selected from

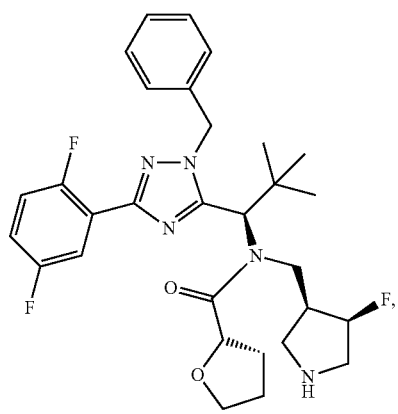

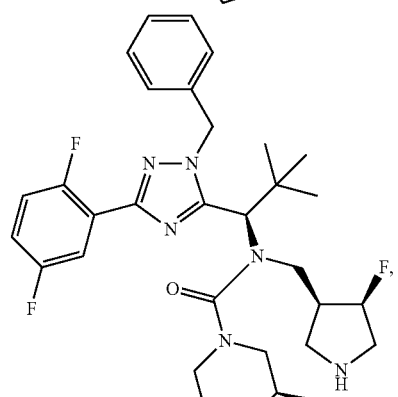

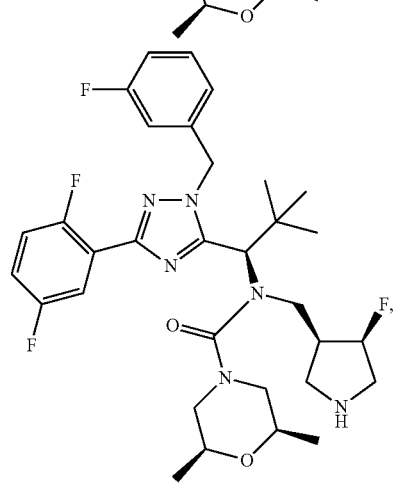

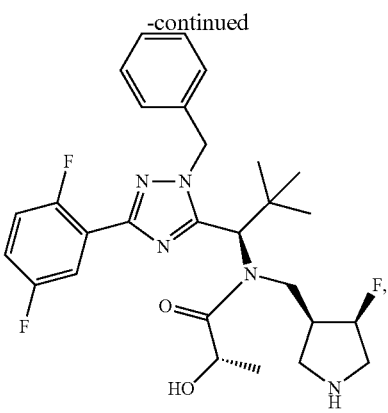

-continued

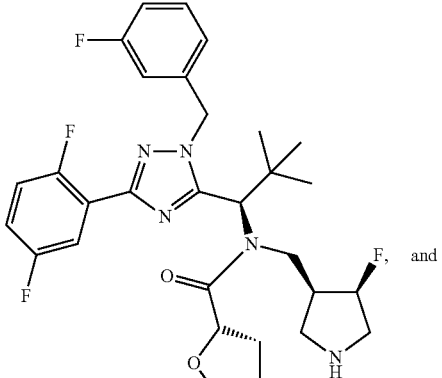

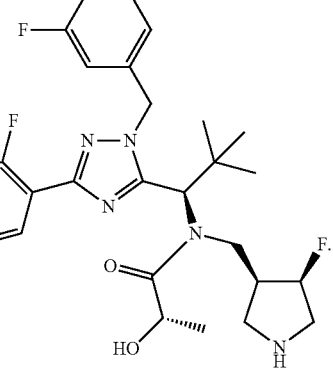

and the pharmaceutically acceptable salts of these compounds.

9. A compound of Formula (II):

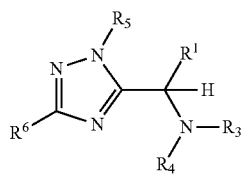

(II)

wherein,
$R^1$ is selected from $C_{1-6}$ alkoxy-$C_{1-4}$-alkyl;
$R^3$ represents —$(CH_2)_{0-3}$-substituted or unsubstituted pyrrolidinyl or $C_{3-5}$ alkyl substituted with up to three groups selected from amino and halo;
$R^4$ is selected from —C(O)—$CH_2$—OH, —C(O)-tetrahydrofuranyl, —C(O)—CH($CH_3$)—OH, —C(O)-unsubstituted morpholinyl, and —C(O)-morpholinyl substituted with up to three alkyl groups;
R⁵ is selected from substituted or unsubstituted benzyl, wherein the substituents are selected from Cl, F, Br, and I; and
R⁶ is selected from phenyl substituted with up to three halogen atoms.

10. The compound of claim 9, wherein:
R¹ is selected from $C_{1-6}$ alkoxy-$C_{1-4}$-alkyl;
R³ represents —(CH₂)₀₋₃-substituted pyrrolidinyl or —CH₂—CH₂—CH(NH₂)—CH₂F;
R⁴ is selected from —C(O)—CH₂OH, —C(O)-tetrahydrofuranyl, —C(O)—CH(CH₃)—OH, —C(O)-unsubstituted morpholinyl, and —C(O)-morpholinyl substituted with up to three alkyl groups;
R⁵ is selected from substituted or unsubstituted benzyl, wherein the substituents are selected from Cl, F, Br, and I; and
R⁶ is selected from phenyl substituted with up to three halogen atoms.

11. The compound of claim 9, wherein R¹ is methoxy-substituted $C_{1-4}$ alkyl.

12. The compound of claim 11, wherein R¹ is 2-methoxy-2-propyl.

13. A compound of claim 9, wherein:
R³ represents —(CH₂)₁₋₃-substituted pyrrolidinyl or —CH₂—CH₂—CH(NH₂)—CH₂F;
R⁴ is selected from —C(O)-tetrahydrofuranyl, —C(O)—CH(CH₃)—OH, and —C(O)-morpholinyl substituted with up to three alkyl groups;
R⁵ represents benzyl, or benzyl substituted with up to two fluoro atoms; and
R⁶ is selected from phenyl substituted with up to two halogen atoms.

14. A compound of claim 13, wherein:
R¹ represents 2-methoxy-2-propyl;
R³ represents —(CH₂)-fluoro-pyrrolidinyl or —CH₂—CH₂—CH(NH₂)—CH₂F;
R⁴ is selected from —C(O)-tetrahydrofuranyl, —C(O)—CH(CH₃)—OH, and —C(O)-2,6-dimethyl morpholinyl;
R⁵ represents benzyl, or benzyl substituted with one fluoro atom; and
R⁶ is selected from phenyl substituted with up to two fluoro atoms.

15. A compound of claim 14, wherein:
R³ represents —(CH₂)₁₋₃-fluoro-pyrrolidinyl or —CH₂—CH₂—CH(NH₂)—CH₂F; and
R⁴ represents —C(O)-2-tetrahydrofuranyl, —C(O)—CH(CH₃)—OH, and —C(O)-2,6-dimethyl morpholinyl.

16. A compound of claim 15, wherein:
R³ represents

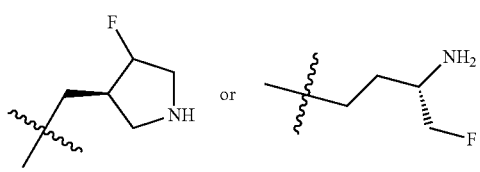 [SMILES: *C[C@@H]1CNCC1F ; *CC[C@H](N)CF]

R⁴ is selected from —C(O)—CH(CH₃)—OH,

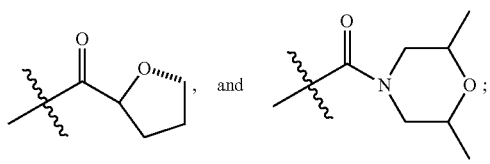

R⁵ is

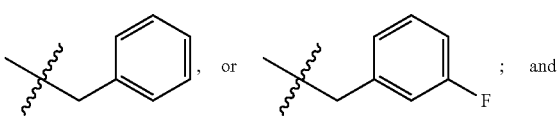 [SMILES: *Cc1ccccc1 ; *Cc1cccc(F)c1]

R⁶ is

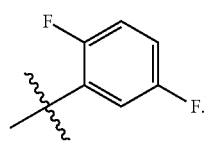 [SMILES: *c1cc(F)ccc1F]

17. The compound of claim 9, wherein R⁴ is selected from:

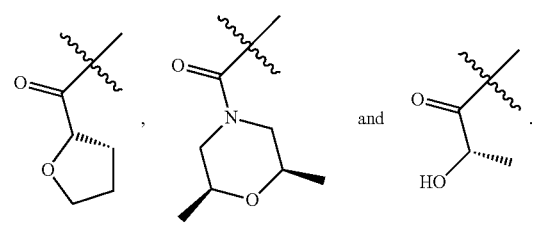

18. The compound of claim 9, wherein the compound is selected from the group consisting of:

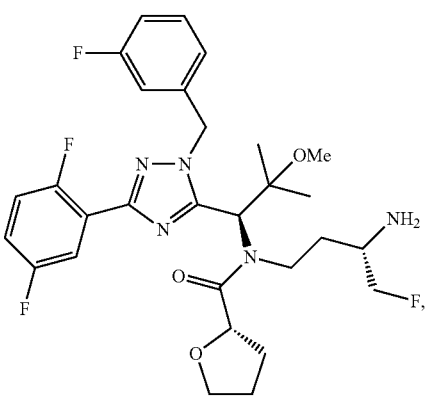

87
-continued

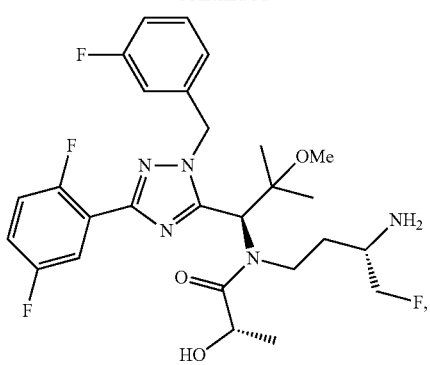

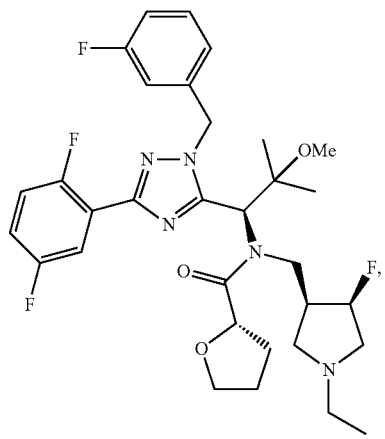

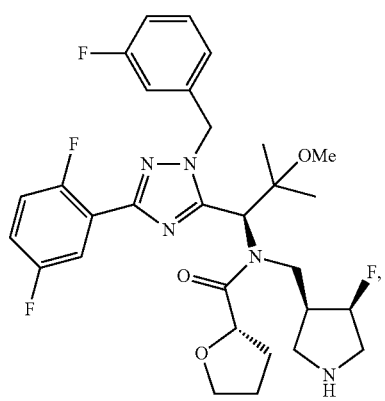

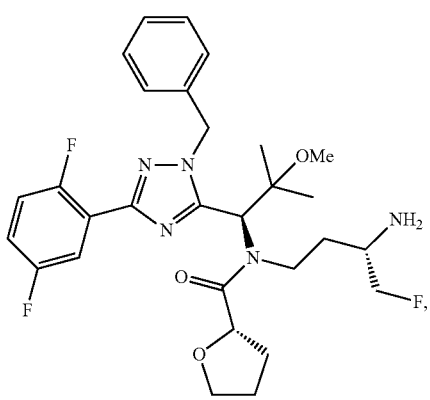

88
-continued

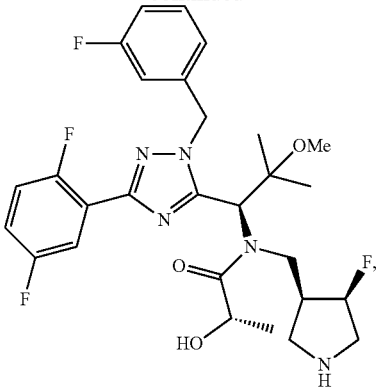

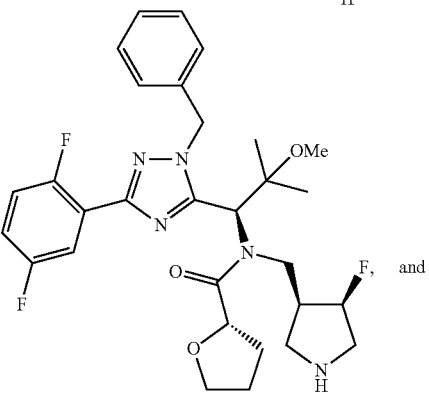

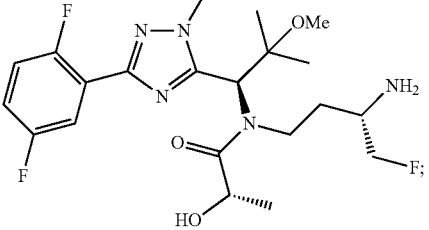

and the pharmaceutically acceptable salts thereof.

19. A pharmaceutical composition comprising a therapeutically effective amount of a compound of claim 1, and a pharmaceutically acceptable carrier.

20. The composition of claim 19 further comprising at least one additional agent for the treatment of cancer, wherein the additional agent for the treatment of cancer is selected from the group consisting of irinotecan, topotecan, gemcitabine, imatinib, trastuzumab, 5-fluorouracil, leucovorin, carboplatin, cisplatin, docetaxel, paclitaxel, tezacitabine, cyclophosphamide, vinca alkaloids, anthracyclines, rituximab, and trastuzumab.

21. A method of treating a disorder mediated, at least in part, by KSP in a mammalian patient comprising administering to a mammalian patient in need of such treatment a therapeutically effective amount of a compound of claim 1 wherein the disorder is cancer selected from the group consisting of lung and bronchus; prostate; breast; pancreas; colon and rectum; thyroid; stomach; liver and intrahepatic bile duct; kidney and renal pelvis; urinary bladder; uterine corpus; uterine cervix; ovary; multiple myeloma; esophagus; acute myelogenous leukemia; chronic myelogenous leukemia; lymphocytic leukemia; myeloid leukemia; brain; oral cavity and pharynx; larynx; small intestine; non-Hodgkin lymphoma; melanoma; and villous colon adenoma.

22. A method for inhibiting KSP in a mammalian patient, wherein said method comprises administering to the patient an effective KSP-inhibiting amount of a compound of claim 1.

* * * * *